US009969743B2

(12) United States Patent
Ananthan

(10) Patent No.: US 9,969,743 B2
(45) Date of Patent: May 15, 2018

(54) UREA AND AMIDE DERIVATIVES OF AMINOALKYLPIPERAZINES AND USE THEREOF

(71) Applicant: Southern Research Institute, Birmingham, AL (US)

(72) Inventor: Subramaniam Ananthan, Birmingham, AL (US)

(73) Assignee: SOUTHERN RESEARCH INSTITUTE, Birmingham, AL (US)

( * ) Notice: Subject to any disclaimer, the term of this patent is extended or adjusted under 35 U.S.C. 154(b) by 0 days. days.

(21) Appl. No.: 15/463,051

(22) Filed: Mar. 20, 2017

(65) Prior Publication Data

US 2017/0190711 A1    Jul. 6, 2017

Related U.S. Application Data

(62) Division of application No. 14/434,202, filed as application No. PCT/US2013/064524 on Oct. 11, 2013, now Pat. No. 9,598,387.

(60) Provisional application No. 61/712,333, filed on Oct. 11, 2012.

(51) Int. Cl.

| C07D 487/04 | (2006.01) |
| C07D 295/15 | (2006.01) |
| C07D 239/42 | (2006.01) |
| C07D 215/46 | (2006.01) |
| C07D 213/14 | (2006.01) |
| C07D 403/12 | (2006.01) |
| C07D 401/12 | (2006.01) |
| C07D 401/14 | (2006.01) |
| C07D 215/38 | (2006.01) |
| C07D 295/215 | (2006.01) |
| C07D 471/04 | (2006.01) |

(52) U.S. Cl.
CPC ......... *C07D 487/04* (2013.01); *C07D 213/14* (2013.01); *C07D 215/38* (2013.01); *C07D 215/46* (2013.01); *C07D 239/42* (2013.01); *C07D 295/215* (2013.01); *C07D 401/12* (2013.01); *C07D 401/14* (2013.01); *C07D 403/12* (2013.01); *C07D 471/04* (2013.01)

(58) Field of Classification Search
None
See application file for complete search history.

(56) References Cited

U.S. PATENT DOCUMENTS

| 5,576,318 A | 11/1996 | Bietti |
| 6,159,990 A | 12/2000 | Lagu et al. |
| 7,067,518 B2 | 6/2006 | Greenblatt et al. |
| 2004/0038855 A1 | 2/2004 | Salon et al. |
| 2005/0107395 A1 | 5/2005 | Greenblatt |
| 2007/0167458 A1 | 7/2007 | Bouchon et al. |
| 2009/0238761 A1 | 9/2009 | Campiani et al. |
| 2010/0240640 A1 | 9/2010 | Csongor et al. |

FOREIGN PATENT DOCUMENTS

| EP | 0 304 330 B1 | 2/1989 |
| EP | 0 526 434 B1 | 2/1993 |
| JP | 8 337570 A | 12/1996 |

(Continued)

OTHER PUBLICATIONS

CA Registry No. 1311955-44-8, entered into the Registry File on Jul. 7, 2011, supplied by Enamine.*

(Continued)

*Primary Examiner* — Emily Bernhardt
(74) *Attorney, Agent, or Firm* — Polsinelli PC

(57) ABSTRACT

Provided are compounds represented by the formula:

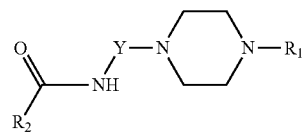

Formula I

In which:

Y is an unbranched, saturated or unsaturated hydrocarbon chain with 2-5 hydrocarbon atoms $R_1$=aryl $R_2$=$NR_3R_4$ wherein $R_3$ and $R_4$ together form a heterocycle or $R_2$=4-substitutedcyclohexyl, 1-substitutedpiperidine-4-yl or imidazo(1,2-a)azine-2-yl when Y is as defined above and $R_1$ is a heterocycle other than benzothiophene pharmaceutically acceptable salts thereof, deuterated forms thereof, isomers thereof, solvates thereof, and mixtures thereof.

The compounds can be used for treating a patient suffering from a condition that is capable of treatment with a partial agonist or antagonist of the dopamine D2/D3 receptors. The compounds are especially useful for patients suffering from schizophrenia, depressions, neurodegenerative diseases such as Parkinson's, dyskinesias, substance abuse and relapse to substance abuse and addiction to substances such as cocaine, methamphetamine, nicotine and alcohol, glaucoma, cognitive disorders, restless leg syndrome, attention deficit hyperactivity disorders, hyperprolactinemia, autism, motor disturbances such as akathisia, rigor, dystonias as well as various disorders of the urinary tract and other neurologic disorders. Also provided are processes for the preparation of compounds of the present disclosure.

6 Claims, 6 Drawing Sheets

(56) References Cited

FOREIGN PATENT DOCUMENTS

| JP | 2010-208945 A | 9/2010 |
|---|---|---|
| WO | WO-93/03016 A1 | 2/1993 |
| WO | WO-98/57940 A1 | 12/1998 |
| WO | WO-2006/015842 A1 | 2/2006 |
| WO | WO-2006/117760 A1 | 11/2006 |
| WO | WO-2008/047883 A1 | 4/2008 |

OTHER PUBLICATIONS

Enamine Product guide, 2 pages retrieved from the Internet at http://www.enamine.net/index.php?option=com_content &task=view&id=22 on Apr. 13, 2015.*

CA Registry No. 1311758-02-7, entered into the Registry File on Jul. 7, 2011, supplied by Enamine.*

Leopoldo et al., "First structure-Activity Relationship Study on Dopamine D3 Receptor Agents with N-[4-(4-Arylpiperazin-1-yl)butyl]-arylcarboxamide Structure", Journal of Medicinal and Pharmaceutical Chemistry, vol. 48, No. 25, Dec. 2015.

Extended European Search Report dated Feb. 8, 2016 in EP Appln 13846057.1.

CA Registry No. 1371086-73-5, entered into Registry File on Apr. 29, 2012. Supplied by Interchim Supplier.

Lagu et al., "Synthesis and Evaluation of Furo[3,4-α]pyrimidinones as Selective $\alpha_{1a}$-Adrenergic Receptor Antagonists", Bioorganic & Medicinal Chemistry Letters, 10 (2000) 175-178.

CA Registry No. 1348914-70-4, entered into the Registry File on Dec. 5, 2011, supplied by GVK Bio.

CA Registry No. 1289705-70-9, entered into the Registry File on May 4, 2011, supplied by FCH Group.

CA Registry No. 1259156-23-4, entered into the Registry File on Jan. 12, 2011, supplied by Chemcats.

CA Registry No. 1215679-29-0, entered into the Registry File on Apr. 2, 2010, supplied by Chemcats.

CA Registry No. 1317244-71-5, entered into the Registry File on Aug. 14, 2011, supplied by FCH Group.

CA Registry No. 1360311-81-4, entered into the Registry File on Mar. 7, 2012, supplied by Chemcats.

CA Registry No. 1089515-54-7, entered into the Registry File on Dec. 24, 2008, supplied by Ambinter.

Second Chinese Office Action dated Jun. 30, 2017 in CN Appl. 201380052932.4.

Australian Examiner Report dated Sep. 27, 2017 in AU Appl. 2013329097.

JP Office Action dated Jul. 18, 2017 in JP Appl. 2015-536930.

* cited by examiner

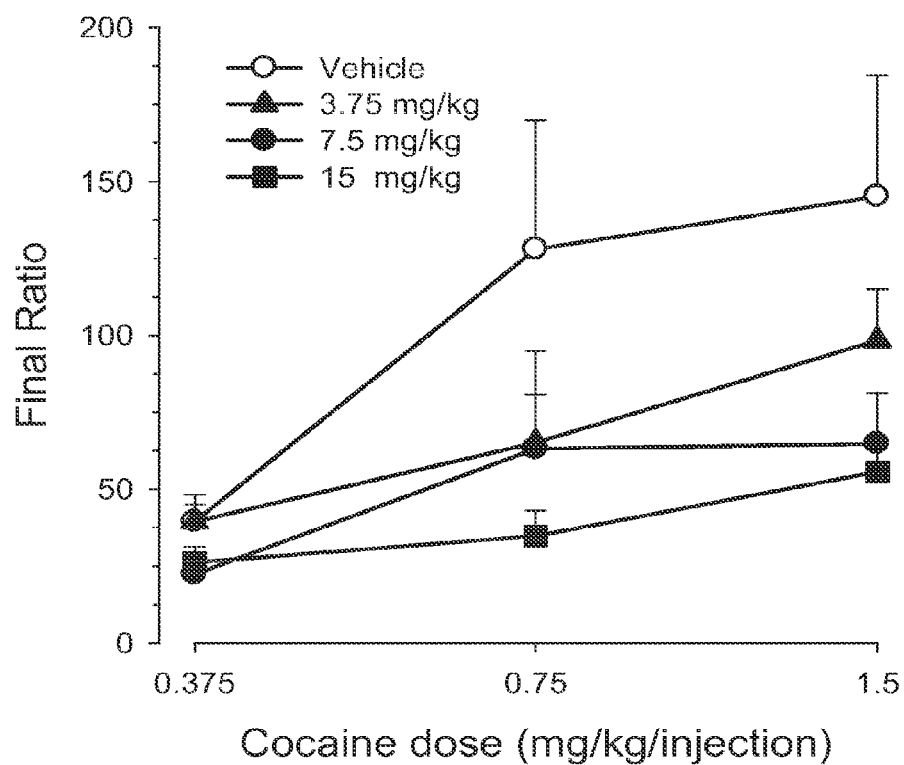
Figure 1. Effect of Compound 113 on intravenous cocaine self-administration under PR schedule of reinforcement. Acute administration Compound 113 has significant effect on percent baseline FR, $p < 0.05$.

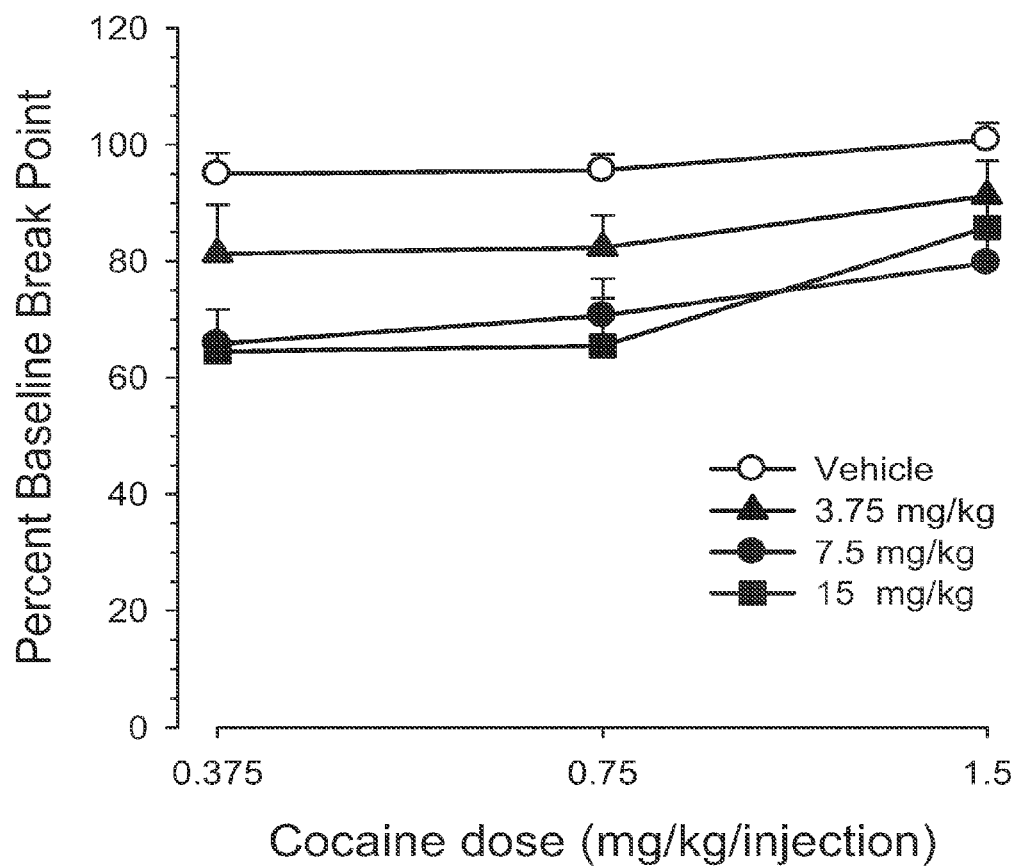
Figure 2. Effect of Compound 113 on intravenous cocaine self-administration under PR schedule of reinforcement. Acute administration of Compound 113 has dose-related effect on percent baseline BP, p <0.05.

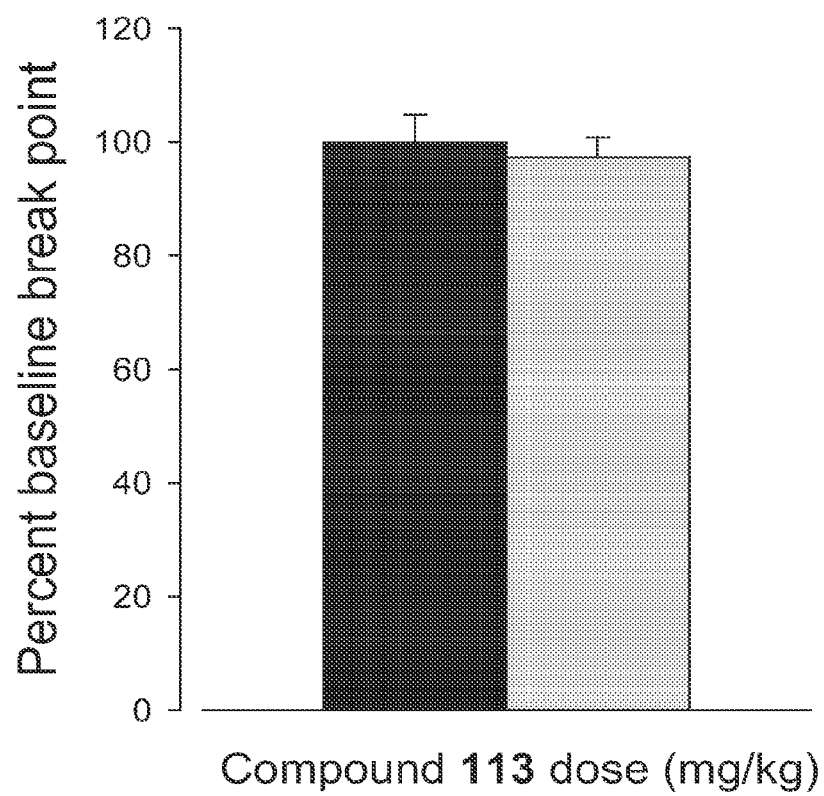
Figure 3. Effect of Compound 113 on food self-administration under PR schedule of reinforcement. Administration of Compound 113 has no effect on percent baseline BP.

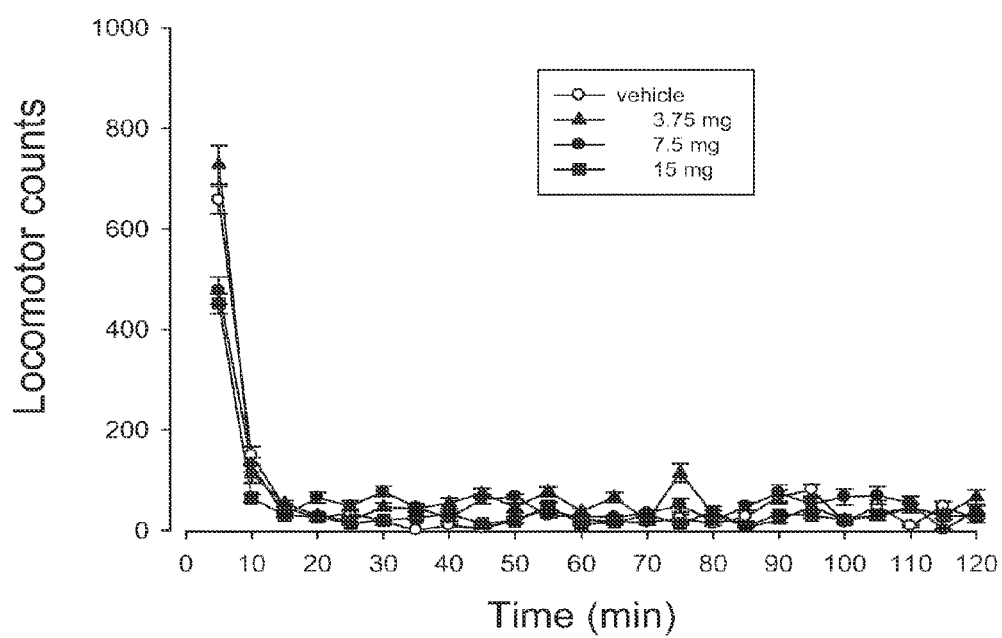
Figure 4. Effect of Compound 113 on spontaneous locomotor activity. Acute administration of Compound 113 has no significant effect on locomotor activity.

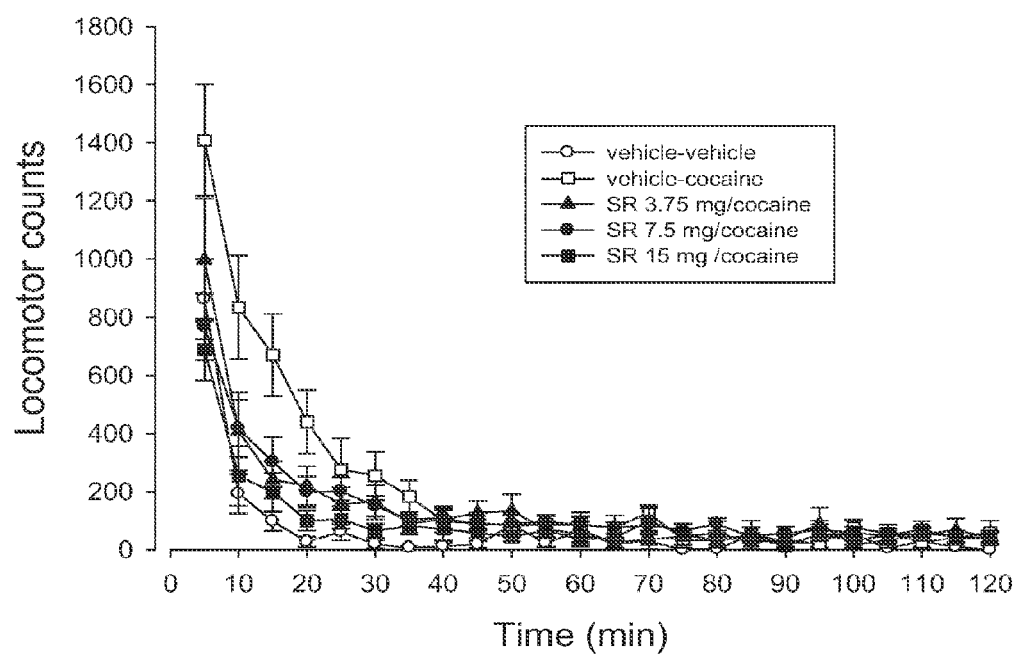
Figure 5. Effect of Compound 113 on cocaine-induced locomotor activity. Acute administration of Compound 113 has significant effect on cocaine-induced locomotor activity, $p<0.05$.

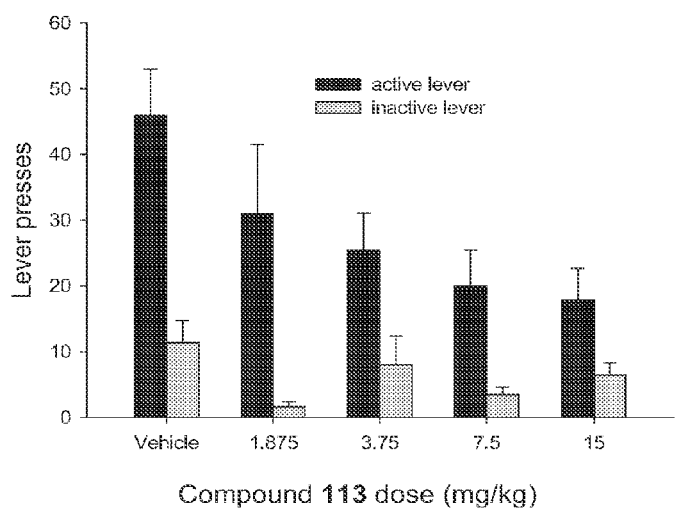
Figure 6. Mean (±SEM) presses on the active and inactive levers during the 60-min cue-induced reinstatement test. Administration of Compound 113 reduces cue-induced reinstatement of cocaine-seeking.

UREA AND AMIDE DERIVATIVES OF AMINOALKYLPIPERAZINES AND USE THEREOF

CROSS REFERENCE TO RELATED APPLICATIONS

This application is a Divisional of U.S. application Ser. No. 14/434,202 filed on Apr. 8, 2015, which is the National Phase filing under 35 U.S.C. § 371 of PCT/US2013/064524 filed on Oct. 11, 2013; and this application claims the benefit of U.S. Provisional Application No. 61/712,333 filed on Oct. 11, 2012. The entire contents of each application are hereby incorporated by reference.

FEDERALLY SPONSORED RESEARCH AND DEVELOPMENT

This invention was supported by the Contract N01-DA-1-8827 and Grant DA024675 from the National Institute on Drug Abuse of the National Institutes of Health and the US Government has certain rights in the invention.

TECHNICAL FIELD

The present disclosure relates to certain amides and ureas derived from aminobutyl piperazines. Compounds of the present disclosure are dopamine D3 receptor preferring antagonist or partial agonist ligands. Compounds of the present disclosure are useful as treatment agents for CNS and other neurological disorders where dopamine D3 receptors play a modulatory or pathological role and where modulation of dopamine signal transduction is beneficial. More particularly, compounds of the present disclosure are useful for treating schizophrenia; depressions; neurodegenerative diseases such as Parkinson's, dyskinesias, substance abuse and relapse to substance abuse and addiction to substances such as cocaine, methamphetamine, nicotine and alcohol; glaucoma; cognitive disorders; restless leg syndrome; attention deficit hyperactivity disorders; hyperprolactinemia; autism; motor disturbances such as akathisia, rigor, dystonias as well as various disorders of the urinary tract.

BACKGROUND

Dopamine (DA) is an important neurotransmitter in the central nervous system (CNS). Disturbances in dopaminergic signaling has been implicated in a number of neurobehavioral disorders such as schizophrenia, mania, depression, Parkinson's disease, movement and hyperactivity disorders and substance abuse. The actions of DA are mediated by five major subtypes of receptors, D1-D5. These receptors are seven transmembrane G-protein coupled receptors and have been broadly classified into D1-like receptors (D1 and D5) that couple positively to adenylyl cyclase and D2-like receptors (D2, D3 and D4) that couple negatively to adenylyl cyclase. Among the DA receptors, ligands that interact preferentially with the D3 subtype have attracted considerable attention as a drug development target in recent years (Hackling, A. E. et al. *ChemBioChem.* 2002, 3, 946-961; Joyce, J. N. et al. *Drug Discov. Today* 2005, 10, 917-925; Heidbreder, C. A. et al. *Brain Res. Rev.* 2005, 49, 77-105; Newman, A. H. et al. *J. Med. Chem.* 2005, 48, 3663-3679; Micheli, F. et al. *Recent Patents CNS Drug Discov.* 2006, 1, 271-288; Sokoloff, P. et al. *CNS. Neurol. Disord.* 2006, 5, 25-43; Boeckler, F. et al. *Biochim. Biophys. Acta* 2007, 1768, 871-887; Zhang, A. et al. *Chem. Rev.* 2007, 107, 274-302; Heidbreder, C. *CNS Neurol. Disord.* 2008, 7, 410-421; Heidbreder, C. A. and Newman, A. H. *Ann. N.Y. Acad. Sci.* 2010, 1187, 4-34; Löber, S. et al. *Trends Pharmacol. Sci.* 2011, 32, 148-157; Micheli, F. *ChemMedChem.* 2011, 6, 1152-1162). In contrast to D2 receptors that are predominantly expressed in the basal ganglions, the D3 receptors are mainly found in mesolimbic system that control emotional and cognitive processes. D3 receptors are elevated in mesolimbic regions of schizophrenic patients. Therefore, inhibition of D3 binding sites is expected to attenuate positive symptoms associated with schizophrenia without causing extrapyramidal side effects associated with classical D2 antagonists. Moreover, D3 antagonists have been shown to enhance D3 receptor mediated release of acetylcholine in the frontal cortex and are therefore expected to have beneficial effect on attention and memory thus improving the negative symptoms of schizophrenia (Lacroix, L. P. et al. *Neuropsychopharmacol.* 2003, 28, 839-849). Recent preclinical studies with D3 selective or D3 preferring antagonists have confirmed the effectiveness of D3 ligands as active in models of antipsychotic properties (Millan, M. J. et al. *J. Pharmacol. Exp. Ther.* 2008, 324, 1212-1226; Millan, M. J. et al. *Int. J. Neuropsychopharmacol.* 2010, 13, 1035-1051; Agai-Csongor, E. et al. *Bioorg. Med. Chem. Lett.* 2007, 17, 5340-5344 and 2012, 22, 3437-3440).

Studies in animal models have demonstrated that D3 receptor activation is involved in the reinforcing effects and self-administration of cocaine. Long-term exposure to cocaine results in upregulation of D3 receptors as demonstrated in postmortem studies of cocaine-overdose fatalities, and PET studies have shown upregulation of D3R over D2R in methamphetamine polydrug abusers. These observations suggested that D3R antagonism may be an effective strategy in the pharmacotherapy of addiction. Indeed, growing preclinical evidence with a number of D3R selective antagonist or partial agonist ligands have confirmed that these D3R ligands can effectively suppress motivation to self-administer drugs and prevent drug-associated cue-induced craving and relapse to drug taking. Recently D3 selective antagonists such as GSK598809 and GSK618334 have been investigated in Phase 1 clinical trials for their development as drugs for the treatment of substance dependence and alcoholism (Löber, S. et al. *Trends Pharmacol. Sci.* 2011, 32, 148-157; Newman, A. H. et al. *Biochem. Pharmacol.* 2012, 84, 882-890).

The development of dopamine D3 receptor ligands with selectivity over D2 receptor has been a considerable challenge due to the high degree of structural homology between these two receptors. There is 90% sequence similarity between these two receptors in their predicted transmembrane regions (Sibley, D. R. et al. *Trends Pharmacol. Sci.* 1992, 13, 61-69). The orthosteric ligand binding site in these two receptors is highly similar to each other with only two amino acid differences in the 21 residues that form the binding site crevice. Recent studies with X-ray crystal structure of D3 receptor and with models of D3 and D2 receptor-ligand complexes indicate that the selectivity of some of the reported D3 ligands may be attributable to the differential interaction of aromatic end groups, tethered to the the orthosteric binding moiety, at the accessory binding pocket located at the interface of TM1,2,3,7 and extracellular loops (EL1 and EL2) of D3 and D2 receptors (Chien, E. Y. T. et al. *Science* 2010, 330, 1091-1095; Banala, A. K. et al. *J. Med. Chem.* 2011, 54, 3581-3594; Newman, A. H. et al. *J. Med. Chem.* 2012, 55, 6689-6699). Arylpiperazines or heteroarylpiperazines tethered to hteroaromatic end groups have previously been described as dopamine receptor ligands in publications and patents (Reviews: Hackling, A. E. et al. *ChemBioChem.* 2002, 3, 946-961; Newman, A. H. et al. *J. Md. Chem.* 2005, 48, 3663-3679; Micheli, F. et al. *Recent Patents CNS Drug Discov.* 2006, 1, 271-288; Boeckler, F. et al. *Biochim. Biophys. Acta* 2007, 1768, 871-887; Zhang, A. et al. *Chem. Rev.* 2007, 107, 274-302; Heidbreder, C. A. and Newman, A. H. *Ann. N.Y. Acad. Sci.* 2010, 1187, 4-34; Löber, S. et al. *Trends Pharmacol. Sci.* 2011, 32, 148-157; Micheli, F. *ChemMedChem.* 2011, 6, 1152-1162. Geneste, H. et al. *Bioorg. Med. Chem. Lett.* 2006, 16, 490-494, 658-662 and 1934-1937. WO 2003028728, DE 10311065, DE 19735410, WO 2005056546, WO 2006015737, WO 2006015842, US 2008051409). Structure activity relationship (SAR) analysis on the binding selectivity and functional activity of such ligands indicate that these profiles are influenced both by the piperazine moiety that binds to the orthosteric binding site as well as by the aromatic end group that occupies the accessory binding pocket. Hence the prediction of affinity and selectivity profile of ligands possessing, for example, a piperazine head group tethered to an aromatic tail group remains difficult and not obvious.

SUMMARY OF DISCLOSURE

New compounds have been discovered, according to the present disclosure, that display D3 receptor binding selectivity over D2 receptor and antagonist or partial agonist functional activity at D3 and D2 receptors. The present disclosure relates to the synthesis and pharmacological profiles of the new D3 selective compounds. Compounds of the present disclosure are represented by following formula (I)

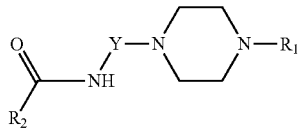

Formula I

In which:
Y is an unbranched, saturated or unsaturated hydrocarbon chain with 2-5 hydrocarbon atoms
$R_1$=aryl
$R_2$=$NR_3R_4$ wherein $R_3$ and $R_4$ together form a heterocycle or
$R_2$=4-substituted cyclohexyl, 1-substituted piperidine-4-yl or imidazo(1,2-a)azine-2-yl when Y is as defined above and $R_1$ is a heterocycle other than benzothiophene,
pharmaceutically acceptable salts thereof, deuterated forms thereof, isomers thereof, solvates thereof, and mixtures thereof.

The present disclosure is also concerned with a pharmaceutical composition comprising a pharmaceutically acceptable carrier and at least one of the above disclosed compounds of Formula I, pharmaceutically acceptable salts thereof, deuterated forms thereof, isomers thereof, solvates thereof, and mixtures thereof.

Another aspect of the present disclosure relates to a method for treating a patient suffering from a condition that is capable of treatment with an antagonist or partial agonist of the dopamine D2 and D3 receptors which comprising administering to said patient an effective amount of at least one of the above disclosed compounds of Formula I, pharmaceutically acceptable salts thereof, deuterated forms thereof, isomers thereof, solvates thereof.

Another aspect of the present disclosure relates to a method for treating a patient suffering from schizophrenia, depressions, neurodegenerative diseases such as Parkinson's, dyskinesias, substance abuse and relapse to substance abuse and addiction to substances such as cocaine, methamphetamine, nicotine and alcohol, glaucoma, cognitive disorders, restless leg syndrome, attention deficit hyperactivity disorders, hyperprolactinemia, autism, motor disturbances such as akathisia, rigor, dystonias as well as various disorders of the urinary tract, which comprises administering to the patient an effective amount of at least one of the above disclosed compounds of Formula I, pharmaceutically acceptable salts thereof, deuterated forms thereof, isomers thereof, solvates thereof.

A further aspect of the present disclosure relates to a process for preparing those compounds of Formula I which are ureas by reacting a 4-aminobutylpiperazine with carbonyldiimidazole and a secondary amine.

An additional aspect of the present disclosure relates to a process for preparing those compounds of Formula I which are amides by coupling a 4-aminobutylpiperazine with an acid.

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive.

BRIEF DESCRIPTION OF DRAWINGS

FIG. 1 is a graph illustrating the effect of a compound according to the present disclosure on intravenous cocaine self-administration under PR schedule of reinforcement, and as shown the acute administration of the compound according to the present disclosure has significant effect on percent baseline FR, $p<0.05$.

FIG. 2 is a graph illustrating the effect of a compound according to the present disclosure on intravenous cocaine self-administration under PR schedule of reinforcement, and as shown the acute administration of the compound according to the present disclosure has dose-related effect on percent baseline BP, $p<0.05$.

FIG. 3 is a graph illustrating the effect of a compound according to the present disclosure on food self-administration under PR schedule of reinforcement, and as shown the administration of the compound according to the present disclosure has no effect on percent baseline BP.

FIG. 4 is a graph illustrating the effect of a compound according to the present disclosure on spontaneous locomotor activity, and as shown the acute administration of the compound according to the present disclosure has no significant effect on locomotor activity.

FIG. 5 is a graph illustrating the effect of a compound according to the present disclosure on cocaine-induced locomotor activity, and as shown the acute administration of the compound according to the present disclosure has significant effect on cocaine-induced locomotor activity, $p<0.05$.

FIG. 6 is a graph illustrating the mean (±SEM) presses on the active and inactive levers during the 60-min cue-induced reinstatement test, and as shown the administration of the compound according to the present disclosure reduces cue-induced reinstatement of cocaine-seeking.

BEST AND VARIOUS MODES FOR CARRYING OUT DISCLOSURE

Compounds of the present disclosure are represented by following formula (I).

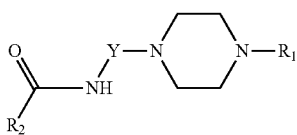

Formula I

In which:
Y is an unbranched, saturated or unsaturated hydrocarbon chain with 2-5 hydrocarbon atoms
$R_1$=aryl
$R_2$=$NR_3R_4$ wherein $R_3$ and $R_4$ together form a heterocycle or
$R_2$=4-substituted cyclohexyl, 1-substituted piperidine-4-yl or imidazo(1,2-a)azine-2-yl when Y is as defined above and $R_1$ is a heterocycle other than benzothiophene,
pharmaceutically acceptable salts thereof, deuterated forms thereof, isomers thereof, solvates thereof, and mixtures thereof.

In a preferred embodiment of the invention,
Y=$(CH_2)_n$ wherein n=4 and,
$R_1$ in the case of the ureas according to the present disclosure, is preferably phenyl, 2-methoxyphenyl, 2,3-dichlorophenyl or heteroaryl such as 2-pyridyl, 3-pyridyl, 4-pyridyl, 2-pyrimidinyl, 4-pyrimidinyl, 5-pyrimidinyl, 6-pyrimidinyl, 2-quinolinyl, 4-quinolinyl, 2-quinazolinyl, 4-quinazolinyl with heteroaryl substituents selected from the group consisting of H, hydroxyl, chlorine, fluorine, bromine, trifluoromethyl, cyano, amino, carboxy, sulfo, sulfamoyl, unsubstituted or hydroxyl substituted C1-C6 alkyl, unsubstituted or hydroxyl substituted C1-C6 alkylthio, unsubstituted or substituted C2-C6 alkenyl, unsubstituted or substituted C2-C6 alkynyl, alkoxy, unsubstituted or substituted aryl or unsubstituted or substituted heteroaryl. In the case of the amides according to the present disclosure, $R_1$ is preferably unsubstituted or substituted heteroaryl except for benzothiophene.

$R_2$=$NR_3R_4$ wherein $NR_3R_4$ is a 3 to 8 membered saturated or unsaturared aromatic or nonaromatic nitrogen-heterocycle such as aziridine, azetidine, pyrrolidine, dihydropyrrole, oxazoline, oxazolidine, isoxazolidine, thiazoline, thiazolidine, pyrazole, pyrazoline, pyrazolidine, imidazole, imidazoline, imidazolidine, triazole, dihydrotriazole, dihydrooxadiazole, piperidine, bipiperidine, dihydropyridine, dihydropyrimidine, dihydropyrazine, hexahydropyrimidine, oxazine, morpholine, thiamorpholine, piperazine, azepane, azepine, azocine, diazepane, indole, dihydroindole, indoline, benzimidazole, benzotriazole, indazole, carbazole, carboline, dihydrocarboline, tetrahydrocarboline, dihydroquinoline, tetrahydroquinoline, dihydroisoquinoline, tetrahydroisoquinoline, isoindoline, hexahydroisoindoline, octahydroisoindole, azaspirononane, azaspirodecane, diazaspirononane, spirocyclopentaindoline, benzoazepine, benzoxazoline, benzoxazine, dihydrobenzoxazine, dihydrothiazine, dihydrotriazolopyrazine, tetrahydrotriazolopyrazine, diazabicycloheptane, triazaspirodecane, tetrahydrobenzofuropyridine, tetrahydrobenzothienopyridine, nortropane, hexahydrobenzoquinoline, octahydrobenzoquinoline, octahydropyrazinoindole, hexahydropyrazinoquinoline, tetrahydrothiadiazine, diazabicycloheptane, diazabicyclooctane and tetrahydromethanobenzazepine. These N-containing heterocyclic rings may contain additional substituents or groups such as alky, aryl, arylalkyl, heteroaryl, heteroarylalkyl, alkenyl, alkoxy, hydroxyl, protected hydroxyl, alkanoyl, carboxy, alkoxycarbonyl and carbamoyl. They also may have one or more oxo, thioxo, imino, methylene or additional atoms such as O, N, S, P, Se and Te, and be part of a fused bicyclic or polycyclic saturated or unsaturated system.

In another preferred embodiment of the invention, Y is as defined above, $R_1$ is as defined above other than benzothiophene, and $R_2$=4-substituted cyclohexyl, 1-substituted piperidine-4-yl or imidazo(1,2-a)azine-2-yl possessing alkyl, aryl or heteroaryl groups as substituents. Examples of imidazoazines include imidazopyridine, imidazopyrimidine, imidazopyrazine, imidazopyridazine, and imidazotriazine.

Listed below are definitions of various terms used to describe this invention. These definitions apply to the terms as they are used throughout this specification, unless otherwise limited in specific instances, either individually or as part of a larger group.

The term "aryl" refers to monocyclic or bicyclic aromatic hydrocarbon groups having 6 to 12 carbon atoms in the ring portion, such as phenyl, naphthyl, biphenyl, and diphenyl groups, each of which may be substituted. Some typical substitutions for the aryl group include alkyl, alkenyl, alkynyl, cycloalkyl, halogen substituted alkyl, alkoxy, halogen substituted alkoxy, nitro, cyano, halogeno, aryl, aryloxy, alkoycarbonyl, hydroxy, protected hydroxyl, alkanoyl, sulfamoyl, alkylthio, alkylsulfonyl, hydroxysulfonyl, amino which may have groups such as alkyl, alkanoyl, cycloalkyl, aryl and aroyl groups, morpholinylcarbonylalkenyl, morpholinylcarbonylalkyl, pyrrolyl, prazolyl, dihydropyrazolyl, imiazolyl, triazolyl, pyridyl, pyrrolidinyl which may have oxo groups, morpholinyl, thiomorpholinyl, amidino, guanidino or heteocyclic groups.

The term "alkyl" refers to straight or branched chain unsubstituted hydrocarbon groups of 1 to 20 carbon atoms, more typically 1 to 6 carbon atoms and even more typically 1 to 4 carbon atoms.

Examples of suitable alkyl groups include methyl, ethyl and propyl. Examples of branched alkyl groups include isopropyl and t-butyl.

The alkoxy group typically contains 1 to 6 carbon atoms. Suitable alkoxy groups typically contain 1-6 carbon atoms and include methoxy, ethoxy, propoxy and butoxy.

The term "alkenyl" refers to straight or branched chain unsubstituted hydrocarbon groups typically having 3 to 6 carbon atoms.

The term "aralkyl" or alkylaryl refers to an aryl group bonded directly through an alkyl group, such as benzyl or phenethyl.

The term "cycloalkyl" refers to cyclic hydrocarbon ring systems typically containing 3-9 carbon atoms, with typical examples being cyclopropyl, cyclobutyl, cyclopentyl, cyclohexyl, and cycloheptyl.

The term "cycloalkylalkyl" refers to alkyl substituted cyclic hydrocarbon ring system wherein the cyclic hydrocarbon typically contains 3-6 carbon atoms, a typical example being cyclopropylalkyl.

The term "heterocyclo", refers to an optionally substituted, saturated or unsaturated aromatic or nonaromatic cyclic group, for example, which is a 3 to 7 membered monocyclic, 7 to 11 membered bicyclic, or 10 to 15 membered tricyclic ring system, which has at least one heteroatom and at least one carbon atom in the ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized.

Examples of N-heterocyclo groups are pyridyl, pyrrolidinyl, piperidinyl, piperazinyl, pyrrolyl, pyrazolyl, pyrazinyl, pyrimidinyl, pyridazinyl, imidazoyl and imidazolidinyl, 1,2,3 triazole and 1,2,4 triazole. Examples of O-heterocyclic groups are furanyl and pyranyl. Examples of S-heterocyclic groups are thiopyran and thiophene. Examples of heterocyclic groups containing both N and O are morpholinyl, oxazole, and isooxazole. Example of heterocyclic groups containing both N and S are thiomorpholine, thiazole and isothiazole.

Examples of halo groups are Cl, F, Br and I. An example of a haloalkyl group is trifluoromethyl.

"Pharmaceutically acceptable salts" refer to derivatives of the disclosed compounds wherein the parent compound is modified by making acid or base salts thereof. The compounds of this disclosure form acid addition salts with a wide variety of organic and inorganic acids and includes the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkonic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

The deuterated forms contain heavy hydrogen including deuterium and/or tritium.

It is understood that the compounds of the present disclosure relate to all optical isomers and stereo-isomers at the various possible atoms of the molecule, unless specified otherwise.

"Solvates" refers to the compound formed by the interaction of a solvent and a solute and includes hydrates. Solvates are usually crystalline solid adducts containing solvent molecules within the crystal structure, in either stoichiometric or nonstoichiometric proportions.

Some specific compounds according to the present disclosure are the following:

4-Phenyl-N-(4-(4-phenylpiperazin-1-yl)butyl)piperazine-1-carboxamide

4-Phenyl-N-(4-(4-(3-(trifluoromethyl)phenyl)piperazin-1-yl)butyl)piperazine-1-carboxamide N-(4-(4-(2,3-Dichlorophenyl)piperazin-1-yl)butyl)-4-phenylpiperazine-1-carboxamide N-(4-(4-(3-Cyano-5-(trifluoromethyl)phenyl)piperazin-1-yl)butyl)-4-phenylpiperazine-1-carboxamide N-(4-(4-(2-(tert-Butyl)-6-methylpyrimidin-4-yl)piperazin-1-yl)butyl)-4-phenylpiperazine-1-carboxamide N-(4-(4-(6-(tert-Butyl)-2-methylpyrimidin-4-yl)piperazin-1-yl)butyl)-4-phenylpiperazine-1-carboxamide N-(4-(4-(6-Methyl-2-(trifluoromethyl)pyrimidin-4-yl)piperazin-1-yl)butyl)-4-phenylpiperazine-1-carboxamide N-(4-(4-(2-(tert-Butyl)-6-(trifluoromethyl)pyrimidin-4-yl)piperazin-1-yl)butyl)-4-phenylpiperazine-1-carboxamide N-(4-(4-(2-(tert-Butyl)-6-cyclopropylpyrimidin-4-yl)piperazin-1-yl)butyl)-4-phenylpiperazine-1-carboxamide N-(4-(4-(2,6-Di-tert-butylpyrimidin-4-yl)piperazin-1-yl)butyl)-4-phenylpiperazine-1-carboxamide 4-Phenyl-N-(4-(4-(quinolin-4-yl)piperazin-1-yl)butyl)piperazine-1-carboxamide N-(4-(4-(7-Chloroquinolin-4-yl)piperazin-1-yl)butyl)-4-phenylpiperazine-1-carboxamide N-(4-(4-(2-(tert-Butyl)quinazolin-4-yl)piperazin-1-yl)butyl)-4-phenylpiperazine-1-carboxamide N-(4-(4-(2-(tert-Butyl)-6-(trifluoromethyl)pyrimidin-4-yl)piperazin-1-yl)butyl)-4-(2-chlorophenyl)piperazine-1-carboxamide N-(4-(4-(2-(tert-Butyl)-6-(trifluoromethyl)pyrimidin-4-yl)piperazin-1-yl)butyl)-4-(3-chlorophenyl)piperazine-1-carboxamide N-(4-(4-(2-(tert-Butyl)-6-(trifluoromethyl)pyrimidin-4-yl)piperazin-1-yl)butyl)-4-(4-chlorophenyl)piperidine-1-carboxamide N-(4-(4-(2-(tert-Butyl)-6-(trifluoromethyl)pyrimidin-4-yl)piperazin-1-yl)butyl)-4-cyano-4-phenylpiperidine-1-carboxamide N-(4-(4-(2-(tert-Butyl)-6-(trifluoromethyl)pyrimidin-4-yl)piperazin-1-yl)butyl)-4-(2,3-dichlorophenyl)piperazine-1-carboxamide N-(4-(4-(2-(tert-Butyl)-6-(trifluoromethyl)pyrimidin-4-yl)piperazin-1-yl)butyl)-4-(2-methoxyphenyl)piperazine-1-carboxamide N-(4-(4-(2-(tert-Butyl)-6-(trifluoromethyl)pyrimidin-4-yl)piperazin-1-yl)butyl)-4-(3-methoxyphenyl)piperazine-1-carboxamide N-(4-(4-(2-(tert-Butyl)-6-(trifluoromethyl)pyrimidin-4-yl)piperazin-1-yl)butyl)-4-(4-methoxyphenyl)piperazine-1-carboxamide N-(4-(4-(2-(tert-Butyl)-6-(trifluoromethyl)pyrimidin-4-yl)piperazin-1-yl)butyl)-4-(m-tolyl)piperazine-1-carboxamide N-(4-(4-(2-(tert-Butyl)-6-(trifluoromethyl)pyrimidin-4-yl)piperazin-1-yl)butyl)-4-(p-tolyl)piperazine-1-carboxamide N-(4-(4-(2-(tert-Butyl)-6-(trifluoromethyl)pyrimidin-4-yl)piperazin-1-yl)butyl)-4-(2,3-dimethylphenyl)piperazine-1-carboxamide N-(4-(4-(2-(tert-Butyl)-6-(trifluoromethyl)pyrimidin-4-yl)piperazin-1-yl)butyl)-4-(2-cyanophenyl)piperazine-1-carboxamide N-(4-(4-(2-(tert-Butyl)-6-(trifluoromethyl)pyrimidin-4-yl)piperazin-1-yl)butyl)-4-(3-cyanophenyl)piperazine-1-carboxamide N-(4-(4-(2-(tert-Butyl)-6-(trifluoromethyl)pyrimidin-4-yl)piperazin-1-yl)butyl)-4-(3-(trifluoromethyl)phenyl)piperazine-1-carboxamide
N-(4-(4-(2-(tert-Butyl)-6-(trifluoromethyl)pyrimidin-4-yl)piperazin-1-yl)butyl)-4-(4-(trifluoromethyl)phenyl)piperazine-1-carboxamide
N-(4-(4-(2-(tert-Butyl)-6-(trifluoromethyl)pyrimidin-4-yl)piperazin-1-yl)butyl)-4-(pyridin-2-yl)piperazine-1-carboxamide
N-(4-(4-(2-(tert-Butyl)-6-(trifluoromethyl)pyrimidin-4-yl)piperazin-1-yl)butyl)-4-(pyridin-3-yl)piperazine-1-carboxamide
N-(4-(4-(2-(tert-Butyl)-6-(trifluoromethyl)pyrimidin-4-yl)piperazin-1-yl)butyl)-4-(pyridin-4-yl)piperazine-1-carboxamide
N-(4-(4-(2-(tert-Butyl)-6-(trifluoromethyl)pyrimidin-4-yl)piperazin-1-yl)butyl)-4-(pyrimidin-2-yl)piperazine-1-carboxamide
N-(4-(4-(2-(tert-Butyl)-6-(trifluoromethyl)pyrimidin-4-yl)piperazin-1-yl)butyl)-4-(pyrazin-2-yl)piperazine-1-carboxamide
N-(4-(4-(2-(tert-Butyl)-6-(trifluoromethyl)pyrimidin-4-yl)piperazin-1-yl)butyl)-4-(quinolin-4-yl)piperazine-1-carboxamide
N-(4-(4-(2-(tert-Butyl)-6-(trifluoromethyl)pyrimidin-4-yl)piperazin-1-yl)butyl)-4-cyclopropylpiperazine-1-carboxamide
4-Benzyl-N-(4-(4-(2-(tert-butyl)-6-(trifluoromethyl)pyrimidin-4-yl)piperazin-1-yl)butyl)piperazine-1-carboxamide
4-Benzoyl-N-(4-(4-(2-(tert-butyl)-6-(trifluoromethyl)pyrimidin-4-yl)piperazin-1-yl)butyl)piperazine-1-carboxamide
N-(4-(4-(2-(tert-Butyl)-6-(trifluoromethyl)pyrimidin-4-yl)piperazin-1-yl)butyl)-3-(pyridin-4-yl)azetidine-1-carboxamide
N-(4-(4-(2-(tert-Butyl)-6-(trifluoromethyl)pyrimidin-4-yl)piperazin-1-yl)butyl)isoindoline-2-carboxamide
N-(4-(4-(2-(tert-Butyl)-6-(trifluoromethyl)pyrimidin-4-yl)piperazin-1-yl)butyl)-5-methoxyisoindoline-2-carboxamide
N-(4-(4-(2-(tert-Butyl)-6-(trifluoromethyl)pyrimidin-4-yl)piperazin-1-yl)butyl)-3,4-dihydroisoquinoline-2(1H)-carboxamide
N-(4-(4-(2-(tert-Butyl)-6-(trifluoromethyl)pyrimidin-4-yl)piperazin-1-yl)butyl)-4,5-dihydro-1H-benzo[d]azepine-3(2H)-carboxamide
4-([1,1'-Biphenyl]-2-yl)-N-(4-(4-(2-(tert-butyl)-6-(trifluoromethyl)pyrimidin-4-yl)piperazin-1-yl)butyl)piperazine-1-carboxamide
4-([1,1'-Biphenyl]-3-yl)-N-(4-(4-(2-(tert-butyl)-6-(trifluoromethyl)pyrimidin-4-yl)piperazin-1-yl)butyl)piperazine-1-carboxamide
4-([1,1'-Biphenyl]-4-yl)-N-(4-(4-(2-(tert-butyl)-6-(trifluoromethyl)pyrimidin-4-yl)piperazin-1-yl)butyl)piperazine-1-carboxamide
N-(4-(4-(2-(tert-Butyl)-6-methylpyrimidin-4-yl)piperazin-1-yl)butyl)-4-(phenylsulfonyl)piperazine-1-carboxamide
N-(4-(4-(2,3-Dichlorophenyl)piperazin-1-yl)butyl)-4-phenylpiperidine-1-carboxamide
N-(4-(4-(2-(tert-Butyl)-6-(trifluoromethyl)pyrimidin-4-yl)piperazin-1-yl)butyl)-4-phenylpiperidine-1-carboxamide
N-(4-(4-(2-(tert-Butyl)-6-(trifluoromethyl)pyrimidin-4-yl)piperazin-1-yl)butyl)-4-hydroxy-4-phenylpiperidine-1-carboxamide
4-Benzyl-N-(4-(4-(2-(tert-butyl)-6-(trifluoromethyl)pyrimidin-4-yl)piperazin-1-yl)butyl)piperidine-1-carboxamide
N-(4-(4-(2-(tert-Butyl)-6-(trifluoromethyl)pyrimidin-4-yl)piperazin-1-yl)butyl)-4-phenoxypiperidine-1-carboxamide
N-(4-(4-(2-(tert-Butyl)-6-methylpyrimidin-4-yl)piperazin-1-yl)butyl)-4-(2-oxo-2,3-dihydro-1H-benzo[d]imidazol-1-yl)piperidine-1-carboxamide
N-(4-(4-(2-(tert-Butyl)-6-(trifluoromethyl)pyrimidin-4-yl)piperazin-1-yl)butyl)-4-(2-oxo-2,3-dihydro-1H-benzo[d]imidazol-1-yl)piperidine-1-carboxamide
N-(4-(4-(2-(tert-Butyl)-6-(trifluoromethyl)pyrimidin-4-yl)piperazin-1-yl)butyl)-8-cyano-3,4-dihydro-1H-pyrido[4,3-b]indole-2(5H)-carboxamide
N-(4-(4-(2-(tert-Butyl)-6-(trifluoromethyl)pyrimidin-4-yl)piperazin-1-yl)butyl)-1,3,4,9-tetrahydro-2H-pyrido[3,4-b]indole-2-carboxamide
N-(4-(4-(2,6-Di-tert-butylpyrimidin-4-yl)piperazin-1-yl)butyl)-1,3,4,9-tetrahydro-2H-pyrido[3,4-b]indole-2-carboxamide
N-(4-(4-(2-(tert-Butyl)-6-(trifluoromethyl)pyrimidin-4-yl)piperazin-1-yl)butyl)-4-(4-chlorophenyl)piperazine-1-carboxamide
N-(4-(4-(2-(tert-Butyl)-6-(trifluoromethyl)pyrimidin-4-yl)piperazin-1-yl)butyl)-4-(o-tolyl)piperazine-1-carboxamide
N-(4-(4-(2-(tert-Butyl)-6-(trifluoromethyl)pyrimidin-4-yl)piperazin-1-yl)butyl)-4-(4-cyanophenyl)piperazine-1-carboxamide
N-(4-(4-(2-(tert-Butyl)-6-(trifluoromethyl)pyrimidin-4-yl)piperazin-1-yl)butyl)-4-(3,4-dichlorophenyl)piperazine-1-carboxamide
N-(4-(4-(2-(tert-Butyl)-6-(trifluoromethyl)pyrimidin-4-yl)piperazin-1-yl)butyl)-4-(3-cyano-5-(trifluoromethyl)phenyl)piperazine-1-carboxamide
4-(2-(tert-Butyl)-6-(trifluoromethyl)pyrimidin-4-yl)-N-(4-(4-(2-(tert-butyl)-6-(trifluoromethyl)pyrimidin-4-yl)piperazin-1-yl)butyl)piperazine-1-carboxamide
N-(4-(4-(2-(tert-Butyl)-6-(trifluoromethyl)pyrimidin-4-yl)piperazin-1-yl)butyl)-4-(7-chloroquinolin-4-yl)piperazine-1-carboxamide
N-(4-(4-(2-(tert-Butyl)-6-(trifluoromethyl)pyrimidin-4-yl)piperazin-1-yl)butyl)-4-methylpiperazine-1-carboxamide
N-(4-(4-(2-(tert-Butyl)-6-(trifluoromethyl)pyrimidin-4-yl)piperazin-1-yl)butyl)-4-ethylpiperazine-1-carboxamide
N-(4-(4-(2-(tert-Butyl)-6-(trifluoromethyl)pyrimidin-4-yl)piperazin-1-yl)butyl)-4-isopropylpiperazine-1-carboxamide
2-Benzyl-N-(4-(4-(2-(tert-butyl)-6-(trifluoromethyl)pyrimidin-4-yl)piperazin-1-yl)butyl)-4-cyclopropylpiperazine-1-carboxamide
N-(4-(4-(2-(tert-Butyl)-6-(trifluoromethyl)pyrimidin-4-yl)piperazin-1-yl)butyl)-4-(cyclopropylmethyl)piperazine-1-carboxamide
N-(4-(4-(2-(tert-Butyl)-6-(trifluoromethyl)pyrimidin-4-yl)piperazin-1-yl)butyl)-4-cyclohexylpiperazine-1-carboxamide
N-(4-(4-(2-(tert-Butyl)-6-(trifluoromethyl)pyrimidin-4-yl)piperazin-1-yl)butyl)-3,4-dihydroquinoline-1(2H)-carboxamide
N-(4-(4-(2-(tert-Butyl)-6-(trifluoromethyl)pyrimidin-4-yl)piperazin-1-yl)butyl)indoline-1-carboxamide
N-(4-(4-(2-(tert-Butyl)-6-(trifluoromethyl)pyrimidin-4-yl)piperazin-1-yl)butyl)-4-(3-cyanobenzyl)piperazine-1-carboxamide
N-(4-(4-(2-(tert-Butyl)-6-(trifluoromethyl)pyrimidin-4-yl)piperazin-1-yl)butyl)-4-(4-chlorophenyl)(phenyl)methyl)piperazine-1-carboxamide N-(4-(4-(2-(tert-Butyl)-6-(trifluoromethyl)pyrimidin-4-yl)piperazin-1-yl)butyl)-4-cinnamylpiperazine-1-carboxamide
N-(4-(4-(2-(tert-Butyl)-6-(trifluoromethyl)pyrimidin-4-yl)piperazin-1-yl)butyl)-[1,4'-bipiperidine]-1'-carboxamide
N-(4-(4-(2-(tert-Butyl)-6-(trifluoromethyl)pyrimidin-4-yl)piperazin-1-yl)butyl)-4-(1-methylpiperidin-4-yl)piperazine-1-carboxamide
N-(4-(4-(2-(tert-Butyl)-6-(trifluoromethyl)pyrimidin-4-yl)piperazin-1-yl)butyl)-4-(phenylsulfonyl)piperazine-1-carboxamide
N-(4-(4-(2,6-Di-tert-butylpyrimidin-4-yl)piperazin-1-yl)butyl)-4-(phenylsulfonyl)piperazine-1-carboxamide
N-(4-(4-(2-(tert-Butyl)-6-(trifluoromethyl)pyrimidin-4-yl)piperazin-1-yl)butyl)-4-(4-chlorophenyl)-4-hydroxypiperidine-1-carboxamide
N-(4-(4-(2-(tert-Butyl)-6-(trifluoromethyl)pyrimidin-4-yl)piperazin-1-yl)butyl)-4-cyclopropyl-2-phenylpiperazine-1-carboxamide
N-(4-(4-(2-(tert-Butyl)-6-(trifluoromethyl)pyrimidin-4-yl)piperazin-1-yl)butyl)-4-phenyl-1,4-diazepane-1-carboxamide
N-(4-(4-(2-(tert-Butyl)-6-(trifluoromethyl)pyrimidin-4-yl)piperazin-1-yl)butyl)-4-phenylazepane-1-carboxamide
4-Phenyl-N-(4-(4-(7-(trifluoromethyl)quinolin-4-yl)piperazin-1-yl)butyl)piperazine-1-carboxamide
4-Phenyl-N-(4-(4-(quinolin-2-yl)piperazin-1-yl)butyl)piperazine-1-carboxamide
N-(4-(4-(7-Chloroquinolin-4-yl)piperazin-1-yl)butyl)-4-phenylpiperidine-1-carboxamide
N-(4-(4-(3,5-Di-tert-butylphenyl)piperazin-1-yl)butyl)-4-phenylpiperazine-1-carboxamide
N-(4-(4-(2-(tert-Butyl)-6-(trifluoromethyl)pyrimidin-4-yl)piperazin-1-yl)butyl)-3-methyl-5,6-dihydro-[1,2,4]triazolo[4,3-a]pyrazine-7(8H)-carboxamide
N-(4-(4-(6-(tert-Butyl)-2-methylpyrimidin-4-yl)piperazin-1-yl)butyl)-3-methyl-5,6-dihydro-[1,2,4]triazolo[4,3-a]pyrazine-7(8H)-carboxamide
N-(4-(4-(2-(tert-Butyl)-6-(trifluoromethyl)pyrimidin-4-yl)piperazin-1-yl)butyl)-3,4-dihydro-1H-pyrido[4,3-b]indole-2(5H)-carboxamide
N-(4-(4-(2-(tert-Butyl)-6-(trifluoromethyl)pyrimidin-4-yl)piperazin-1-yl)butyl)-8-methyl-3,4-dihydro-1H-pyrido[4,3-b]indole-2(5H)-carboxamide
N-(4-(4-(2-(tert-Butyl)-6-(trifluoromethyl)pyrimidin-4-yl)piperazin-1-yl)butyl)-8-chloro-3,4-dihydro-1H-pyrido[4,3-b]indole-2(5H)-carboxamide
N-(4-(4-(2-(tert-Butyl)-6-(trifluoromethyl)pyrimidin-4-yl)piperazin-1-yl)butyl)-8-methoxy-3,4-dihydro-1H-pyrido[4,3-b]indole-2(5H)-carboxamide
N-(4-(4-(2-(tert-Butyl)-6-(trifluoromethyl)pyrimidin-4-yl)piperazin-1-yl)butyl)-8-(trifluoromethyl)-3,4-dihydro-1H-pyrido[4,3-b]indole-2(5H)-carboxamide
N-(4-(4-(6-(tert-Butyl)-2-methylpyrimidin-4-yl)piperazin-1-yl)butyl)-8-methyl-3,4-dihydro-1H-pyrido[4,3-b]indole-2(5H)-carboxamide
N-(4-(4-(6-(tert-Butyl)-2-methylpyrimidin-4-yl)piperazin-1-yl)butyl)-8-chloro-3,4-dihydro-1H-pyrido[4,3-b]indole-2(5H)-carboxamide
N-(4-(4-(6-(tert-Butyl)-2-methylpyrimidin-4-yl)piperazin-1-yl)butyl)-8-methoxy-3,4-dihydro-1H-pyrido[4,3-b]indole-2(5H)-carboxamide
N-(4-(4-(3,5-Di-tert-butylphenyl)piperazin-1-yl)butyl)-1,3,4,9-tetrahydro-2H-pyrido[3,4-b]indole-2-carboxamide
N-(4-(4-(6-(tert-Butyl)-2-methylpyrimidin-4-yl)piperazin-1-yl)butyl)-8-(trifluoromethyl)-3,4-dihydro-1H-pyrido[4,3-b]indole-2(5H)-carboxamide
4-Phenyl-N-(4-(4-(2-(trifluoromethyl)quinolin-4-yl)piperazin-1-yl)butyl)piperazine-1-carboxamide
4-Phenyl-N-(4-(4-(2-(trifluoromethyl)quinolin-4-yl)piperazin-1-yl)butyl)piperidine-1-carboxamide
N-(4-(4-(2-(tert-Butyl)-6-cyclopropylpyrimidin-4-yl)piperazin-1-yl)butyl)-1,3,4,9-tetrahydro-2H-pyrido[3,4-b]indole-2-carboxamide
N-(4-(4-(2-(tert-Butyl)-6-(trifluoromethyl)pyrimidin-4-yl)piperazin-1-yl)butyl)-3-oxo-4-phenylpiperazine-1-carboxamide
N-(4-(4-(2-(tert-Butyl)-6-(trifluoromethyl)pyrimidin-4-yl)piperazin-1-yl)butyl)-4-phenylcyclohexanecarboxamide
4-Phenyl-N-(4-(4-(quinolin-4-yl)piperazin-1-yl)butyl)cyclohexanecarboxamide
N-(4-(4-(7-Chloroquinolin-4-yl)piperazin-1-yl)butyl)-4-phenylcyclohexanecarboxamide
4-Phenyl-N-(4-(4-(quinolin-2-yl)piperazin-1-yl)butyl)cyclohexanecarboxamide
N-(4-(4-(2-(tert-Butyl)-6-methylpyrimidin-4-yl)piperazin-1-yl)butyl)-1-(5-(trifluoromethyl)pyridin-2-yl)piperidine-4-carboxamide
N-(4-(4-(2-(tert-Butyl)-6-(trifluoromethyl)pyrimidin-4-yl)piperazin-1-yl)butyl)-1-phenylpiperidine-4-carboxamide
1-Benzyl-N-(4-(4-(2-(tert-butyl)-6-(trifluoromethyl)pyrimidin-4-yl)piperazin-1-yl)butyl)piperidine-4-carboxamide
N-(4-(4-(2-(tert-Butyl)-6-(trifluoromethyl)pyrimidin-4-yl)piperazin-1-yl)butyl)-1-(5-(trifluoromethyl)pyridin-2-yl)piperidine-4-carboxamide
N-(4-(4-(2-(tert-Butyl)-6-methylpyrimidin-4-yl)piperazin-1-yl)butyl)imidazo[1,2-a]pyridine-2-carboxamide
N-(4-(4-(2-(tert-Butyl)-6-cyclopropylpyrimidin-4-yl)piperazin-1-yl)butyl)imidazo[1,2-a]pyridine-2-carboxamide
N-(4-(4-(2-(tert-Butyl)-6-(trifluoromethyl)pyrimidin-4-yl)piperazin-1-yl)butyl)imidazo[1,2-a]pyridine-2-carboxamide
N-(4-(4-(2-(tert-Butyl)-6-(trifluoromethyl)pyrimidin-4-yl)piperazin-1-yl)butyl)imidazo[1,2-a]pyrimidine-2-carboxamide
N-(4-(4-(2-(tert-Butyl)-6-(trifluoromethyl)pyrimidin-4-yl)piperazin-1-yl)butyl)imidazo[1,2-a]pyrazine-2-carboxamide
N-(4-(4-(2-(tert-Butyl)-6-(trifluoromethyl)pyrimidin-4-yl)piperazin-1-yl)butyl)-6-chloroimidazo[1,2-b]pyridazine-2-carboxamide
N-(4-(4-(Quinolin-4-yl)piperazin-1-yl)butyl)imidazo[1,2-a]pyridine-2-carboxamide
N-(4-(4-(7-Chloroquinolin-4-yl)piperazin-1-yl)butyl)imidazo[1,2-a]pyridine-2-carboxamide
N-(4-(4-(2-(tert-Butyl)-6-(trifluoromethyl)pyrimidin-4-yl)piperazin-1-yl)butyl)-5-(hydroxymethyl)imidazo[1,2-a]pyridine-2-carboxamide
N-(4-(4-(2-(tert-Butyl)-6-(trifluoromethyl)pyrimidin-4-yl)piperazin-1-yl)butyl)-3-((dimethylamino)methyl)imidazo[1,2-a]pyridine-2-carboxamide
N-(4-(4-(2-(tert-Butyl)-6-(trifluoromethyl)pyrimidin-4-yl)piperazin-1-yl)butyl)-5-((dimethylamino)methyl)imidazo[1,2-a]pyridine-2-carboxamide
N-(4-(4-(2,6-Di-tert-Butylpyrimidin-4-yl)piperazin-1-yl)butyl)imidazo[1,2-a]pyridine-2-carboxamide
N-(4-(4-(2-(tert-Butyl)quinazolin-4-yl)piperazin-1-yl)butyl)imidazo[1,2-a]pyridine-2-carboxamide
N-(4-(4-(7-(Trifluoromethyl)quinolin-4-yl)piperazin-1-yl)butyl)imidazo[1,2-a]pyridine-2-carboxamide
N-(4-(4-(6-(tert-Butyl)-2-methylpyrimidin-4-yl)piperazin-1-yl)butyl)imidazo[1,2-a]pyridine-2-carboxamide
N-(4-(4-(Quinolin-2-yl)piperazin-1-yl)butyl)imidazo[1,2-a]pyrimidine-2-carboxamide N-(4-(4-(Quinazolin-4-yl)piperazin-1-yl)butyl)imidazo[1,2-a]pyridine-2-carboxamide 3-Bromo-N-(4-(4-(quinolin-4-yl)piperazin-1-yl)butyl)imidazo[1,2-a]pyridine-2-carboxamide 3-Chloro-N-(4-(4-(quinolin-4-yl)piperazin-1-yl)butyl)imidazo[1,2-a]pyridine-2-carboxamide N-(4-(4-(2-(Trifluoromethyl)quinolin-4-yl)piperazin-1-yl)butyl)imidazo[1,2-a]pyridine-2-carboxamide as well as pharmaceutically acceptable salts thereof, deuterated forms thereof, isomers thereof, and solvates thereof.

Compounds of the present disclosure can be prepared from suitable starting materials by the generic methods shown in Scheme 1 for the ureas and Scheme 2 for the amides. The preparation of the ureas involves the synthesis of appropriate 4-aminobutylpiperazines (S4) and their reaction with carbonyldiimidazole and an appropriate secondary amine (S5). The needed piperazines and the secondary amines are either commercially available or can be prepared through synthetic methods reported in the literature.

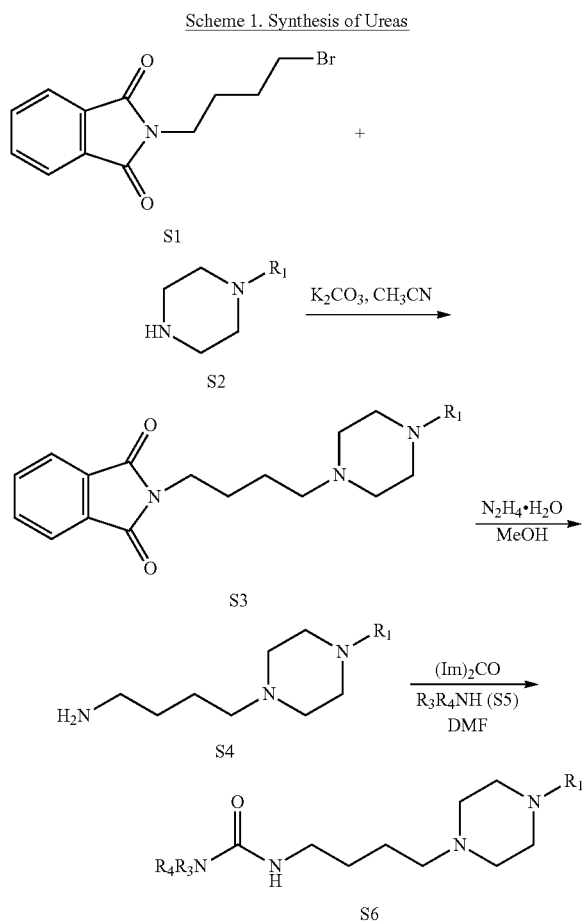

Scheme 1. Synthesis of Ureas

The amides are synthesized from the 4-aminobutylpiperazines (S4) by coupling with appropriate acids. The needed acids (S7) are either commercially available or can be prepared through synthetic methods reported in the literature.

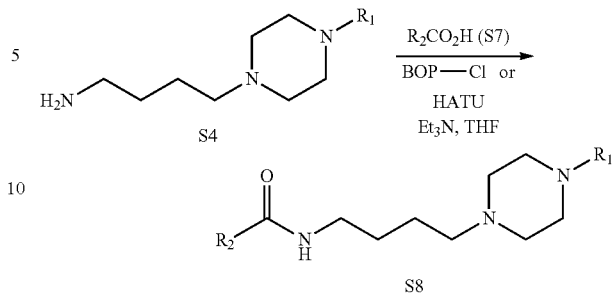

Scheme 2. Synthesis of Amides

The following non-limiting Examples are presented to further illustrate the present disclosure. The melting points were determined in open capillary tubes with a Mel-Temp melting point apparatus and are uncorrected. $^1$H NMR spectra were recorded on a Nicolet 300NB spectrometer operating at 300.635 MHz. Chemical shifts are expressed in parts per million downfield from tetramethylsilane. Spectral assignments were supported by proton decoupling. Mass spectra were recorded on a Varian MAT 311A double-focusing mass spectrometer in the fast atom bombardment (FAB) mode or on a Bruker BIOTOF II in electrospray ionization (ESI) mode. Thin layer chromatography (TLC) was performed on Analtech silica gel GF 0.25 mm plates. Flash column chromatography was performed with E. Merck silica gel 60 (230-400 mesh). Yields are of purified compounds and were not optimized. On the basis of NMR and combustion analysis, all final compounds were >95% pure.

EXAMPLE 1

4-Phenyl-N-(4-(4-phenylpiperazin-1-yl)butyl)piperazine-1-carboxamide (1). A solution of 4-(4-phenylpiperazin-1-yl)butan-1-amine (0.234 g, 1.0 mmol) and carbonyldiimidazole (CDI) (0.162 g, 1.0 mmol) in THF (8 mL) was stirred at room temperature for 16 hours. To the solution was added 1-phenylpiperazine (0.162 g, 1.0 mmol) and the mixture was heated under reflux for 24 hours. The reaction mixture was cooled to room temperature and mixture was partitioned between EtOAc (50 mL) and saturated aqueous sodium bicarbonate solution. The layers were separated and the aqueous layer was extracted with EtOAc (2×50 mL). The organic extracts were combined, dried over anhydrous sodium sulfate and concentrated under reduced pressure. The residue obtained was purified by chromatography over a column of silica using $CHCl_3$-MeOH (9:1) as the eluent to obtain 0.182 g (43%) of the desired product. mp 138-140° C. TLC $R_f$ 0.32 ($CHCl_3$-MeOH, 92.5:7.5); $^1$H NMR (DMSO-$d_6$) δ 1.41-1.48 (m, 4H), 2.28-2.34 (m 2H), 2.44-2.51 (m, 4H), 3.02-3.13 (m, 10H), 3.41-3.44 (m, 4H), 6.56 (t, 1H), 7.71-7.82 (m, 2H), 6.92-6.97 (m, 4H), 7.16-7.26 (m, 4H); ESI MS m/z 522 (MH)$^+$. Anal. ($C_{25}H_{35}N_5O$) Calcd: C, 71.23; H, 8.37; N, 16.61; Found: C, 71.30; H, 8.28; N, 16.55.

EXAMPLE 2

4-Phenyl-N-(4-(4-(3-(trifluoromethyl)phenyl)piperazin-1-yl)butyl)piperazine-1-carboxamide (2). Prepared from 4-(4-(3-(trifluoromethyl)phenyl)piperazin-1-yl)butan-1-amine, CDI and 1-phenylpiperazine as described in Example 1. Yield: 33%. mp 129-132° C. TLC $R_f$ 0.33 ($CHCl_3$-MeOH, 92.5:7.5); $^1$H NMR (DMSO-$d_6$) δ 1.44 (t, 4H), 2.31 (t, 2H), 2.40-2.50 (m, 4H), 3.04-3.09 (m, 6H), 3.20 (t, 4H), 3.43 (t, 4H), 6.57 (t, 1H), 6.66-6.82 (m, 1H) 6.95 (d, J=7.8 Hz, 2H), 7.04 (d, J=9.5 Hz, 1H), 7.14 (s, 1H), 7.18-7.24 (m, 3H), 7.38-7.43 (m, 1H); ESI MS m/z 490 (MH)$^+$. Anal. ($C_{26}H_{34}F_3N_5O.0.25H_2O$) Calcd: C, 63.21; H, 7.04; N, 14.17. Found: C, 63.28; H, 6.69; N, 14.09.

EXAMPLE 3

N-(4-(4-(2,3-Dichlorophenyl)piperazin-1-yl)butyl)-4-phenylpiperazine-1-carboxamide (3). A solution of carbonyldiimidazole (CDI) (0.98 g, 3.0 mmol) in THF (10 mL) was added dropwise to a solution of 4-(4-(2,3-dichlorophenyl)piperazin-1-yl)butan-1-amine (0.486 g, 3.0 mmol) in THF (15 mL). The mixture was stirred at room temperature overnight and then 1-phenylpiperazine (0.486 g, 3.0 mmol) was added and the mixture was heated at reflux for 24 hours. The reaction mixture was cooled to room temperature and mixture was partitioned between EtOAc (50 mL) and saturated aqueous sodium bicarbonate solution. The layers were separated. The aqueous layer was extracted with EtOAc (2×50 mL). The organic extracts were combined, dried over anhydrous sodium sulfate and concentrated under reduced pressure. The pale yellow viscous liquid thus obtained was purified by chromatography over a column of silica using EtOAc-MeOH (10:1) as the eluent to obtain 0.25 g (17%) of the desired product as a colorless solid. mp 142-144° C. $^1$HNMR (DMSO-d$_6$) δ 1.53-1.66 (m, 4H), 2.39-2.49 (t, J=7.36 Hz, 2H), 2.64 (bs, 4H), 3.07 (bs, 4H), 3.13-3.24 (m, 4H), 3.26-3.38 (m, 2H), 3.48-3.59 (t, J=5.06 Hz, 4H), 4.66 (t, J=5.08 Hz, 1H), 6.85-7.00 (m, 4H), 7.12-7.21 (m, 2H), 7.24-7.33 (m, 2H); ESI MS m/z 490 (MH)$^+$. Anal. ($C_{25}H_{33}Cl_2N_5O$) Calcd: C, 61.22; H, 6.78; N, 14.28. Found: C, 60.95; H, 6.68; N, 14.26.

EXAMPLE 4

N-(4-(4-(3-Cyano-5-(trifluoromethyl)phenyl)piperazin-1-yl)butyl)-4-phenylpiperazine-1-carboxamide (4). Prepared from 3-(4-(4-aminobutyl)piperazin-1-yl)-5-(trifluoromethyl)benzonitrile, CDI and 1-phenylpiperazine as described in Example 1. Yield: 29%. mp 136-138° C. TLC R$_f$ 0.25 (CHCl$_3$-MeOH, 92.5:7.5); $^1$HNMR (DMSO-d$_6$) δ 1.44-1.46 (m, 4H)), 2.34 (bs, 2H), 2.49-2.52 (m, 4H), 3.07 (t, 6H), 3.32 (s, 4H), 3.43 (t, 4H), 6.58 (t, 1H), 6.77-6.82 (m, 1H), 6.94 (dd, J=9.0, 8.6 Hz, 2H), 7.19-7.24 (m, 2H), 7.46 (s, 1H), 7.51 (s, 1H), 7.6 (s, 1H); ESI MS m/z 515 (MH)$^+$. Anal. ($C_{27}H_{33}F_3N_6O.H_2O$) Calcd: C, 60.89; H, 6.24; N, 15.80. Found: C, 60.92; H, 6.23; N, 16.14.

EXAMPLE 5

N-(4-(4-(2-(tert-Butyl)-6-methylpyrimidin-4-yl)piperazin-1-yl)butyl)-4-phenylpiperazine-1-carboxamide (5). Prepared from 4-(4-(2-(tert-butyl)-6-methylpyrimidin-4-yl)piperazin-1-yl)butan-1-amine, CDI and 1-phenylpiperazine as described in Example 1. Yield: 28%. mp 113-115° C. TLC R$_f$ 0.23 (CHCl$_3$-MeOH, 92.5:7.5); $^1$H NMR (DMSO-d$_6$) δ 1.25 (s, 9H), 1.40-1.48 (bs, 4H), 2.25 (s, 3H), 2.28-2.34 (bs, 2H), 2.44-2.51 (m, 4H), 3.02-3.1 (m, 6H), 3.41-3.44 (m, 4H), 3.56 (t, 4H), 6.45 (s, 1H), 6.57 (t, 1H), 6.79 (t, 1H), 6.94 (d, J=12.0 Hz, 2H), 7.22 (t, 2H); ESI MS m/z 494 (MH)$^+$. Anal. ($C_{28}H_{43}N_7O.0.25H_2O$) Calcd: C, 67.51; H, 8.80; N, 19.68. Found: C, 67.44; H, 8.64; N, 19.62.

EXAMPLE 6

N-(4-(4-(6-(tert-Butyl)-2-methylpyrimidin-4-yl)piperazin-1-yl)butyl)-4-phenylpiperazine-1-carboxamide (6). Prepared from 4-(4-(6-(tert-butyl)-2-methylpyrimidin-4-yl)piperazin-1-yl)butan-1-amine, CDI and 1-phenylpiperazine as described in Example 1. Yield: 26%. mp 140-142° C. TLC R$_f$ 0.33 (CHCl$_3$-MeOH, 95:5); $^1$HNMR (DMSO-d$_6$) δ 1.22 (s, 9H), 1.44 (bs, 4H), 2.29 (t, 2H), 2.33 (s, 3H), 2.39 (t, 4H), 3.02-3.09 (m, 6H), 3.42 (t, 4H), 3.57 (t, 4H), 6.47 (s, 1H), 6.57 (t, 1H), 6.76-6.83 (m, 1H), 6.92-6.98 (m, 2H), 7.17-7.25 (m, 2H); ESI MS m/z 494 (MH)$^+$. Anal. ($C_{28}H_{43}N_7O.0.25H_2O$) Calcd: C, 67.51; H, 8.80; N, 19.68. Found: C, 67.49; H, 8.64; N, 19.46.

EXAMPLE 7

N-(4-(4-(6-Methyl-2-(trifluoromethyl)pyrimidin-4-yl)piperazin-1-yl)butyl)-4-phenylpiperazine-1-carboxamide (7). Prepared from 4-(4-(6-methyl-2-(trifluoromethyl)pyrimidin-4-yl)piperazin-1-yl)butan-1-amine, CDI and 1-phenylpiperazine as described in Example 1. Yield: 36%. mp 120-122° C. TLC R$_f$ 0.58 (CHCl$_3$-MeOH, 90:10); $^1$H NMR (DMSO-d$_6$) δ 1.44 (bs, 4H), 2.30 (t, 2H), 2.37 (s, 3H), 2.41 (t, 4H), 3.03-3.09 (m, 6H), 3.42 (t, 4H), 3.63 (bs, 4H), 6.57 (t, 1H), 6.77-6.81 (m, 1H), 6.92-6.98 (m, 3H), 7.19-7.24 (m, 2H), ESI MS m/z 506 (MH)$^+$. Anal. ($C_{25}H_{34}F_3N_7O.0.25H_2O$) Calcd: C, 58.87; H, 6.82; N, 19.22. Found: C, 58.83; H, 6.66; N, 18.92.

EXAMPLE 8

N-(4-(4-(2-(tert-Butyl)-6-(trifluoromethyl)pyrimidin-4-yl)piperazin-1-yl)butyl)-4-phenylpiperazine-1-carboxamide (8). Prepared from 4-(4-(2-(tert-butyl)-6-(trifluoromethyl)pyrimidin-4-yl)piperazin-1-yl)butan-1-amine, CDI and 1-phenylpiperazine as described in Example 1. Yield: 56%. mp 120-122° C. TLC R$_f$ 0.45 (CHCl$_3$-MeOH, 90:10); $^1$H NMR (DMSO-d$_6$) δ 1.28 (s, 9H), 1.44 (bs, 4H), 2.31 (t, 2H), 2.41 (t, 4H), 3.04-3.09 (m, 6H), 3.43 (t, 4H), 3.70 (bs, 4H), 6.56 (t, 1H), 6.76-6.81 (m, 1H), 6.92-6.98 (m, 2H), 7.03 (s, 1H), 7.18-7.24 (m, 2H); ESI MS m/z 548 (MH)$^+$. Anal. ($C_{28}H_{40}F_3N_7O$) Calcd: C, 61.41; H, 7.30; N, 17.92. Found: C, 61.44; H, 7.21; N, 17.86.

EXAMPLE 9

N-(4-(4-(2-(tert-Butyl)-6-cyclopropylpyrimidin-4-yl)piperazin-1-yl)butyl)-4-phenylpiperazine-1-carboxamide (9). Prepared from 4-(4-(2-(tert-butyl)-6-cyclopropylpyrimidin-4-yl)piperazin-1-yl)butan-1-amine, CDI and 1-phenylpiperazine as described in Example 1. Yield: 32%. mp 138-140° C. TLC R$_f$ 0.32 (CHCl$_3$-MeOH, 95:5); $^1$H NMR (DMSO-d$_6$) δ 0.83-0.88 (m, 2H), 0.91-0.99 (m, 2H), 1.22 (s, 9H), 1.44 (bs, 4H)), 1.83-1.90 (m, 1H), 2.31 (bs, 2H), 2.40 (bs, 4H), 3.02-3.10 (m, 6H), 3.42 (t, 4H), 3.56 (bs, 4H), 6.48 (s, 1H), 6.57 (t, 1H), 6.78-6.80 (m, 1H), 6.94 (d, J=13.5 Hz, 2H), 7.19-7.22 (m, 2H); ESI MS m/z 520 (MH)$^+$. Anal. ($C_{30}H_{45}N_7O.0.5H_2O$) Calcd: C, 68.15; H, 8.77; N, 18.54. Found: C, 68.30; H, 8.64; N, 18.66.

EXAMPLE 10

N-(4-(4-(2,6-Di-tert-butylpyrimidin-4-yl)piperazin-1-yl)butyl)-4-phenylpiperazine-1-carboxamide (10). Prepared from 4-(4-(2,6-di-tert-butylpyrimidin-4-yl)piperazin-1-yl)butan-1-amine, CDI and 1-phenylpiperazine as described in Example 1. Yield: 31%. mp 144-146° C. TLC R$_f$ 0.27 (CHCl$_3$-MeOH, 95:5); $^1$H NMR (DMSO-d$_6$) δ 1.24 (s, 9H), 1.27 (s, 9H), 1.44 (bs, 4H)), 2.3 (bs, 2H), 2.40 (t, 4H), 3.00-3.08 (m, 2H), 3.07 (t, 4H), 3.42 (t, 4H), 3.58 (t, 4H), 6.44 (s, 1H), 6.57 (t, 1H), 6.76-6.80 (m, 1H), 6.94 (dd, J=8.7, 8.2 Hz 2H), 7.18-7.22 (m, 2H); ESI MS m/z 536 (MH)$^+$. Anal. ($C_{31}H_{49}N_7O.0.25H_2O$) Calcd: C, 68.92; H, 9.24; N, 18.15. Found: C, 68.85; H, 9.11; N, 18.11.

EXAMPLE 11

4-Phenyl-N-(4-(4-(quinolin-4-yl)piperazin-1-yl)butyl) piperazine-1-carboxamide (11). Prepared from 4-(4-(quinolin-4-yl)piperazin-1-yl)butan-1-amine, CDI and 1-phenylpiperazine as described in Example 1. Yield: 28%. mp 145-146° C. TLC R$_f$ 0.56 (CHCl$_3$-MeOH, 92.5:7.5); $^1$H NMR (DMSO-d$_6$) δ 1.47 (t, 4H), 2.40 (t, 2H), 2.65 (bs, 4H), 3.08 (t, 6H), 3.17 (bs, 4H), 3.43 (t, 4H), 6.57 (t, 1H), 6.78 (t, 1H), 6.92-6.97 (m, 3H), 7.19-7.24 (m, 2H), 7.51-7.57 (m, 1H), 7.67-7.71 (m, 1H), 7.93 (d, J=8.2 Hz, 1H), 7.99 (d, J=8.5 Hz, 1H), 8.67 (d, J=4.9 Hz, 1H); ESI MS m/z 473 (MH)$^+$. Anal. ($C_{28}H_{36}N_6O.H_2O$) Calcd: C, 68.54; H, 7.81; N, 17.12. Found: C, 68.37; H, 7.66; N, 17.08.

EXAMPLE 12

N-(4-(4-(7-Chloroquinolin-4-yl)piperazin-1-yl)butyl)-4-phenylpiperazine-1-carboxamide (12). Prepared from 4-(4-(7-chloroquinolin-4-yl)piperazin-1-yl)butan-1-amine, CDI and 1-phenylpiperazine as described in Example 1. Yield: 24%. mp 119-121° C. TLC R$_f$ 0.67 (CHCl$_3$-MeOH, 85:15); $^1$H NMR (DMSO-d$_6$) δ 1.46 (t, 4H), 2.39 (t, 2H), 2.64 (t, 4H), 3.07 (t, 6H), 3.17 (t, 4H), 3.43 (t, 4H), 6.58 (t, 1H), 6.78 (t, 1H), 6.91-7.01 (m, 3H), 7.19-7.24 (m, 2H), 7.54 (dd, J=9.0, 9.0 Hz, 1H), 7.97 (d, J=2.2 Hz, 1H), 8.00 (d, J=9.0 Hz, 1H), 8.69 (d, J=4.9 Hz, 1H); ESI MS m/z 546 (MH)$^+$. Anal. ($C_{28}H_{35}ClN_6O.0.25H_2O$) Calcd: C, 65.74; H, 6.99; N, 16.43. Found: C, 65.59; H, 6.73; N, 16.38.

EXAMPLE 13

N-(4-(4-(2-(tert-Butyl)quinazolin-4-yl)piperazin-1-yl)butyl)-4-phenylpiperazine-1-carboxamide (13). Prepared from 4-(4-(2-(tert-butyl)quinazolin-4-yl)piperazin-1-yl)butan-1-amine, CDI and 1-phenylpiperazine as described in Example 1. Yield: 25%. mp 141-142° C. TLC R$_f$ 0.50 (CHCl$_3$-MeOH, 92.5:7.5); $^1$HNMR (DMSO-d$_6$) δ 1.36 (s, 9H), 1.46 (bs, 4H), 2.38 (bs, 2H), 2.54 (t, 4H), 3.07 (t, 6H), 3.43 (t, 4H), 3.70 (t, 4H), 6.57 (t, 1H), 6.79 (t, 1H), 6.94-6.97 (m, 2H), 7.18-7.24 (m, 2H), 7.44-7.48 (m, 1H), 7.74-7.76 (m, 2H), 7.92 (d, J=8.4 Hz, 1H); ESI MS m/z 530 (MH)$^+$. Anal. ($C_{31}H_{43}N_7O.0.25H_2O$) Calcd: C, 69.68; H, 8.20; N, 18.38. Found: C, 69.52; H, 7.93; N, 18.31.

EXAMPLE 14

N-(4-(4-(2-(tert-Butyl)-6-(trifluoromethyl)pyrimidin-4-yl)piperazin-1-yl)butyl)-4-(2-chlorophenyl)piperazine-1-carboxamide (14). Prepared from 4-(4-(2-(tert-butyl)-6-(trifluoromethyl)pyrimidin-4-yl)piperazin-1-yl)butan-1-amine, CDI and 1-(2-chlorophenyl)piperazine as described in Example 1. Yield: 28%. mp 79-82° C. TLC R$_f$ 0.67 (CHCl$_3$-MeOH, 92.5:7.5); $^1$H NMR (DMSO-d$_6$) δ 1.28 (s, 9H), 1.45 (bs, 4H), 2.31 (bs, 2H), 2.42 (t, 4H), 2.91 (t, 4H), 3.05-3.07 (bq, 2H), 3.43-3.44 (t, 4H), 3.71 (bs, 4H), 6.54 (t, 1H), 7.03 (s, 1H), 7.05 (dd, J=8.0, 7.8 Hz, 1H), 7.15 (dd, J=8.0, 8.0 Hz, 1H), 7.25-7.32 (m, 1H), 7.41 (dd, J=8.0, 7.8 Hz, 1H); ESI MS m/z 582 (MH)$^+$. Anal. ($C_{28}H_{39}ClF_3N_7O$) Calcd: C, 57.77; H, 6.75; N, 16.84. Found: C, 57.57; H, 6.68; N, 16.84.

EXAMPLE 15

N-(4-(4-(2-(tert-Butyl)-6-(trifluoromethyl)pyrimidin-4-yl)piperazin-1-yl)butyl)-4-(3-chlorophenyl)piperazine-1-carboxamide(15). Prepared from 4-(4-(2-(tert-butyl)-6-(trifluoromethyl)pyrimidin-4-yl)piperazin-1-yl)butan-1-amine, CDI and 1-(3-chlorophenyl)piperazine as described in Example 1. Yield: 25%. mp 117-119° C. TLC R$_f$ 0.50 (CHCl$_3$-MeOH, 92.5:7.5); $^1$H NMR (DMSO-d$_6$) δ 1.28 (s, 9H), 1.44 (bs, 4H), 2.31 (bs, 2H), 2.42 (t, 4H), 3.04-3.08 (m, 2H), 3.12 (t, 4H), 3.41 (t, 4H), 3.70 (bs, 4H), 6.57 (t, 1H), 6.77 (dd, J=7.8, 7.8 Hz, 1H), 6.90 (dd, J=8.2, 8.2 Hz, 1H), 6.97 (t, 1H), 7.03 (s, 1H), 7.19-7.23 (m, 1H); ESI MS m/z 582 (MH)$^+$. Anal. ($C_{28}H_{39}ClF_3N_7O.0.25H_2O$) Calcd: C, 57.33; H, 6.79; N, 16.71. Found: C, 57.38; H, 6.69; N, 16.86.

EXAMPLE 16

N-(4-(4-(2-(tert-Butyl)-6-(trifluoromethyl)pyrimidin-4-yl)piperazin-1-yl)butyl)-4-(4-chlorophenyl)piperidine-1-carboxamide (16). Prepared from 4-(4-(2-(tert-butyl)-6-(trifluoromethyl)pyrimidin-4-yl)piperazin-1-yl)butan-1-amine, CDI and 4-(4-chlorophenyl)piperidine as described in Example 1. Yield: 58%. mp 90-94° C. TLC R$_f$ 0.37 (CHCl$_3$-MeOH, 95:5); $^1$HNMR (DMSO-d$_6$) δ 1.30 (s, 9H), 1.42-1.52 (m, 4H), 1.68-1.74 (m, 4H), 2.62-2.76 (m, 3H), 3.02-3.11 (m, 6H), 3.42-3.34 (m, 4H), 4.02 (d, J=13.3 Hz, 2H), 4.46-4.80 (bs, 2H), 6.58 (t, 1H), 7.21-7.37 (m, 5H); ESI MS m/z 581 (MH)$^+$. Anal. ($C_{29}H_{40}ClF_3N_6O$) Calcd: C, 59.94; H, 6.94; N, 14.62. Found: C, 59.52; H, 6.74; N, 14.52.

EXAMPLE 17

N-(4-(4-(2-(tert-Butyl)-6-(trifluoromethyl)pyrimidin-4-yl)piperazin-1-yl)butyl)-4-cyano-4-phenylpiperidine-1-carboxamide (17). Prepared from 4-(4-(2-(tert-butyl)-6-(trifluoromethyl)pyrimidin-4-yl)piperazin-1-yl)butan-1-amine, CDI and 4-phenylpiperidine-4-carbonitrile as described in Example 1. Yield: 39%. mp 130-132° C. TLC R$_f$ 0.34 (CHCl$_3$-MeOH, 95:5); $^1$HNMR (DMSO-d$_6$) δ 1.28 (s, 9H), 1.45 (bs, 4H), 1.84-1.92 (m, 2H), 2.11-2.14 (m, 2H), 2.31 (t, 2H), 2.43 (t, 4H), 2.92-3.07 (m, 4H), 3.70 (bs, 4H), 4.14-4.29 (m, 2H), 6.62 (t, 1H), 7.03 (s, 1H), 7.34-7.39 (m, 1H), 7.42-7.47 (m, 2H), 7.51-7.55 (m, 2H); ESI MS m/z 572 (MH)$^+$. Anal. ($C_{30}H_{40}F_3N_7O.0.25H_2O$) Calcd: C, 62.54; H, 7.09; N, 17.02. Found: C, 62.47; H, 6.82; N, 16.94.

EXAMPLE 18

N-(4-(4-(2-(tert-Butyl)-6-(trifluoromethyl)pyrimidin-4-yl)piperazin-1-yl)butyl)-4-(2,3-dichlorophenyl)piperazine-1-carboxamide (18). Prepared from 4-(4-(2-(tert-butyl)-6-(trifluoromethyl)pyrimidin-4-yl)piperazin-1-yl)butan-1-amine, CDI and 1-(2,3-dichlorophenyl)piperazine as described in Example 1. Yield: 38%. mp 162-164° C. TLC R$_f$ 0.67 (CHCl$_3$-MeOH, 92.5:7.5); $^1$H NMR (DMSO-d$_6$) δ 1.28 (s, 9H), 1.45 (bs, 4H), 2.31 (bs, 2H), 2.42 (t, 4H), 2.92 (t, 4H), 3.04-3.07 (m, 2H), 3.45 (t, 4H), 3.71 (bs, 4H), 6.55 (t, 1H), 7.03 (s, 1H), 7.10-7.18 (m, 1H), 7.28-7.34 (m, 2H); ESI MS m/z 616 (MH)$^+$. Anal. ($C_{28}H_{38}Cl_2F_3N_7O$) Calcd: C, 54.55; H, 6.21; N, 15.90. Found: C, 54.36; H, 6.05; N, 15.74.

EXAMPLE 19

N-(4-(4-(2-(tert-Butyl)-6-(trifluoromethyl)pyrimidin-4-yl)piperazin-1-yl)butyl)-4-(2-methoxyphenyl)piperazine-1-carboxamide (19). Prepared from 4-(4-(2-(tert-butyl)-6-(trifluoromethyl)pyrimidin-4-yl)piperazin-1-yl)butan-1-amine, CDI and 1-(2-methoxyphenyl)piperazine as described in Example 1. Yield: 29%. mp 58-60° C. TLC R$_f$ 0.61 (CHCl$_3$-

MeOH, 92.5:7.5); $^1$H NMR (DMSO-d$_6$) δ 1.28 (s, 9H), 1.45 (bs, 4H), 2.33 (bs, 2H), 2.44 (bs, 4H), 2.88 (t, 4H), 3.02-3.07 (m, 2H), 3.41 (t, 4H), 3.71 (bs, 4H), 3.78 (s, 3H), 6.51 (t, 1H), 6.84-6.99 (m, 4H), 7.04 (s, 1H); ESI MS m/z 578 (MH)$^+$. Anal. (C$_{29}$H$_{42}$F$_3$N$_7$O$_2$.0.5H$_2$O) Calcd: C, 59.37; H, 7.39; N, 16.71. Found: C, 59.48; H, 7.24; N, 16.75.

EXAMPLE 20

N-(4-(4-(2-(tert-Butyl)-6-(trifluoromethyl)pyrimidin-4-yl)piperazin-1-yl)butyl)-4-(3-methoxyphenyl)piperazine-1-carboxamide (20). Prepared from 4-(4-(2-(tert-butyl)-6-(trifluoromethyl)pyrimidin-4-yl)piperazin-1-yl)butan-1-amine, CDI and 1-(3-methoxyphenyl)piperazine as described in Example 1. Yield: 29%. mp 111-113° C. TLC R$_f$ 0.49 (CHCl$_3$-MeOH, 92.5:7.5); $^1$HNMR (DMSO-d$_6$) δ 1.28 (s, 9H), 1.45 (bs, 4H)), 2.33 (bs, 2H), 2.43 (bs, 4H), 3.02-3.10 (m, 6H), 3.41 (t, 4H), 3.71 (s, 7H), 6.37 (dd, J=8.0, 7.8 Hz, 1H), 6.47 (t, 1H), 6.51-6.58 (m, 2H), 7.03 (s, 1H), 7.07-7.14 (m, 1H); ESI MS m/z 578 (MH)$^+$. Anal. (C$_{29}$H$_{42}$F$_3$N$_7$O$_2$.0.25H$_2$O) Calcd: C, 59.82; H, 7.36; N, 16.84. Found: C, 59.76; H, 7.26; N, 16.96.

EXAMPLE 21

N-(4-(4-(2-(tert-Butyl)-6-(trifluoromethyl)pyrimidin-4-yl)piperazin-1-yl)butyl)-4-(4-methoxyphenyl)piperazine-1-carboxamide (21). Prepared from 4-(4-(2-(tert-butyl)-6-(trifluoromethyl)pyrimidin-4-yl)piperazin-1-yl)butan-1-amine, CDI and 1-(4-methoxyphenyl)piperazine as described in Example 1. Yield: 29%. mp 54-56° C. TLC R$_f$ 0.67 (CHCl$_3$-MeOH, 95:5); $^1$H NMR (DMSO-d$_6$) δ 1.28 (s, 9H), 1.44 (bs, 4H)), 2.31 (bs, 2H), 2.43 (bs, 4H), 2.94 (t, 3H), 3.02-3.07 (m, 3H), 3.42 (t, 4H), 3.68 (s, 3H), 3.71 (bs, 4H), 6.54 (t, 1H) 7.03 (s, 1H), 7.10-7.3 (m, 2H), 7.55-7.63 (m, 1H), 7.77 (dd, J=7.7, 7.5 Hz, 1H); ESI MS m/z 578 (MH)$^+$. Anal. (C$_{29}$H$_{42}$F$_3$N$_7$O$_2$) Calcd: C, 60.30; H, 7.33; N, 16.97. Found: C, 60.50; H, 7.23; N, 16.74.

EXAMPLE 22

N-(4-(4-(2-(tert-Butyl)-6-(trifluoromethyl)pyrimidin-4-yl)piperazin-1-yl)butyl)-4-(m-tolyl)piperazine-1-carboxamide (22). Prepared from 4-(4-(2-(tert-butyl)-6-(trifluoromethyl)pyrimidin-4-yl)piperazin-1-yl)butan-1-amine, CDI and 1-(m-tolyl)piperazine as described in Example 1. Yield: 33%. mp 122-124° C. TLC R$_f$ 0.33 (CHCl$_3$-MeOH, 92.5:7.5); $^1$H NMR (DMSO-d$_6$) δ 1.28 (s, 9H), 1.44 (t, 4H), 2.46 (s, 3H), 2.31 (t, 2H), 2.42 (t, 4H), 3.05 (t, 6H), 3.42 (t, 4H), 3.70 (s, 4H), 6.56 (t, 1H), 6.61-6.63 (m, 1H), 6.73-6.78 (m, 2H), 7.03 (s, 1H), 7.07-7.12 (m, 1H); ESI MS m/z 562 (MH)$^+$. Anal. (C$_{29}$H$_{42}$F$_3$N$_7$O.0.25H$_2$O) Calcd: C, 61.52; H, 7.57; N, 17.37. Found: C, 61.60; H, 7.58; N, 17.34.

EXAMPLE 23

N-(4-(4-(2-(tert-Butyl)-6-(trifluoromethyl)pyrimidin-4-yl)piperazin-1-yl)butyl)-4-(p-tolyl)piperazine-1-carboxamide (23). Prepared from 4-(4-(2-(tert-butyl)-6-(trifluoromethyl)pyrimidin-4-yl)piperazin-1-yl)butan-1-amine, CDI and 1-(p-tolyl)piperazine as described in Example 1. Yield: 35%. mp 116-118° C. TLC R$_f$ 0.60 (CHCl$_3$-MeOH, 92.5:7.5); $^1$H NMR (DMSO-d$_6$) δ 1.28 (s, 9H), 1.44 (bs, 4H)), 2.20 (s, 3H), 2.31 (bs, 2H), 2.42 (t, 4H), 3.00 (t, 4H), 3.04-3.07 (m, 2H), 3.41 (t, 4H), 3.71 (bs, 4H), 6.54 (t, 1H), 6.82-6.89 (m, 2H), 7.01-7.05 (m, 3H); ESI MS m/z 562 (MH)$^+$. Anal. (C$_{29}$H$_{42}$F$_3$N$_7$O) Calcd: C, 62.01; H, 7.54; N, 17.46. Found: C, 61.78; H, 7.31; N, 16.42.

EXAMPLE 24

N-(4-(4-(2-(tert-Butyl)-6-(trifluoromethyl)pyrimidin-4-yl)piperazin-1-yl)butyl)-4-(2,3-dimethylphenyl)piperazine-1-carboxamide (24). Prepared from 4-(4-(2-(tert-butyl)-6-(trifluoromethyl)pyrimidin-4-yl)piperazin-1-yl)butan-1-amine, CDI and 1-(2,3-dimethylphenyl)piperazine as described in Example 1. Yield: 35%. mp 157-159° C. TLC R$_f$ 0.63 (CHCl$_3$-MeOH, 92.5:7.5); $^1$H NMR (DMSO-d$_6$) δ 1.28 (s, 9H), 1.45 (bs, 4H)), 2.17 (s, 3H), 2.21 (s, 3H), 2.32 (bs, 2H), 2.43 (t, 4H), 2.72 (t, 4H), 3.02-3.07 (m, 2H), 3.42 (bs, 4H), 3.71 (bs, 4H), 6.51 (t, 1H), 6.82-6.89 (m, 2H), 7.03-7.05 (m, 2H); ESI MS m/z 576 (MH)$^+$. Anal. (C$_{30}$H$_{44}$F$_3$N$_7$O) Calcd: C, 62.59; H, 7.70; N, 17.03. Found: C, 62.57; H, 7.72; N, 17.90.

EXAMPLE 25

N-(4-(4-(2-(tert-Butyl)-6-(trifluoromethyl)pyrimidin-4-yl)piperazin-1-yl)butyl)-4-(2-cyanophenyl)piperazine-1-carboxamide (25). Prepared from 4-(4-(2-(tert-butyl)-6-(trifluoromethyl)pyrimidin-4-yl)piperazin-1-yl)butan-1-amine, CDI and 1-(2-cyanophenyl)piperazine as described in Example 1. Yield: 32%. mp 61-63° C. TLC R$_f$ 0.61 (CHCl$_3$-MeOH, 92.5:7.5); $^1$H NMR (DMSO-d$_6$) δ 1.28 (s, 9H), 1.45 (bs, 4H), 2.32 (bs, 2H), 2.43 (bs, 4H), 3.04-3.12 (m, 6H), 3.46 (t, 4H), 3.71 (bs, 4H), 6.58 (t, 1H), 7.03 (s, 1H), 7.10-7.30 (m, 2H), 7.55-7.63 (m, 1H), 7.77 (dd, J=7.7, 7.5 Hz, 1H); ESI MS m/z 573 (MH)$^+$. Anal. (C$_{29}$H$_{39}$F$_3$N$_8$O.0.5H$_2$O) Calcd: C, 59.88; H, 6.93; N, 19.26. Found: C, 60.11; H, 6.81; N, 19.35.

EXAMPLE 26

N-(4-(4-(2-(tert-Butyl)-6-(trifluoromethyl)pyrimidin-4-yl)piperazin-1-yl)butyl)-4-(3-cyanophenyl)piperazine-1-carboxamide (26). Prepared from 4-(4-(2-(tert-butyl)-6-(trifluoromethyl)pyrimidin-4-yl)piperazin-1-yl)butan-1-amine, CDI and 1-(3-cyanophenyl)piperazine as described in Example 1. Yield: 30%. mp 84-86° C. TLC R$_f$ 0.44 (CHCl$_3$-MeOH, 92.5:7.5); $^1$H NMR (DMSO-d$_6$) δ 1.28 (s, 9H), 1.46 (bs, 4H), 2.35 (bs, 2H), 2.46 (bs, 4H), 3.05-3.07 (m, 2H), 3.19 (t, 4H), 3.43 (t, 4H), 3.72 (bs, 4H), 6.61 (t, 1H), 7.04 (s, 1H), 7.15-7.18 (m, 1H), 7.27-7.31 (m, 1H), 7.35-7.42 (m, 2H); ESI MS m/z 573 (MH)$^+$. Anal. (C$_{29}$H$_{39}$F$_3$N$_8$O.H$_2$O) Calcd: C, 58.97; H, 6.97; N, 18.97. Found: C, 58.95; H, 6.95; N, 19.05.

EXAMPLE 27

N-(4-(4-(2-(tert-Butyl)-6-(trifluoromethyl)pyrimidin-4-yl)piperazin-1-yl)butyl)-4-(3-(trifluoromethyl)phenyl)piperazine-1-carboxamide (27). Prepared from 4-(4-(2-(tert-butyl)-6-(trifluoromethyl)pyrimidin-4-yl)piperazin-1-yl)butan-1-amine, CDI and 1-(3-(trifluoromethyl)phenyl)piperazine as described in Example 1. Yield: 21%. mp 51-53° C. TLC R$_f$ 0.26 (CHCl$_3$-MeOH, 95:5); $^1$H NMR (DMSO-d$_6$) δ 1.28 (s, 9H), 1.45 (bs, 4H)), 2.32 (bs, 2H), 2.43 (bs, 4H), 3.04-3.07 (m, 2H), 3.19 (t, 4H), 3.44 (t, 4H), 3.71 (bs, 4H), 6.60 (t, 1H), 7.03 (s, 1H), 7.07 (d, J=7.8 Hz, 1H), 7.19 (s, 1H), 7.23 (dd, J=8.2, 8.2 Hz, 1H), 7.40-7.45 (m, 1H); ESI MS m/z 616 (MH)$^+$. Anal. (C$_{29}$H$_{39}$F$_6$N$_7$O—H$_2$O) Calcd: C, 55.76; H, 6.45; N, 15.70, Found: C, 55.70; H, 6.06; N, 15.52.

EXAMPLE 28

N-(4-(4-(2-(tert-Butyl)-6-(trifluoromethyl)pyrimidin-4-yl)piperazin-1-yl)butyl)-4-(4-(trifluoromethyl)phenyl)piperazine-1-carboxamide (28). Prepared from 4-(4-(2-(tert-butyl)-6-(trifluoromethyl)pyrimidin-4-yl)piperazin-1-yl)butan-1-amine, CDI and 1-(4-(trifluoromethyl)phenyl)piperazine as described in Example 1. Yield: 34%. mp 51-53° C. TLC $R_f$ 0.61 (CHCl$_3$-MeOH, 92.5:7.5); $^1$H NMR (DMSO-d$_6$) δ 1.28 (s, 9H), 1.45 (bs, 4H), 2.31 (bs, 2H), 2.42 (t, 4H), 3.04-3.07 (m, 2H), 3.25 (t, 4H), 3.44 (t, 4H), 3.71 (bs, 4H), 6.58 (t, 1H), 7.03 (s, 1H), 7.07 (d, J=8.8 Hz, 2H), 7.49 (d, J=8.8 Hz, 2H); ESI MS m/z 616 (MH)$^+$. Anal. (C$_{29}$H$_{39}$F$_6$N$_7$O) Calcd: C, 56.58; H, 6.39; N, 15.93. Found: C, 56.5; H, 6.30; N, 15.69.

EXAMPLE 29

N-(4-(4-(2-(tert-Butyl)-6-(trifluoromethyl)pyrimidin-4-yl)piperazin-1-yl)butyl)-4-(pyridin-2-yl)piperazine-1-carboxamide (29). Prepared from 4-(4-(2-(tert-butyl)-6-(trifluoromethyl)pyrimidin-4-yl)piperazin-1-yl)butan-1-amine, CDI and 1-(pyridin-2-yl)piperazine as described in Example 1. Yield: 23%. mp 50-52° C. TLC $R_f$ 0.42 (CHCl$_3$-MeOH, 92.5:7.5); $^1$HNMR (DMSO-d$_6$) δ 1.28 (s, 9H), 1.45 (bs, 4H), 2.32 (bs, 2H), 2.43 (bs, 4H), 3.05-3.07 (m, 2H), 3.35-3.47 (m, 8H), 3.71 (bs, 4H), 6.55 (t, 1H), 6.63-6.66 (m, 1H), 6.83-6.85 (m, 1H), 7.03 (s, 1H), 7.51-7.57 (m, 1H), 8.10-8.13 (m, 1H); ESI MS m/z 549 (MH)$^+$. Anal. (C$_{27}$H$_{39}$F$_3$N$_8$O$_2$.0.5H$_2$O) Calcd: C, 58.15; H, 7.23; N, 20.09. Found: C, 558.09; H, 7.12; N, 20.00.

EXAMPLE 30

N-(4-(4-(2-(tert-Butyl)-6-(trifluoromethyl)pyrimidin-4-yl)piperazin-1-yl)butyl)-4-(pyridin-3-yl)piperazine-1-carboxamide (30). Prepared from 4-(4-(2-(tert-butyl)-6-(trifluoromethyl)pyrimidin-4-yl)piperazin-1-yl)butan-1-amine, CDI and 1-(pyridin-3-yl)piperazine as described in Example 1. Yield: 28%. mp 52-55° C. TLC $R_f$ 0.25 (CHCl$_3$-MeOH, 92.5:7.5); $^1$H NMR (DMSO-d$_6$) δ 1.28 (s, 9H), 1.45 (bs, 4H)), 2.31 (t, 2H), 2.42 (t, 4H), 3.03-3.09 (m, 2H), 3.15 (t, 4H), 3.45 (t, 4H), 3.71 (bs, 4H), 6.59 (t, 1H), 7.03 (s, 1H), 7.18-7.23 (m, 1H), 7.32-7.37 (m, 1H), 8.00 (dd, J=5.7, 4.3 Hz, 1H), 8.33 (s, 1H); ESI MS m/z 549 (MH)$^+$. Anal. (C$_{27}$H$_{39}$F$_3$N$_8$O$_2$—H$_2$O) Calcd: C, 57.23; H, 7.29; N, 16.84. Found: C, 57.38; H, 7.14; N, 19.94.

EXAMPLE 31

N-(4-(4-(2-(tert-Butyl)-6-(trifluoromethyl)pyrimidin-4-yl)piperazin-1-yl)butyl)-4-(pyridin-4-yl)piperazine-1-carboxamide (31). Prepared from 4-(4-(2-(tert-butyl)-6-(trifluoromethyl)pyrimidin-4-yl)piperazin-1-yl)butan-1-amine, CDI and 1-(pyridin-4-yl)piperazine as described in Example 1. Yield: 31%. mp 47-48° C. TLC $R_f$ 0.25 (CHCl$_3$-MeOH, 92.5:7.5); $^1$H NMR (DMSO-d$_6$) δ 1.28 (s, 9H), 1.45 (bs, 4H), 2.31 (t, 2H), 2.42 (t, 4H), 3.03-3.08 (m, 2H), 3.28-3.31 (m, 4H), 3.40-3.44 (m, 4H), 3.71 (bs, 4H), 6.58 (t, 1H), 6.81-6.84 (m, 2H), 7.03 (s, 1H), 8.12 (dd, J=5.1, 4.9 Hz, 2H); ESI MS m/z 549 (MH)$^+$. Anal. (C$_{27}$H$_{39}$F$_3$N$_8$O—H$_2$O) Calcd: C, 57.23; H, 7.29; N, 16.84. Found: C, 57.38; H, 7.14; N, 19.94.

EXAMPLE 32

N-(4-(4-(2-(tert-Butyl)-6-(trifluoromethyl)pyrimidin-4-yl)piperazin-1-yl)butyl)-4-(pyrimidin-2-yl)piperazine-1-carboxamide (32). Prepared from 4-(4-(2-(tert-butyl)-6-(trifluoromethyl)pyrimidin-4-yl)piperazin-1-yl)butan-1-amine, CDI and 2-(piperazin-1-yl)pyrimidine as described in Example 1. Yield: 26%. mp 110-112° C. TLC $R_f$ 0.61 (CHCl$_3$-MeOH, 95:5); $^1$H NMR (DMSO-d$_6$) δ 1.28 (s, 9H), 1.45 (bs, 4H)), 2.31 (bs, 2H), 2.44 (t, 4H), 3.02-3.07 (m, 2H), 3.69 (t, 4H), 3.68-3.71 (m, 8H), 6.52 (t, 1H), 6.64 (t, 1H), 7.03 (s, 1H), 8.36 (d, J=4.7 Hz, 2H); ESI MS m/z 550 (MH)$^+$. Anal. (C$_{26}$H$_{38}$F$_3$N$_9$O) Calcd: C, 56.82; H, 6.97; N, 22.94. Found: C, 56.59; H, 6.99; N, 22.67.

EXAMPLE 33

N-(4-(4-(2-(tert-Butyl)-6-(trifluoromethyl)pyrimidin-4-yl)piperazin-1-yl)butyl)-4-(pyrazin-2-yl)piperazine-1-carboxamide (33). Prepared from 4-(4-(2-(tert-butyl)-6-(trifluoromethyl)pyrimidin-4-yl)piperazin-1-yl)butan-1-amine, CDI and 2-(piperazin-1-yl)pyrazine as described in Example 1. Yield: 21%. mp 55-58° C. TLC $R_f$ 0.29 (CHCl$_3$-MeOH, 92.5:7.5); $^1$H NMR (DMSO-d$_6$) δ 1.28 (s, 9H), 1.45 (t, 4H), 2.31 (t, 2H), 2.42 (t, 4H), 3.04-3.07 (bq, 2H), 3.32-3.43 (m, 4H), 3.52-3.55 (m, 4H), 3.71 (bs, 4H), 6.57 (t, 1H), 7.03 (s, 1H), 7.84 (d, J=2.7 Hz, 1H), 8.06-8.09 (m, 1H), 8.33 (d, J=1.6 Hz, 1H); ESI MS m/z 550 (MH)$^+$. Anal. (C$_{26}$H$_{38}$F$_3$N$_9$O.0.5H$_2$O) Calcd: C, 55.90; H, 7.03; N, 22.56. Found: C, 55.93; H, 6.97; N, 22.39.

EXAMPLE 34

N-(4-(4-(2-(tert-Butyl)-6-(trifluoromethyl)pyrimidin-4-yl)piperazin-1-yl)butyl)-4-(quinolin-4-yl)piperazine-1-carboxamide (34). Prepared from 4-(4-(2-(tert-butyl)-6-(trifluoromethyl)pyrimidin-4-yl)piperazin-1-yl)butan-1-amine, CDI and 4-(piperazin-1-yl)quinoline as described in Example 1. Yield: 35%. mp 75-77° C. TLC $R_f$ 0.30 (CHCl$_3$-MeOH, 92.5:7.5); $^1$H NMR (DMSO-d$_6$) δ 1.28 (s, 9H), 1.47 (bs, 4H), 2.37 (bs, 2H), 2.46 (bs, 4H), 3.05-3.08 (m, 2H), 3.13 (t, 4H), 3.59 (t, 4H), 3.73 (bs, 4H), 6.62 (t, 1H), 7.00-7.02 (m, 1H), 7.05 (s, 1H), 7.54-7.58 (m, 1H), 7.67-7.72 (m, 1H), 7.94 (dd, J=8.8, 8.2 Hz, 1H), 8.06 (dd, J=8, 8, 8.3 Hz, 1H), 8.69 (d, J=5.1 Hz, 1H); ESI MS m/z 599 (MH)$^+$. Anal. (C$_{31}$H$_{41}$F$_3$N$_8$O.0.5H$_2$O) Calcd: C, 61.27; H, 6.97; N, 18.44. Found: C, 61.14; H, 6.62; N, 18.44.

EXAMPLE 35

N-(4-(4-(2-(tert-Butyl)-6-(trifluoromethyl)pyrimidin-4-yl)piperazin-1-yl)butyl)-4-cyclopropylpiperazine-1-carboxamide (35). Prepared from 4-(4-(2-(tert-butyl)-6-(trifluoromethyl)pyrimidin-4-yl)piperazin-1-yl)butan-1-amine, CDI and 4-cyclopropylpiperazine as described in Example 1. Yield: 43%. Viscous oil. TLC $R_f$ 0.58 (CHCl$_3$-MeOH, 92.5:7.5); $^1$H NMR (DMSO-d$_6$) δ 0.28-0.32 (m, 2H), 0.38-0.43 (m, 2H), 1.28 (s, 9H), 1.42 (t, 4H), 1.56-1.61 (m, 1H), 2.30 (t, 2H), 2.40-2.50 (m, 8H), 2.99-3.04 (m, 2H), 3.21 (t, 4H), 3.71 (bs, 4H), 6.42 (t, 1H), 7.03 (s, 1H); ESI MS m/z 512 (MH)$^+$. Anal. (C$_{25}$H$_{40}$F$_3$N$_7$O) Calcd: C, 58.69; H, 7.88; N, 19.16. Found: C, 58.47; H, 7.94; N, 18.94.

EXAMPLE 36

4-Benzyl-N-(4-(4-(2-(tert-butyl)-6-(trifluoromethyl)pyrimidin-4-yl)piperazin-1-yl)butyl)piperazine-1-carboxamide (36). Step 1. A solution of CDI (0.65 g, 4.01 mmol), in THF (5 ML) was added to a solution of 4-(4-(2-(tert-butyl)-6-(trifluoromethyl)pyrimidin-4-yl)piperazin-1-yl)butan-1-amine (1.44 g, 4.01 mmol). The mixture was stirred overnight at room temperature. To the mixture was then added 1-t-BOC-piperazine (0.746 g, 4.01 mmol) and the mixture was heated under reflux overnight. The mixture was concentrated under reduced pressure, the residue was dissolved in EtOAc, washed with aqueous sodium bicarbonate and brine and organic extracts were dried over anhydrous sodium sulfate. Removal of the solvent and purification of the crude produce over a column of silica gel using EtOAc-MeOH (10:1) gave tert-butyl 4-((4-(4-(2-(tert-butyl)-6-(trifluoromethyl)pyrimidin-4-yl)piperazin-1-yl)butyl)carbamoyl)piperazine-1-carboxylate (26088, K797-148) as a viscous liquid. Yield 1.01 g (44%)). TLC $R_f$ 0.60 (CHCl$_3$-MeOH, 90:10); $^1$H NMR (DMSO-d$_6$) δ 1.28 (s, 9H), 1.40 (s, 9H), 1.43 (t, 4H), 2.30 (t, 2H), 2.42 (t, 4H), 3.03 (bq, 2H), 3.26 (bs, 8H), 3.71 (bs, 4H), 6.51 (t, 1H), 7.03 (s, 1H); ESI MS m/z 572 (MH)$^+$. Anal. (C$_{27}$H$_{44}$F$_3$N$_7$O$_3$) Calcd: C, 56.73; H, 7.76; N, 17.15. Found: C, 56.48; H, 7.98; N, 17.14.

Step 2. The compound obtained above (1.01 g, 1.77 mmol) was dissolved in 12 mL of TFA-CH$_2$Cl$_2$ (1:1) and the solution was stirred at room temperature overnight. Volatiles were removed under reduced pressure and the residue was partitioned between EtOAc and saturated aqueous NaHCO$_3$. The layers were separated and the organic layer was washed with brine, dried over anhydrous sodium sulfate, filtered and the solvent was removed under reduced pressure. The crude product thus obtained was purified by chromatography over a column of silica gel using EtOAc-MeOH (90:10) as the eluent to obtain 0.56 g (67%) of N-(4-(4-(2-(tert-butyl)-6-(trifluoromethyl)pyrimidin-4-yl)piperazin-1-yl)butyl)piperazine-1-carboxamide. ESI MS m/z 472 (MH)$^+$.

Step 3. The above product (0.40, 0.84 mmol) was dissolved in methanol (6 mL), and treated with acetic acid (0.1 mL) followed by benzaldehyde (0.82 g, 0.84 mmol). The mixture was stirred at room temperature for 2.5 hours. Sodium cyanoborohydride (0.416 g, 6.72 mmol) was added and the mixture was stirred at room temperature overnight. The reaction mixture was quenched by addition of ice cold water, extracted with CHCl$_3$, and the extracts were washed with brine. The organic layer was dried over anhydrous sodium sulfate, filtered and the filtrate was concentrated under reduced pressure. The residue was purified over a column of silica using EtOAc-MeOH (88:12) as the eluent to obtain the desired product (0.17 g, 36%). mp 132-134° C. TLC $R_f$ 0.45 (CHCl$_3$-MeOH, 90:10); $^1$H NMR (DMSO-d$_6$) δ 1.28 (s, 9H), 1.41 (t, 4H), 2.29 (t, 6H), 2.43 (t, 4H), 3.02 (t, 2H), 3.27 (t, 4H), 3.47 (s, 2H), 3.71 (bs, 4H), 7.02 (s, 1H), 7.23-7.35 (m, 5H), 8.4-9.6 (broad hump, 1H); ESI MS m/z 562 (MH)$^+$. Anal. (C$_{29}$H$_{42}$F$_3$N$_7$O.5H$_2$O) Calcd: C, 61.03; H, 7.60; N, 17.18. Found: C, 61.04; H, 7.46; N, 17.17.

EXAMPLE 37

4-Benzoyl-N-(4-(4-(2-(tert-butyl)-6-(trifluoromethyl)pyrimidin-4-yl)piperazin-1-yl)butyl)piperazine-1-carboxamide (37). Prepared from 4-(4-(2-(tert-butyl)-6-(trifluoromethyl)pyrimidin-4-yl)piperazin-1-yl)butan-1-amine, CDI and 1-benzoylpiperazine as described in Example 1. Yield: 27%. mp 149-150° C. TLC $R_f$ 0.44 (CHCl$_3$-MeOH, 92.5:7.5); $^1$H NMR (DMSO-d$_6$) δ 1.28 (s, 9H), 1.43 (bs, 4H), 2.30 (bs, 2H), 2.42 (t, 4H), 3.03-3.06 (m, 2H), 3.2-3.76 (broad hump, 12H), 6.54 (t, 1H), 7.03 (s, 1H), 7.32-7.48 (m, 5H); ESI MS m/z 576 (MH)$^+$. Anal. (C$_{29}$H$_{40}$F$_3$N$_7$O$_2$.0.25H$_2$O) Calcd: C, 60.29; H, 7.23; N, 16.97. Found: C, 60.47; H, 6.69; N, 16.92.

EXAMPLE 38

N-(4-(4-(2-(tert-Butyl)-6-(trifluoromethyl)pyrimidin-4-yl)piperazin-1-yl)butyl)-3-(pyridin-4-yl)azetidine-1-carboxamide (38). Prepared from 4-(4-(2-(tert-butyl)-6-(trifluoromethyl)pyrimidin-4-yl)piperazin-1-yl)butan-1-amine, CDI and 4-(azetidin-3-yl)pyridine hydrochloride as described in Example 1. Yield: 30%. mp 43-46° C. TLC $R_f$ 0.35 (CHCl$_3$-MeOH, 95:5); $^1$H NMR (DMSO-d$_6$) δ 1.28 (s, 9H), 1.37 (bs, 4H), 2.31 (t, 2H), 2.42 (t, 4H), 2.98-3.04 (m, 2H), 3.71 (bs, 4H), 3.74-3.81 (m, 3H), 4.16-4.22 (m, 2H), 6.38 (t, 1H), 7.04 (s, 1H), 7.34 (dd, J=4.3, 4.1 Hz, 2H), 8.52 (dd, J=4.3, 4.3 Hz, 2H); ESI MS m/z 520 (MH)$^+$. Anal. (C$_{26}$H$_{36}$F$_3$N$_7$O.0.5H$_2$O) Calcd: C, 58.09; H, 7.12; N, 18.24. Found: C, 58.15; H, 7.00; N, 18.05.

EXAMPLE 39

N-(4-(4-(2-(tert-Butyl)-6-(trifluoromethyl)pyrimidin-4-yl)piperazin-1-yl)butyl)isoindoline-2-carboxamide (39). Prepared from 4-(4-(2-(tert-butyl)-6-(trifluoromethyl)pyrimidin-4-yl)piperazin-1-yl)butan-1-amine, CDI and isoindoline as described in Example 1. Yield: 28%. mp 47-48° C. TLC $R_f$ 0.25 (CHCl$_3$-MeOH, 92.5:7.5); $^1$H NMR (DMSO-d$_6$) δ 1.28 (s, 9H), 1.48 (bs, 4H), 2.31-2.38 (m, 2H), 2.43 (t, 4H), 3.09-3.11 (m, 2H), 3.71 (bs, 4H), 4.57 (s, 4H), 6.31 (bs, 1H), 7.04 (bs, 1H), 7.26-7.34 (m, 4H); ESI MS m/z 505 (MH)$^+$. Anal. (C$_{26}$H$_{35}$F$_3$N$_6$O.0.5H$_2$O) Calcd: C, 60.80; H, 7.07; N, 16.36. Found: C, 60.69; H, 6.89; N, 16.16.

EXAMPLE 40

N-(4-(4-(2-(tert-Butyl)-6-(trifluoromethyl)pyrimidin-4-yl)piperazin-1-yl)butyl)-5-methoxyisoindoline-2-carboxamide (40). Prepared from 4-(4-(2-(tert-butyl)-6-(trifluoromethyl)pyrimidin-4-yl)piperazin-1-yl)butan-1-amine, CDI and 5-methoxyisoindoline as described in Example 1. Yield: 43%. mp 58-62° C. TLC $R_f$ 0.48 (CHCl$_3$-MeOH, 92.5:7.5); $^1$H NMR (DMSO-d$_6$) δ 1.28 (s, 9H), 1.47 (bs, 4H), 2.34 (t, 2H), 2.43 (t, 4H), 3.08 (bq, 2H), 3.71 (bs, 4H), 3.74 (s, 3H), 4.49 (s, 2H), 4.53 (s, 2H), 6.28 (t, 1H), 6.82 (dd, J=8.6, 8.2 Hz, 1H), 6.88 (d, J=2.4 Hz, 1H), 7.03 (s, 1H), 7.20 (d, J=8.2 Hz, 1H), ESI MS m/z 535 (MH)$^+$. Anal. (C$_{27}$H$_{37}$F$_3$N$_6$O$_2$.0.25H$_2$O) Calcd: C, 60.15; H, 7.01; N, 15.59. Found: C, 60.07; H, 6.75; N, 15.31.

EXAMPLE 41

N-(4-(4-(2-(tert-Butyl)-6-(trifluoromethyl)pyrimidin-4-yl)piperazin-1-yl)butyl)-3,4-dihydroisoquinoline-2(1H)-carboxamide (41). Prepared from 4-(4-(2-(tert-butyl)-6-(trifluoromethyl)pyrimidin-4-yl)piperazin-1-yl)butan-1-amine, CDI and 1,2,3,4-tetrahydroisoquinoline as described in Example 1. Yield: 31%. mp 49-51° C. TLC $R_f$ 0.25 (CHCl$_3$-MeOH, 92.5:7.5); $^1$H NMR (DMSO-d$_6$) δ 1.28 (s, 9H), 1.45 (bs, 4H), 2.31 (bs, 2H), 2.40 (t, 4H), 2.76 (t, 2H), 3.04-3.09 (m, 2H), 3.54 (t, 2H), 3.69 (bs, 4H), 4.48 (s, 2H), 6.53 (bs, 1H), 7.03 (bs, 1H), 7.10-7.18 (m, 4H); ESI MS m/z 519 (MH)$^+$. Anal. (C$_{27}$H$_{37}$F$_3$N$_6$O.0.25H$_2$O) Calcd: C, 61.99; H, 7.22; N, 16.07. Found: C, 61.84; H, 6.92; N, 15.99.

EXAMPLE 42

N-(4-(4-(2-(tert-Butyl)-6-(trifluoromethyl)pyrimidin-4-yl)piperazin-1-yl)butyl)-4,5-dihydro-1H-benzo[d]azepine-3(2H)-carboxamide (42). Prepared from 4-(4-(2-(tert-butyl)-6-(trifluoromethyl)pyrimidin-4-yl)piperazin-1-yl)butan-1-amine, CDI and 2,3,4,5-tetrahydro-1H-benzo[d]azepine as described in Example 1. Yield: 21%. mp 56-58° C. TLC $R_f$ 0.33 (CHCl$_3$-MeOH, 95:5); $^1$H NMR (DMSO-d$_6$) δ 1.28 (s, 9H), 1.43 (bs, 4H), 2.31 (bs, 2H), 2.41 (t, 4H), 2.77-2.82 (m, 4H), 3.07-3.09 (m, 2H), 3.43-3.47 (m, 2H), 3.70 (bs, 4H), 6.51 (t, 3H), 7.03 (s, 1H), 7.07-7.14 (m, 4H); ESI MS m/z 533 (MH)+. Anal. ($C_{28}H_{39}F_3N_6O.0.25H_2O$) Calcd: C, 62.61; H, 7.41; N, 15.65. Found: C, 62.60; H, 7.21; N, 15.47.

EXAMPLE 43

4-([1,1'-Biphenyl]-2-yl)-N-(4-(4-(2-(tert-butyl)-6-(trifluoromethyl)pyrimidin-4-yl)piperazin-1-yl)butyl)piperazine-1-carboxamide (43). Prepared from 4-(4-(2-(tert-butyl)-6-(trifluoromethyl)pyrimidin-4-yl)piperazin-1-yl)butan-1-amine, CDI and 1-([1,1'-biphenyl]-2-yl)piperazine as described in Example 1. Yield: 28%. mp 84-86° C. TLC $R_f$ 0.33 (CHCl$_3$-MeOH, 95:5); $^1$HNMR (DMSO-d$_6$) δ 1.28 (s, 9H), 1.40-46 (bs, 4H), 2.38-2.43 (bs, 6H), 2.69 (t, 4H), 2.95-3.01 (m, 2H), 3.17 (t, 4H), 3.62-3.72 (bs, 4H), 6.42 (bs, 1H), 7.02-7.11 (m, 3H), 7.2 (dd, J=2.0, 1.6 Hz, 1H), 7.27-7.41 (m, 2H), 7.40-7.44 (m, 2H), 7.61-7.64 (m, 2H); ESI MS m/z 624 (MH)+. Anal. ($C_{34}H_{44}F_3N_7O.0.75H_2O$) Calcd: C, 64.08; H, 7.20; N, 15.39. Found: C, 63.94; H, 6.99; N, 15.47.

EXAMPLE 44

4-([1,1'-Biphenyl]-3-yl)-N-(4-(4-(2-(tert-butyl)-6-(trifluoromethyl)pyrimidin-4-yl)piperazin-1-yl)butyl)piperazine-1-carboxamide (44). Prepared from 4-(4-(2-(tert-butyl)-6-(trifluoromethyl)pyrimidin-4-yl)piperazin-1-yl)butan-1-amine, CDI and 1-([1,1'-biphenyl]-3-yl)piperazine as described in Example 1. Yield: 18%. mp 62-66° C. TLC $R_f$ 0.31 (CHCl$_3$-MeOH, 95:5); $^1$H NMR (DMSO-d$_6$) δ 1.28 (s, 9H), 1.44-46 (m, 4H), 2.38 (bs, 2H), 2.51-2.56 (m, 2H), 3.04-3.09 (m, 2H), 3.17 (t, 4H), 3.46 (t, 4H), 3.62-3.72 (bs, 4H), 6.62 (t, 1H), 6.96 (dd, J=8.2, 8.2 Hz, 1H), 7.02 (s, 1H), 7.07 (d, J=7.5 Hz, 1H), 7.14-7.18 (m, 1H), 7.30-7.37 (m, 4H), 7.44-7.46 (m, 2H), 7.62-7.66 (m, 2H); ESI MS m/z 624 (MH)+. Anal. ($C_{34}H_{44}F_3N_7O.0.5H_2O$) Calcd: C, 64.54; H, 7.17; N, 15.50. Found: C, 64.14; H, 6.91; N, 15.42.

EXAMPLE 45

4-([1,1'-Biphenyl]-4-yl)-N-(4-(4-(2-(tert-butyl)-6-(trifluoromethyl)pyrimidin-4-yl)piperazin-1-yl)butyl)piperazine-1-carboxamide (45). Prepared from 4-(4-(2-(tert-butyl)-6-(trifluoromethyl)pyrimidin-4-yl)piperazin-1-yl)butan-1-amine, CDI and 1-([1,1'-biphenyl]-4-yl)piperazine as described in Example 1. Yield: 23%. mp 84-86° C. TLC $R_f$ 0.35 (CHCl$_3$-MeOH, 95:5); $^1$H NMR (DMSO-d$_6$) δ 1.28 (s, 9H), 1.46 (bs, 4H)), 2.31-2.47 (m, 6H), 3.02-3.10 (m, 2H), 3.15 (t, 4H), 3.45 (t, 4H), 3.37-3.78 (bs, 4H), 6.59 (bs, 1H), 7.02-7.06 (m, 3H), 7.24-7.30 (m, 1H), 7.37-7.45 (m, 2H), 7.55-7.61 (m, 4H); ESI MS m/z 624 (MH)+. Anal. ($C_{34}H_{44}F_3N_7O.0.75H_2O$) Calcd: C, 64.08; H, 7.2; N, 15.39. Found: C, 63.95; H, 6.94; N, 15.33.

EXAMPLE 46

N-(4-(4-(2-(tert-Butyl)-6-methylpyrimidin-4-yl)piperazin-1-yl)butyl)-4-(phenylsulfonyl)piperazine-1-carboxamide (46). Prepared from 4-(4-(2-(tert-butyl)-6-methylpyrimidin-4-yl)piperazin-1-yl)butan-1-amine, CDI and 1-(phenylsulfonyl)piperazine as described in Example 1. Yield: 40%. mp 139-142° C. TLC $R_f$ 0.33 (CHCl$_3$-MeOH, 95:5); $^1$H NMR (DMSO-d$_6$) δ 1.25 (s, 9H), 1.44 (t, 4H), 2.37 (s, 3H), 2.16-2.28 (m, 2H), 2.35 (t, 4H), 2.82 (t, 4H), 2.94-2.97 (bq, 2H), 3.38 (t, 4H), 3.54 (t, 4H), 6.46 (s, 1H), 6.50 (t, 1H), 7.63-7.56 (m, 5H); ESI MS m/z 558 (MH)+. Anal. ($C_{28}H_{43}N_7O_3S.H_2O$) C, 58.78; H, 7.88; N, 17.03. Found: C, 58.85; H, 7.75; N, 17.05.

EXAMPLE 47

N-(4-(4-(2,3-Dichlorophenyl)piperazin-1-yl)butyl)-4-phenylpiperidine-1-carboxamide (47). Prepared from 4-(4-(2,3-dichlorophenyl)piperazin-1-yl)butan-1-amine, CDI and 4-phenylpiperidine as described in Example 1. Yield: 7%. mp 152-154° C. TLC $R_f$ 0.26 (CHCl$_3$-MeOH, 95:5); $^1$HNMR (DMSO-d$_6$) δ 1.36-1.81 (m, 8H), 2.81-2.58 (m, 3H), 2.99-3.69 (m, 12H), 4.08 (d, J=13.51 Hz, 2H), 6.65 (t, 1H), 7.73-7.43 (m, 8H); ESI MS m/z 489 (MH)+. The free base was dissolved in MeOH and treated with hydrogen chooride in ether to obtain the hydrochloride salt. Anal. ($C_{26}H_{34}Cl_2N_4O.HCl.H_2O$) Calcd: C, 57.41; H, 6.85; N, 10.30. Found: C, 51.35; H, 6.51; N, 10.47.

EXAMPLE 48

N-(4-(4-(2-(tert-Butyl)-6-(trifluoromethyl)pyrimidin-4-yl)piperazin-1-yl)butyl)-4-phenylpiperidine-1-carboxamide (48). Prepared from 4-(4-(2-(tert-butyl)-6-(trifluoromethyl)pyrimidin-4-yl)piperazin-1-yl)butan-1-amine, CDI and 4-phenylpiperidine as described in Example 1. Yield: 48%. mp 156-158° C. TLC $R_f$ 0.46 (CHCl$_3$-MeOH, 90:10); $^1$H NMR (DMSO-d$_6$) δ 1.28 (s, 9H), 1.44 (bs, 4H), 1.48-1.52 (m, 2H), 1.70-1.74 (m, 2H), 2.31 (t, 2H), 2.41 (t, 4H), 2.63-2.76 (m, 3H), 3.04-3.09 (bq, 2H), 3.71 (bs, 4H), 4.07-4.10 (m, 2H), 6.47 (t, 1H), 7.03 (s, 1H), 7.15-7.31 (m, 5H); ESI MS m/z 547 (MH)+. Anal. ($C_{29}H_{41}F_3N_6O$) Calcd: C, 63.72; H, 7.56; N, 15.36. Found: C, 63.78; H, 7.45; N, 15.31.

EXAMPLE 49

N-(4-(4-(2-(tert-Butyl)-6-(trifluoromethyl)pyrimidin-4-yl)piperazin-1-yl)butyl)-4-hydroxy-4-phenylpiperidine-1-carboxamide (49). Prepared from 4-(4-(2-(tert-butyl)-6-(trifluoromethyl)pyrimidin-4-yl)piperazin-1-yl)butan-1-amine, CDI and 4-phenylpiperidin-4-ol as described in Example 1. Yield: 22%. mp 73-75° C. TLC $R_f$ 0.23 (CHCl$_3$-MeOH, 95:5); $^1$H NMR (DMSO-d$_6$) δ 1.28 (s, 9H), 1.41-1.48 (m, 4H), 1.51-1.57 (m, 2H), 1.71-1.81 (m, 2H), 2.31 (t, 2H), 2.42 (t, 4H), 3.02-3.13 (m, 4H), 3.71 (bs, 4H), 3.81 (d, J=13.0 Hz, 2H), 4.99 (s, 1H), 6.43 (t, 1H), 7.02-7.05 (m, 1H), 7.11-7.20 (m, 1H), 7.22-7.33 (m, 2H), 7.44-7.48 (m, 2H); ESI MS m/z 563 (MH)+. Anal. ($C_{29}H_{41}F_3N_6O_2.0.25H_2O$) Calcd: C, 61.41; H, 7.38; N, 14.82; Found: C, 61.44; H, 7.33; N, 14.74.

EXAMPLE 50

4-Benzyl-N-(4-(4-(2-(tert-butyl)-6-(trifluoromethyl)pyrimidin-4-yl)piperazin-1-yl)butyl)piperidine-1-carboxamide (50). Prepared from 4-(4-(2-(tert-butyl)-6-(trifluoromethyl)pyrimidin-4-yl)piperazin-1-yl)butan-1-amine, CDI and 4-benzylpiperidine as described in Example 1. Yield: 53%. mp 74-76° C. TLC $R_f$ 0.60 (CHCl$_3$-MeOH, 95:5); $^1$H NMR (DMSO-d$_6$) δ 0.94-1.06 (m, 1H), 1.28 (s, 9H), 1.41 (t, 4H), 1.48-1.52 (m, 1H), 1.61-1.68 (m, 1H), 2.29 (t, 2H), 2.41 (t, 4H), 2.47-2.50 (m, 2H), 2.51-2.59 (m, 4H), 3.01-3.09 (bq, 2H), 3.71 (bs, 4H), 3.89-3.92 (m, 2H), 6.37 (t, 1H), 7.01 (s, 1H), 7.15-7.19 (m, 3H), 7.25-7.29 (m, 2H); ESI MS m/z 561 (MH)+. Anal. ($C_{30}H_{43}F_3N_6O$) Calcd: C, 64.26; H, 7.73; N, 14.99. Found: C, 64.31; H, 7.63; N, 17.86.

EXAMPLE 51

N-(4-(4-(2-(tert-Butyl)-6-(trifluoromethyl)pyrimidin-4-yl)piperazin-1-yl)butyl)-4-phenoxypiperidine-1-carboxamide (51). Prepared from 4-(4-(2-(tert-butyl)-6-(trifluoromethyl)pyrimidin-4-yl)piperazin-1-yl)butan-1-amine, CDI and 4-phenoxypiperidine as described in Example 1. Yield: 32%. mp 167-169° C. TLC $R_f$ 0.42 (CHCl$_3$-MeOH, 92.5:7.5); $^1$H NMR (DMSO-d$_6$) δ 1.28 (s, 9H), 1.44 (bs, 4H), 1.38-1.91 (m, 4H), 2.31 (t, 2H), 2.42 (t, 4H), 3.06-3.12 (m, 10H), 4.48-4.56 (m, 1H), 6.49 (t, 1H), 6.88-6.97 (m, 3H), 7.03 (s, 1H), 7.24-7.29 (m, 2H); ESI MS m/z 563 (MH)$^+$. Anal. (C$_{29}$H$_{41}$F$_3$N$_6$O$_2$.0.25H$_2$O) Calcd: C, 61.41; H, 7.38; N, 14.82; Found: C, 61.21; H, 7.09; N, 14.69.

EXAMPLE 52

N-(4-(4-(2-(tert-Butyl)-6-methylpyrimidin-4-yl)piperazin-1-yl)butyl)-4-(2-oxo-2,3-dihydro-1H-benzo[d]imidazol-1-yl)piperidine-1-carboxamide (52). Prepared from 4-(4-(2-(tert-butyl)-6-methylpyrimidin-4-yl)piperazin-1-yl)butan-1-amine, CDI and 1-(piperidin-4-yl)-1H-benzo[d]imidazol-2(3H)-one as described in Example 1. Yield: 31%. mp 118-120° C. TLC $R_f$ 0.19 (CHCl$_3$-MeOH, 95:5); $^1$H NMR (DMSO-d$_6$) δ 1.25 (s, 9H), 1.46 (bs, 4H), 1.60-1.68 (m, 2H), 2.11-2.20 (m, 2H), 2.24 (s, 3H), 2.33 (bs, 2H), 2.67 (bs, 4H), 2.72-2.83 (m, 2H), 3.05-3.09 (m, 2H), 3.57 (bs, 4H), 4.1 (d, J=13.7 Hz, 2H), 4.22-4.39 (m, 1H), 6.46 (bs, 1H), 6.54 (m, 1H), 6.93-7.01 (m, 3H), 7.11-7.14 (m, 1H), 10.8 (s, 1H); ESI MS m/z 549 (MH)$^+$. Anal. (C$_{30}$H$_{44}$N$_8$O$_2$.H$_2$O) Calcd: C, 63.58; H, 8.18; N, 19.77. Found: C, 63.38; H, 7.89; N, 19.65.

EXAMPLE 53

N-(4-(4-(2-(tert-Butyl)-6-(trifluoromethyl)pyrimidin-4-yl)piperazin-1-yl)butyl)-4-(2-oxo-2,3-dihydro-1H-benzo[d]imidazol-1-yl)piperidine-1-carboxamide (53). Prepared from 4-(4-(2-(tert-butyl)-6-(trifluoromethyl)pyrimidin-4-yl)piperazin-1-yl)butan-1-amine, CDI and 1-(piperidin-4-yl)-1H-benzo[d]imidazol-2(3H)-one as described in Example 1. Yield: 26%. mp 100-104° C. TLC $R_f$ 0.33 (CHCl$_3$-MeOH, 95:5); $^1$H NMR (DMSO-d$_6$) δ 1.28 (s, 9H), 1.43 (bs, 4H), 1.62-1.68 (m, 2H), 2.10-2.24 (m, 2H), 2.33 (bs, 2H), 2.44 (bs, 4H), 2.74-2.83 (m, 2H), 3.01-311 (m, 2H), 3.71 (bs, 4H), 4.11 (d, J=13.3 Hz, 2H), 4.19-4.36 (m, 1H), 6.55 (t, 1H), 6.92-7.01 (m, 3H), 7.04 (s, 1H), 7.11-7.16 (m, 1H), 10.80 (s, 1H); ESI MS m/z 603 (MH)$^+$. Anal. (C$_{30}$H$_{41}$F$_3$N$_8$O$_2$.0.5H$_2$O) Calcd: C, 58.91; H, 6.92; N, 18.32. Found: C, 58.93; H, 6.75; N, 18.32.

EXAMPLE 54

N-(4-(4-(2-(tert-Butyl)-6-(trifluoromethyl)pyrimidin-4-yl)piperazin-1-yl)butyl)-8-cyano-3,4-dihydro-1H-pyrido[4,3-b]indole-2(5H)-carboxamide (54). Prepared from 4-(4-(2-(tert-butyl)-6-(trifluoromethyl)pyrimidin-4-yl)piperazin-1-yl)butan-1-amine, CDI and 2,3,4,5-tetrahydro-1H-pyrido[4,3-b]indole-8-carbonitrile as described in Example 1. Yield: 21%. mp 100-104° C. TLC $R_f$ 0.47 (CHCl$_3$-MeOH, 95:5); $^1$H NMR (DMSO-d$_6$) δ 1.27 (s, 9H), 1.45 (bs, 6H), 2.30 (t, 2H), 2.78 (t, 2H), 3.06-3.09 (m, 2H), 3.70 (t, 8H), 4.53 (s, 2H), 6.58 (t, 1H), 7.02 (s, 1H), 7.37 (dd, J=8.6, 8.5 Hz, 1H), 7.44-7.47 (m, 1H), 7.80 (d, J=1.2 Hz, 1H), 11.51 (s, 1H); ESI MS m/z 583 (MH)$^+$. Anal. (C$_{30}$H$_{37}$F$_3$N$_8$O.H$_2$O) Calcd: C, 59.99; H, 6.54; N, 18.65; Found: C, 60.38; H, 6.31; N, 17.98.

EXAMPLE 55

N-(4-(4-(2-(tert-Butyl)-6-(trifluoromethyl)pyrimidin-4-yl)piperazin-1-yl)butyl)-1,3,4,9-tetrahydro-2H-pyrido[3,4-b]indole-2-carboxamide (55). Prepared from 4-(4-(2-(tert-butyl)-6-(trifluoromethyl)pyrimidin-4-yl)piperazin-1-yl)butan-1-amine, CDI and 2,3,4,9-tetrahydro-1H-pyrido[3,4-b]indole as described in Example 1. Yield: 36%. mp 110-112° C. TLC $R_f$ 0.17 (CHCl$_3$-MeOH, 95:5); $^1$H NMR (DMSO-d$_6$) δ 1.28 (s, 9H), 1.45 (bs, 4H)), 2.31-2.47 (m, 6H), 2.69 (t, 2H), 3.02-3.10 (m, 2H), 3.60-3.76 (m, 6H), 4.54 (s, 2H), 6.69 (t, 1H), 6.92-6.98 (m, 1H), 7.00-7.06 (m, 2H), 7.27-7.31 (m, 1H), 7.37 (d, J=7.8 Hz 1H), 10.81 (s, 1H); ESI MS m/z 558 (MH)$^+$. Anal. (C$_{29}$H$_{38}$F$_3$N$_7$O.0.5H$_2$O) Calcd: C, 61.47; H, 6.94; N, 17.30. Found: C, 61.30; H, 6.66; N, 17.14.

EXAMPLE 56

N-(4-(4-(2,6-Di-tert-butylpyrimidin-4-yl)piperazin-1yl)butyl)-1,3,4,9-tetrahydro-2H-pyrido[3,4-b]indole-2-carboxamide (56). Prepared from 4-(4-(2,6-di-tert-butylpyrimidin-4-yl)piperazin-1-yl)butan-1-amine, CDI and 2,3,4,9-tetrahydro-1H-pyrido[3,4-b]indole as described in Example 1. Yield: 29%. mp 238-240° C. TLC $R_f$ 0.49 (CHCl$_3$-MeOH, 92.5:7.5); $^1$H NMR (DMSO-d$_6$) δ 1.23 (s, 9H), 1.27 (s, 9H), 1.44 (bs, 4H), 2.29 (t, 2H), 2.38 (t, 4H), 2.66 (t, 2H), 3.04-3.09 (m, 2H), 3.56 (t, 4H), 3.65 (t, 2H), 4.54 (s, 2H), 6.43 (s, 1H), 6.66 (t, 1H), 6.91-7.04 (m, 2H), 7.28 (d, J=8.3 Hz, 1H), 7.37 (d, J=7.8 Hz, 1H), 10.4 (s, 1H); ESI MS m/z 546 (MH)$^+$. Anal. (C$_{32}$H$_{47}$N$_7$O) Calcd: C, 69.28; H, 8.72; N, 17.67. Found: C, 69.42; H, 8.36; N, 17.63.

EXAMPLE 57

N-(4-(4-(2-(tert-Butyl)-6-(trifluoromethyl)pyrimidin-4-yl)piperazin-1-yl)butyl)-4-(4-chlorophenyl)piperazine-1-carboxamide (57). Prepared from 4-(4-(2-(tert-butyl)-6-(trifluoromethyl)pyrimidin-4-yl)piperazin-1-yl)butan-1-amine, CDI and 1-(4-chlorophenyl)piperazine as described in Example 1. Yield: 38%. mp 130-132° C. TLC $R_f$ 0.47 (CHCl$_3$-MeOH, 92.5:7.5); $^1$H NMR (DMSO-d$_6$) δ 1.28 (s, 9H), 1.45 (bs, 4H), 2.31 (t, 2H), 2.42 (t, 4H), 3.04-3.10 (m, 6H), 3.42 (t, 4H), 3.71 (bs, 4H), 6.57 (t, 1H), 6.94-7.04 (m, 2H), 7.03 (s, 1H), 7.22-7.26 (m, 2H); ESI MS m/z 582 (MH)$^+$. Anal. (C$_{28}$H$_{39}$ClF$_3$N$_7$O) Calcd: C, 57.77; H, 6.75; N, 16.84. Found: C, 57.68; H, 6.46; N, 16.73.

EXAMPLE 58

N-(4-(4-(2-(tert-Butyl)-6-(trifluoromethyl)pyrimidin-4-yl)piperazin-1-yl)butyl)-4-(o-tolyl)piperazine-1-carboxamide (58). Prepared from 4-(4-(2-(tert-butyl)-6-(trifluoromethyl)pyrimidin-4-yl)piperazin-1-yl)butan-1-amine, CDI and 1-(o-tolyl)piperazine as described in Example 1. Yield: 30%. mp 158-159° C. TLC $R_f$ 0.44 (CHCl$_3$-MeOH, 92.5:7.5); $^1$H NMR (DMSO-d$_6$) δ 1.28 (s, 9H), 1.45 (bs, 4H), 2.26 (s, 3H), 2.32 (t, 2H), 2.43 (t, 4H), 2.76 (t, 4H), 3.05 (bq, 2H), 3.42 (t, 4H), 3.70 (bs, 4H), 6.54 (t, 1H), 6.94-7.03 (m, 3H), 7.11-7.18 (m, 2H), ESI MS m/z 562 (MH)$^+$. Anal. (C$_{29}$H$_{42}$F$_3$N$_7$O) Calcd: C, 62.01; H, 7.54; N, 17.46. Found: C, 61.85; H, 7.50; N, 17.44.

EXAMPLE 59

N-(4-(4-(2-(tert-Butyl)-6-(trifluoromethyl)pyrimidin-4-yl)piperazin-1-yl)butyl)-4-(4-cyanophenyl)piperazine-1-carboxamide (59). Prepared from 4-(4-(2-(tert-butyl)-6-(trifluoromethyl)pyrimidin-4-yl)piperazin-1-yl)butan-1-amine, CDI and 1-(4-cyanophenyl)piperazine as described in Example 1. Yield: 26%. mp 67-69° C. TLC $R_f$ 0.50 (CHCl$_3$-

MeOH, 92.5:7.5); $^1$H NMR (DMSO-$d_6$) δ 1.28 (s, 9H), 1.45 (bs, 4H), 2.31 (t, 2H), 2.42 (bs, 4H), 3.06 (bs, 2H), 3.22-3.38 (m, 8H), 3.71 (bs, 4H), 6.58 (t, 1H), 6.99-7.04 (m, 3H), 7.57 (d, J=8.2 Hz, 2H), ESI MS m/z 573 (MH)$^+$. Anal. ($C_{29}H_{39}F_3N_8O$) Calcd: C, 60.82; H, 6.86; N, 19.57. Found: C, 60.63; H, 6.63; N, 19.22.

EXAMPLE 60

N-(4-(4-(2-(tert-Butyl)-6-(trifluoromethyl)pyrimidin-4-yl)piperazin-1-yl)butyl)-4-(3,4-dichlorophenyl)piperazine-1-carboxamide (60). Prepared from 4-(4-(2-(tert-butyl)-6-(trifluoromethyl)pyrimidin-4-yl)piperazin-1-yl)butan-1-amine, CDI and 1-(3,4-dichlorophenyl)piperazine as described in Example 1. Yield: 36%. mp 62-64° C. TLC $R_f$ 0.26 (CHCl$_3$-MeOH, 92:5); $^1$HNMR (DMSO-$d_6$) δ 1.28 (s, 9H), 1.44 (bs, 4H), 2.32 (bs, 2H), 2.40-2.50 (bs, 4H), 3.04-3.09 (bq, 2H), 3.14 (t, 4H), 3.41 (t, 4H), 3.64-3.77 (broad hump, 4H), 6.60 (t, 1H), 6.94 (dd, J=9.1, 9.0 Hz, 1H), 7.04 (s, 1H), 7.15 (d, J=3.2 HZ, 1H), 7.38 (d, J=9.0 Hz, 1H); ESI MS m/z 616 (MH)$^+$. Anal. ($C_{28}H_{38}Cl_2F_3N_7O$—$H_2O$) Calcd: C, 53.00; H, 6.35; N, 15.45. Found: C, 52.98; H, 5.98; N, 15.46.

EXAMPLE 61

N-(4-(4-(2-(tert-Butyl)-6-(trifluoromethyl)pyrimidin-4-yl)piperazin-1-yl)butyl)-4-(3-cyano-5-(trifluoromethyl)phenyl)piperazine-1-carboxamide (61). Prepared from 4-(4-(2-(tert-butyl)-6-(trifluoromethyl)pyrimidin-4-yl)piperazin-1-yl)butan-1-amine, CDI and 1-(3-cyano-5-(trifluoromethyl)phenyl)piperazine as described in Example 1. Yield: 29%. mp 57-59° C. TLC $R_f$ 0.23 (CHCl$_3$-MeOH, 92:5); $^1$HNMR (DMSO-$d_6$) δ 1.28 (s, 9H), 1.45 (bs, 4H), 2.32 (bs, 2H), 2.42 (bs, 4H), 3.05-3.09 (bq, 2H), 3.03-3.33 (m, 4H), 3.41-346 (m, 4H), 3.64-3.77 (broad hump, 4H), 6.61 (t, 1H), 7.04 (s, 1H), 7.50 (s, 1H), 7.51 (s, 1H), 7.61 (s, 1H); ESI MS m/z 641 (MH)$^+$. Anal. ($C_{30}H_{38}F_6N_8O$) Calcd: C, 56.24; H, 5.98; N, 17.49. Found: C, 55.99; H, 5.65; N, 17.53.

EXAMPLE 62

4-(2-(tert-Butyl)-6-(trifluoromethyl)pyrimidin-4-yl)-N-(4-(4-(2-(tert-butyl)-6-(trifluoromethyl)pyrimidin-4-yl)piperazin-1-yl)butyl)piperazine-1-carboxamide (62). Prepared from 4-(4-(2-(tert-butyl)-6-(trifluoromethyl)pyrimidin-4-yl)piperazin-1- yl)butan-1-amine, CDI and 1-(2-(tert-butyl)-6-(trifluoromethyl)pyrimidin-4-yl)piperazine as described in Example 1. Yield: 30%. mp 63-65° C. TLC $R_f$ 0.45 (CHCl$_3$-MeOH, 92.5:7.5); $^1$H NMR (DMSO-$d_6$) δ 1.28 (s, 9H), 1.29 (s, 9H), 1.44 (bs, 4H), 2.31 (bs, 2H), 2.42 (t, 4H), 3.06-3.09 (bq, 2H), 3.39-3.43 (m, 4H), 3.71 (bs, 8H), 6.57 (t, 1H), 7.03 (s, 1H), 7.07 (s, 1H); ESI MS m/z 674 (MH)$^+$. Anal. ($C_{31}H_{45}F_6N_9O.0.5H_2O$) Calcd: C, 54.56; H, 6.79; N, 18.46. Found: C, 55.99; H, 5.65; N, 17.53.

EXAMPLE 63

N-(4-(4-(2-(tert-Butyl)-6-(trifluoromethyl)pyrimidin-4-yl)piperazin-1-yl)butyl)-4-(7-chloroquinolin-4-yl)piperazine-1-carboxamide (63). Prepared from 4-(4-(2-(tert-butyl)-6-(trifluoromethyl)pyrimidin-4-yl)piperazin-1-yl)butan-1-amine, CDI and 1-(7-chloroquinolin-4-yl)piperazine as described in Example 1. Yield: 31%. mp 80-82° C. TLC $R_f$ 0.34 (CHCl$_3$-MeOH, 92.5:7.5); $^1$HNMR (DMSO-$d_6$) δ 1.28 (s, 9H), 1.46 (bs, 4H), 2.33 (bs, 2H), 2.43 (t, 4H), 3.07-3.09 (bq, 2H), 3.13 (t, 4H), 3.57 (t, 4H), 3.71 (bs, 4H), 6.62 (t, 1H), 7.02-7.05 (m, 2H), 7.55 (dd, J=9.0, 9.0 Hz, 1H), 7.99 (d, J=2.4 Hz, 1H), 8.07 (d, J=9.0 Hz, 1H), 8.71 (d, J=4.7 Hz, 1H); ESI MS m/z 633 (MH)$^+$. Anal. ($C_{31}H_{40}F_3N_8O.0.5H_2O$) Calcd: C, 57.98; H, 6.49; N, 17.45. Found: C, 57.91; H, 6.15; N, 17.27.

EXAMPLE 64

N-(4-(4-(2-(tert-Butyl)-6-(trifluoromethyl)pyrimidin-4-yl)piperazin-1-yl)butyl)-4-methylpiperazine-1-carboxamide (64). Prepared from 4-(4-(2-(tert-butyl)-6-(trifluoromethyl)pyrimidin-4-yl)piperazin-1-yl)butan-1-amine, CDI and 1-methylpiperazine as described in Example 1. Yield: 29%. mp 68-72° C. TLC $R_f$ 0.21 (CHCl$_3$-MeOH, 92.5:7.5); $^1$H NMR (DMSO-$d_6$) δ 1.28 (s, 9H), 1.43 (t, 4H), 2.16 (s, 3H), 2.23 (t, 4H), 2.30 (t, 2H), 2.41 (t, 4H), 3.02-3.05 (bq, 2H), 3.26 (t, 4H), 3.71 (bs, 4H), 6.43 (t, 1H), 7.03 (s, 1H), ESI MS m/z 486 (MH)$^+$. Anal. ($C_{23}H_{38}F_3N_7O.0.5H_2O$) Calcd: C, 55.85; H, 7.95; N, 19.82. Found: C, 55.79; H, 7.70; N, 19.57.

EXAMPLE 65

N-(4-(4-(2-(tert-Butyl)-6-(trifluoromethyl)pyrimidin-4-yl)piperazin-1-yl)butyl)-4-ethylpiperazine-1-carboxamide (65). Prepared from 4-(4-(2-(tert-butyl)-6-(trifluoromethyl)pyrimidin-4-yl)piperazin-1-yl)butan-1-amine, CDI and 1-ethylpiperazine as described in Example 1. Yield: 38%. Viscous oil. TLC $R_f$ 0.34 (CHCl$_3$-MeOH, 92.5:7.5); $^1$H NMR (DMSO-$d_6$) δ 0.99 (s, 3H), 1.28 (s, 9H), 1.43 (t, 4H), 2.27-2.35 (m, 8H), 2.42 (t, 4H), 3.01-3.05 (bq, 2H), 3.26 (t, 4H), 3.71 (bs, 4H), 6.43 (t, 1H), 7.03 (s, 1H), ESI MS m/z 500 (MH)$^+$. Anal. ($C_{24}H_{40}F_3N_7O.0.25H_2O$) Calcd: C, 57.18; H, 8.10; N, 19.45. Found: C, 57.29; H, 8.10; N, 19.25.

EXAMPLE 66

N-(4-(4-(2-(tert-Butyl)-6-(trifluoromethyl)pyrimidin-4-yl)piperazin-1-yl)butyl)-4-isopropylpiperazine-1-carboxamide (66). Prepared from 4-(4-(2-(tert-butyl)-6-(trifluoromethyl)pyrimidin-4-yl)piperazin-1-yl)butan-1-amine, CDI and 1-isopropylpiperazine as described in Example 1. Yield: 32%. Viscous oil. TLC $R_f$ 0.33 (CHCl$_3$-MeOH, 92.5:7.5); $^1$H NMR (DMSO-$d_6$) δ 0.94 (s, 3H), 0.96 (s, 3H), 1.28 (s, 9H), 1.42 (t, 4H), 2.23 (t, 2H), 2.34 (t, 4H), 2.42 (t, 4H), 2.51-2.67 (m, 1H) 3.01-3.05 (bq, 2H), 3.24 (t, 4H), 3.71 (bs, 4H), 6.40 (t, 1H), 7.03 (s, 1H), ESI MS m/z 514 (MH)$^+$. Anal. ($C_{25}H_{42}F_3N_7O$—$H_2O$) Calcd: C, 56.48; H, 8.34; N, 18.44. Found: C, 56.68; H, 8.66; N, 18.70.

EXAMPLE 67

2-Benzyl-N-(4-(4-(2-(tert-butyl)-6-(trifluoromethyl)pyrimidin-4-yl)piperazin-1-yl)butyl)-4-cyclopropylpiperazine-1-carboxamide (67). Prepared from 4-(4-(2-(tert-butyl)-6-(trifluoromethyl)pyrimidin-4-yl)piperazin-1-yl)butan-1-amine, CDI and 3-benzyl-1-cyclopropylpiperazine as described in Example 1. Yield: 50%. mp 62-64° C. TLC $R_f$ 0.27 (CHCl$_3$-MeOH, 95:5); $^1$HNMR (DMSO-$d_6$) δ 0.22-0.26 and 0.33-0.44 (2 m, 4H), 1.28 (s, 9H), 1.42 (bs, 4H), 1.50-1.57 (m, 1H), 2.03-2.14 (m, 2H), 2.33 (bs, 2H), 2.46 (bs, 4H), 2.53-2.56 (m, 2H), 2.86-3.09 (m, 6H), 3.71 (bs, 4H), 4.14 (bs, 1H), 6.43 (t, 1H), 7.03 (s, 1H), 7.16-7.21 (m, 3H, 7.27-7.31 (m, 2H); ESI MS m/z 602 (MH)$^+$. Anal. ($C_{32}H_{46}F_3N_7O.0.5H_2O$) Calcd: C, 62.93; H, 7.76; N, 16.05. Found: C, 62.97; H, 7.57; N, 15.97.

EXAMPLE 68

N-(4-(4-(2-(tert-Butyl)-6-(trifluoromethyl)pyrimidin-4-yl)piperazin-1-yl)butyl)-4-(cyclopropylmethyl)piperazine- 1-carboxamide (68). Prepared from 4-(4-(2-(tert-butyl)-6-(trifluoromethyl)pyrimidin-4-yl)piperazin-1-yl)butan-1-amine, CDI and 1-(cyclopropylmethyl)piperazine as described in Example 1. Yield: 36%. Viscous oil. TLC $R_f$ 0.35 (CHCl$_3$-MeOH, 92.5:7.5); $^1$H NMR (DMSO-d$_6$) δ 0.06-0.09 (m, 2H), 0.44-0.50 (m, 2H), 0.82-0.87 (m, 1H), 1.28 (s, 9H), 1.43 (t, 4H), 2.21-2.28 (bs, 2H), 2.31 (t, 2H), 2.41-2.45 (m, 8H), 3.01-3.05 (bq, 2H), 3.30 (bs, 4H), 3.71 (bs, 4H), 6.44 (t, 1H), 7.03 (s, 1H), ESI MS m/z 526 (MH)$^+$. Anal. (C$_{26}$H$_{42}$F$_3$N$_7$O.0.5H$_2$O) Calcd: C, 58.41; H, 8.11; N, 18.34. Found: C, 58.51; H, 7.87; N, 18.17.

EXAMPLE 69

N-(4-(4-(2-(tert-Butyl)-6-(trifluoromethyl)pyrimidin-4-yl)piperazin-1-yl)butyl)-4-cyclohexylpiperazine-1-carboxamide (69). Prepared from 4-(4-(2-(tert-butyl)-6-(trifluoromethyl)pyrimidin-4-yl)piperazin-1-yl)butan-1-amine, CDI and 1-cyclohexylpiperazine as described in Example 1. Yield: 28%. mp 54-58° C. TLC $R_f$ 0.49 (CHCl$_3$-MeOH, 92.5:7.5); $^1$H NMR (DMSO-d$_6$) δ 0.8-1.24 (m, 4H), 1.28 (s, 9H), 1.45 (bs, 4H), 1.54-1.58 (m, 1H), 1.78-1.75 (m, 4H), 2.11-2.24 (m, 2H), 2.37-2.43 (m, 8H), 2.97 (t, 2H), 3.05 (bq, 2H), 3.24 (t, 4H), 3.70 (bs, 4H), 6.38 (t, 1H), 7.03 (s, 1H), ESI MS m/z 554 (MH)$^+$. Anal. (C$_{28}$H$_{46}$F$_3$N$_7$O.0.25H$_2$O) Calcd: C, 60.26; H, 8.40; N, 17.56. Found: C, 60.25; H, 8.51; N, 17.55.

EXAMPLE 70

N-(4-(4-(2-(tert-Butyl)-6-(trifluoromethyl)pyrimidin-4-yl)piperazin-1-yl)butyl)-3,4-dihydroquinoline-1(2H)-carboxamide (70). Prepared from 4-(4-(2-(tert-butyl)-6-(trifluoromethyl)pyrimidin-4-yl)piperazin-1-yl)butan-1-amine, CDI and 1,2,3,4-tetrahydroquinoline as described in Example 1. Yield: 35%. Viscous oil. TLC $R_f$ 0.29 (CHCl$_3$-MeOH, 95:5); $^1$HNMR (DMSO-d$_6$) δ 1.28 (s, 9H), 1.47 (t, 4H), 1.78-1.85 (m, 2H), 2.33 (t, 2H), 2.42 (t, 4H), 2.67 (t, 2H), 3.08-3.13 (bq, 2H), 3.50 (t, 2H), 3.71 (bs, 4H), 6.66 (t, 1H), 6.86-6.92 (m, 1H), 7.02-7.09 (m, 3H), 7.38-7.42 (m, 1H); ESI MS m/z 519 (MH)$^+$. Anal. (C$_{27}$H$_{37}$F$_3$N$_6$O—H$_2$O) Calcd: C, 60.43; H, 7.32; N, 15.66. Found: C, 60.41; H, 7.45; N, 16.00.

EXAMPLE 71

N-(4-(4-(2-(tert-Butyl)-6-(trifluoromethyl)pyrimidin-4-yl)piperazin-1-yl)butyl)indoline-1-carboxamide (71). Prepared from 4-(4-(2-(tert-butyl)-6-(trifluoromethyl)pyrimidin-4-yl)piperazin-1-yl)butan-1-amine, CDI and indoline as described in Example 1. Yield: 20%. mp 50-52° C. TLC $R_f$ 0.22 (CHCl$_3$-MeOH, 95:5); $^1$HNMR (DMSO-d$_6$) δ 1.28 (s, 9H), 1.50 (bs, 4H), 2.38 (bs, 2H), 2.44 (bs, 4H), 3.07-3.15 (m, 4H), 3.71 (bs, 4H), 3.86 (t, 2H), 6.59 (t, 1H), 6.86-6.92 (m, 1H), 7.03-7.07 (m, 2H), 7.11 (dd, J=7.4, 7.4 Hz, 1H), 7.82 (d, J=7.9 Hz, 1H). ESI MS m/z 505 (MH)$^+$. Anal. (C$_{26}$H$_{35}$F$_3$N$_6$O.0.25H$_2$O) Calcd: C, 61.34; H, 7.03; N, 16.51. Found: C, 61.17; H, 6.72; N, 16.41.

EXAMPLE 72

N-(4-(4-(2-(tert-Butyl)-6-(trifluoromethyl)pyrimidin-4-yl)piperazin-1-yl)butyl)-4-(3-cyanobenzyl)piperazine-1-carboxamide (72). Prepared from 4-(4-(2-(tert-butyl)-6-(trifluoromethyl)pyrimidin-4-yl)piperazin-1-yl)butan-1-amine, CDI and 1-(3-cyanobenzyl)piperazine as described in Example 1. Yield: 26%. mp 58-59° C. TLC $R_f$ 0.39 (CHCl$_3$-MeOH, 95:5); $^1$H NMR (DMSO-d$_6$) δ 1.28 (s, 9H), 1.43 (t, 4H), 2.31 (t, 6H), 2.42 (t, 4H), 3.01-3.04 (bq, 2H), 3.28 (t, 4H), 3.54 (s, 2H), 3.71 (bs, 4H), 6.44 (t, 1H), 7.04 (s, 1H), 7.52-7.57 (m, 1H), 7.65 (dd, J=7.9, 7.8 Hz, 1H), 7.72-7.75 (m, 2H); ESI MS m/z 587 (MH)$^+$. Anal. (C$_{30}$H$_{41}$F$_3$N$_8$O.0.5H$_2$O) Calcd: C, 60.49; H, 7.11; N, 18.81. Found: C, 60.21; H, 6.72; N, 18.86.

EXAMPLE 73

N-(4-(4-(2-(tert-Butyl)-6-(trifluoromethyl)pyrimidin-4-yl)piperazin-1-yl)butyl)-4-((4-chlorophenyl)(phenyl)methyl)piperazine-1-carboxamide (73. Prepared from 4-(4-(2-(tert-butyl)-6-(trifluoromethyl)pyrimidin-4-yl)piperazin-1-yl)butan-1-amine, CDI and 1-((4-chlorophenyl)(phenyl)methyl)piperazine as described in Example 1. Yield: 36%. mp 132-134° C. TLC $R_f$ 0.60 (CHCl$_3$-MeOH, 92.5:7.5); $^1$H NMR (DMSO-d$_6$) δ 1.28 (s, 9H), 1.41 (t, 4H), 2.27 (t, 2H), 2.28 (t, 4H), 2.40 (t, 4H), 3.00-3.02 (bq, 2H), 3.28 (t, 4H), 3.54 (s, 2H), 3.70 (bs, 4H), 4.34 (s, 1H), 6.41 (t, 1H), 7.04 (s, 1H), 7.18-7.28 (m, 1H), 7.30-7.46 (m, 6H); ESI MS m/z 672 (MH)$^+$. Anal. (C$_{35}$H$_{45}$ClF$_3$N$_7$O.25H$_2$O) Calcd: C, 62.12; H, 6.78; N, 14.49. Found: C, 62.12; H, 6.51; N, 14.32.

EXAMPLE 74

N-(4-(4-(2-(tert-Butyl)-6-(trifluoromethyl)pyrimidin-4-yl)piperazin-1-yl)butyl)-4-cinnamylpiperazine-1-carboxamide (74). Prepared from 4-(4-(2-(tert-butyl)-6-(trifluoromethyl)pyrimidin-4-yl)piperazin-1-yl)butan-1-amine, CDI and 1-cinnamylpiperazine as described in Example 1. Yield: 32%. mp 46-48° C. TLC $R_f$ 0.59 (CHCl$_3$-MeOH, 90:10); $^1$H NMR (DMSO-d$_6$) δ 1.28 (s, 9H), 1.41 (t, 4H), 2.27 (t, 2H), 2.34 (t, 4H), 2.49 (t, 4H), 3.01-3.04 (bq, 2H), 3.02-3.11 (m, 2H), 3.27 (t, 4H), 3.71 (bs, 4H), 6.26-6.34 (m, 1H), 6.44 (t, 1H), 6.51 (d, 16.0 Hz, 1H), 7.04 (s, 1H), 7.20-7.29 (m, 1H), 7.30-7.37 (m, 2H), 7.74-7.76 (m, 2H); ESI MS m/z 588 (MH)$^+$. Anal. (C$_{31}$H$_{44}$ClF$_3$N$_7$O.0.5H$_2$O) Calcd: C, 62.40; H, 7.60; N, 16.43. Found: C, 62.26; H, 7.36; N, 16.68.

EXAMPLE 75

N-(4-(4-(2-(tert-Butyl)-6-(trifluoromethyl)pyrimidin-4-yl)piperazin-1-yl)butyl)-[1,4'-bipiperidine]-1'-carboxamide (75). Prepared from 4-(4-(2-(tert-butyl)-6-(trifluoromethyl)pyrimidin-4-yl)piperazin-1-yl)butan-1-amine, CDI and 1,4'-bipiperidine as described in Example 1. Yield: 41%. mp 108-110° C. TLC $R_f$ 0.29 (CHCl$_3$-MeOH, 90:10); $^1$H NMR (DMSO-d$_6$) δ 1.19-1.29 (m, 1H), 1.28 (s, 9H), 1.33-1.48 (m, 10H), 1.60-1.65 (m, 2H), 2.21 (t, 2H), 2.41 (t, 4H), 2.42-2.61 (m, 6H), 3.01-3.04 (bq, 2H), 3.02-3.11 (m, 2H), 3.71 (bs, 4H), 3.94-3.99 (m, 2H), 6.41 (t, 1H), 7.04 (s, 1H); ESI MS m/z 554 (MH)$^+$. Anal. (C$_{28}$H$_{46}$F$_3$N$_7$O.0.75H$_2$O) Calcd: C, 59.29; H, 8.44; N, 17.29. Found: C, 59.23; H, 8.23; N, 16.98.

EXAMPLE 76

N-(4-(4-(2-(tert-Butyl)-6-(trifluoromethyl)pyrimidin-4-yl)piperazin-1-yl)butyl)-4-(1-methylpiperidin-4-yl)piperazine-1-carboxamide (76). Prepared from 4-(4-(2-(tert-butyl)-6-(trifluoromethyl)pyrimidin-4-yl)piperazin-1-yl)butan-1-amine, CDI and 1-(1-methylpiperidin-4-yl)piperazine as described in Example 1. Yield: 22%. mp 47-48° C. TLC $R_f$ 0.20 (CHCl$_3$-MeOH, 95:5); $^1$HNMR (DMSO-d$_6$) δ 1.28 (s, 9H), 1.33-1.42 (m, 8H), 1.66-1.69 (m, 2H), 1.80 (t, 2H), 2.07-2.09 (m, 1H), 2.11 (s, 3H), (t, 2H), 2.97 (t, 2H), 2.37-2.44 (m, 6H), 7.74 (d, J=11.5 Hz, 2H), 3.01-3.04 (bq, 2H), 3.23 (t, 2H), 3.71 (bs, 4H), 6.41 (t, 1H), 7.02 (s, H). ESI MS m/z 569 (MH)$^+$. Anal. ($C_{28}H_{47}F_3N_8O.0.25H_2O$) Calcd: C, 58.67; H, 8.35; N, 19.55. Found: C, 58.68; H, 8.25; N, 19.19.

EXAMPLE 77

N-(4-(4-(2-(tert-Butyl)-6-(trifluoromethyl)pyrimidin-4-yl)piperazin-1-yl)butyl)-4-(phenylsulfonyl)piperazine-1-carboxamide (77). Prepared from 4-(4-(2-(tert-butyl)-6-(trifluoromethyl)pyrimidin-4-yl)piperazin-1-yl)butan-1-amine, CDI and 1-(phenylsulfonyl)piperazine as described in Example 1. Yield: 33%. mp 50-52° C. TLC $R_f$ 0.40 (CHCl$_3$-MeOH, 95:5); $^1$HNMR (DMSO-d$_6$) δ 1.28 (s, 9H), 1.35 (t, 4H), 2.25 (t, 2H), 2.38 (t, 4H), 2.82 (t, 4H), 2.95 (bq, 2H), 3.37 (m, 4H), 3.70 (bs, 4H), 6.51 (t, 1H), 7.02 (s, 1H), 7.63-7.77 (m, 5H); ESI MS m/z 612 (MH)$^+$. Anal. ($C_{28}H_{40}F_3N_7O_3S.0.75H_2O$) Calcd: C, 53.75; H, 6.69; N, 15.68. Found: C, 53.95; H, 6.47; N, 15.41.

EXAMPLE 78

N-(4-(4-(2,6-Di-tert-butylpyrimidin-4-yl)piperazin-1-yl)butyl)-4-(phenylsulfonyl)piperazine-1-carboxamide (78). Prepared from 4-(4-(2,6-di-tert-butylpyrimidin-4-yl)piperazin-1-yl)butan-1-amine, CDI and 1-(phenylsulfonyl)piperazine as described in Example 1. Yield: 28%. mp 164-66° C. TLC $R_f$ 0.45 (CHCl$_3$-MeOH, 95:5); $^1$H NMR (DMSO-d$_6$) δ 1.24 (s, 9H), 1.28 (s, 9H), 1.36 (t, 4H), 2.24 (t, 2H), 2.37 (t, 4H), 2.82 (t, 4H), 2.96 (bq, 2H), 3.36 (m, 4H), 3.57 (t, 4H), 6.44 (s, 1H), 6.51 (t, 1H), 7.61-7.77 (m, 5H); ESI MS m/z 600 (MH)$^+$. Anal. ($C_{31}H_{49}F_3N_7O_3S.0.5H_2O$) Calcd: C, 61.16; H, 8.28; N, 16.10. Found: C, 61.31; H, 8.10; N, 16.10.

EXAMPLE 79

N-(4-(4-(2-(tert-Butyl)-6-(trifluoromethyl)pyrimidin-4-yl)piperazin-1-yl)butyl)-4-(4-chlorophenyl)-4-hydroxypiperidine-1-carboxamide (79). Prepared from 4-(4-(2-(tert-butyl)-6-(trifluoromethyl)pyrimidin-4-yl)piperazin-1-yl)butan-1-amine, CDI and 4-(4-chlorophenyl)piperidin-4-ol as described in Example 1. Yield: 31%. mp 75-77° C. TLC $R_f$ 0.18 (CHCl$_3$-MeOH, 9.5:7.5); $^1$H NMR (DMSO-d$_6$) δ 1.28 (s, 9H), 1.44 (t, 4H), 1.51-1.55 (m, 2H), 1.71-1.79 (m, 2H), 2.21 (t, 2H), 2.42 (t, 4H), 3.02-3.09 (m, 4H), 3.70 (bs, 4H), 3.82-3.86 (m, 2H), 5.11 (s, 1H), 6.44 (t, 1H), 7.04 (s, 1H), 7.33-7.38 (m, 2H), 7.45-7.49 (m, 2H); ESI MS m/z 597 (MH)$^+$. Anal. ($C_{29}H_{40}ClF_3N_6O_2.0.25H_2O$) Calcd: C, 57.90; H, 6.79; N, 13.79. Found: C, 57.70; H, 6.50; N, 13.98.

EXAMPLE 80

N-(4-(4-(2-(tert-Butyl)-6-(trifluoromethyl)pyrimidin-4-yl)piperazin-1-yl)butyl)-4-cyclopropyl-2-phenylpiperazine-1-carboxamide (80). Prepared from 4-(4-(2-(tert-butyl)-6-(trifluoromethyl)pyrimidin-4-yl)piperazin-1-yl)butan-1-amine, CDI and 1-cyclopropyl-3-phenylpiperazine as described in Example 1. Yield: 42%. mp 65-66° C. TLC $R_f$ 0.22 (CHCl$_3$-MeOH, 95:5); $^1$HNMR (DMSO-d$_6$) δ 0.21-0.29 and 0.38-0.45 (2 m, 4H), 1.28 (s, 9H), 1.43 (bs, 4H), 1.57-1.61 (m, 1H), 2.17-2.23 (m, 1H), 2.32 (bs, 2H), 2.46 (bs, 4H), 2.49-2.54 (m, 2H), 2.71.-2.81 (m, 2H), 3.04-3.11 (m, 2H), 3.42 (d, J=11.0 Hz, 1H), 3.71 (bs, 4H), 5.24 (s, 1H), 6.55 (t, 1H), 7.04 (s, 1H), 7.14-7.18 (m, 3H), 7.24-7.33 (m, 2H); ESI MS m/z 588 (MH)$^+$. Anal. ($C_{31}H_{44}F_3N_7O.0.25H_2O$) Calcd: C, 62.87; H, 7.57; N, 16.56. Found: C, 62.50; H, 7.50; N, 16.43.

EXAMPLE 81

N-(4-(4-(2-(tert-Butyl)-6-(trifluoromethyl)pyrimidin-4-yl)piperazin-1-yl)butyl)-4-phenyl-1,4-diazepane-1-carboxamide (81). Prepared from 4-(4-(2-(tert-butyl)-6-(trifluoromethyl)pyrimidin-4-yl)piperazin-1-yl)butan-1-amine, CDI and 1-phenyl-1,4-diazepane as described in Example 1. Yield: 30%. mp 51-53° C. TLC $R_f$ 0.48 (CHCl$_3$-MeOH, 92.5:7.5); $^1$H NMR (DMSO-d$_6$) δ 1.28 (s, 9H), 1.41 (bs, 4H), 1.87-1.88 (m, 2H), 2.39 (bs, 2H), 2.51 (bs, 4H), 2.99-3.40 (m, 2H), 3.19 (t, 2H), 3.44-3.46 (m, 6H), 3.75 (bs, 4H), 6.27 (t, 1H), 6.56 (t, 1H), 6.70 (d, J=8.0 Hz, 2H), 7.06 (s, 1H), 7.10-7.16 (m, 2H); ESI MS m/z 562 (MH)$^+$. Anal. ($C_{29}H_{42}F_3N_7O$—$H_2O$) Calcd: C, 60.09; H, 7.65; N, 16.91. Found: C, 59.65; H, 7.42; N, 16.54.

EXAMPLE 82

N-(4-(4-(2-(tert-Butyl)-6-(trifluoromethyl)pyrimidin-4-yl)piperazin-1-yl)butyl)-4-phenylazepane-1-carboxamide (82). Prepared from 4-(4-(2-(tert-butyl)-6-(trifluoromethyl)pyrimidin-4-yl)piperazin-1-yl)butan-1-amine, CDI and 4-phenylazepane hydrochloride as described in Example 1. Yield: 22%. mp 45-47° C. TLC $R_f$ 0.36 (CHCl$_3$-MeOH, 95:5); $^1$HNMR (DMSO-d$_6$) δ 1.28 (s, 9H), 1.47 (bs, 4H), 1.57-1.89 (m, 6H), 2.36 (bs, 2H), 2.46 (bs, 4H), 2.56-2.64 (m, 1H), 3.06 (bq, 2H), 3.17-3.25 (m, 1H), 3.28-3.32 (m, 1H), 3.45-3.52 (m, 1H), 3.58-3.66 (m, 1H), 3.72 (bs, 4H), 6.21 (t, 1H), 7.04 (s, 1H), 7.10-7.19 (m, 3H), 7.22-7.28 (m, 2H); ESI MS m/z 561 (MH)$^+$. Anal. ($C_{30}H_{43}F_3N_6O.0.75H_2O$) Calcd: C, 62.75; H, 7.81; N, 14.64. Found: C, 62.44; H, 7.45; N, 14.54.

EXAMPLE 83

4-Phenyl-N-(4-(4-(7-(trifluoromethyl)quinolin-4-yl)piperazin-1-yl)butyl)piperazine-1-carboxamide (83). Prepared from 4-(4-(7-(trifluoromethyl)quinolin-4-yl)piperazin-1-yl)butan-1-amine, CDI and 1-phenylpiperazine as described in Example 1. Yield: 45%. mp 122-125° C. TLC $R_f$ 0.53 (CHCl$_3$-MeOH, 92.5:7.5); $^1$HNMR (DMSO-d$_6$) δ 1.47 (t, 4H), 2.38 (t, 2H), 2.65 (bs, 4H), 3.07 (t, 6H), 3.21 (bs, 4H), 3.46 (t, 4H), 6.57 (t, 1H), 6.78 (t, 1H), 6.94 (d, J=7.8 Hz, 2H), 7.10 (d, J=5.0 Hz, 1H), 7.19 (dd, J=8.6, 8.6 Hz, 2H), 7.78 (dd, J=9.0 and 8.9 Hz, 1H), 8.20-8.27 (m, 2H), 8.8 (d, J=5.1 Hz, 1H); ESI MS m/z 541 (MH)$^+$. Anal. ($C_{29}H_{35}F_3N_6O.0.25H_2O$) Calcd: C, 63.90; H, 6.56; N, 15.42. Found: C, 63.78; H, 6.22; N, 15.37.

EXAMPLE 84

4-Phenyl-N-(4-(4-(quinolin-2-yl)piperazin-1-yl)butyl)piperazine-1-carboxamide (84). Prepared from 4-(4-(quinolin-2-yl)piperazin-1-yl)butan-1-amine, CDI and 1-phenylpiperazine as described in Example 1. Yield: 27%. mp 108-110° C. TLC $R_f$ 0.59 (CHCl$_3$-MeOH, 92.5:7.5); $^1$H NMR (DMSO-d$_6$) δ 1.42 (bs, 4H), 2.32 (t, 2H), 2.47 (t, 4H), 3.07 (t, 6H), 3.43 (t, 4H), 3.66 (t, 4H), 6.57 (t, 1H), 6.78 (t, 1H), 6.95 (d, J=7.8 Hz, 2H), 7.19-7.24 (m, 4H), 7.49-7.57 (m, 2H), 7.67 (d, J=8.2 Hz, 1H), 8.01 (d, J=9.2 Hz, 1H, ESI MS m/z 473 (MH)$^+$. Anal. ($C_{28}H_{36}N_6O$) Calcd: C, 71.16; H, 7.68; N, 17.78. Found: 70.91; H, 7.37; N, 17.68.

EXAMPLE 85

N-(4-(4-(7-Chloroquinolin-4-yl)piperazin-1-yl)butyl)-4-phenylpiperidine-1-carboxamide (85). Prepared from 4-(4-

(7-chloroquinolin-4-yl)piperazin-1-yl)butan-1-amine, CDI and 4-phenylpiperidine as described in Example 1. Yield: 20%. mp 124-128° C. TLC R$_f$ 0.74 (CHCl$_3$-MeOH, 85:15); $^1$H NMR (DMSO-d$_6$) δ 1.40-1.52 (m, 6H), 1.71-1.74 (m, 2H), 2.40 (t, 2H), 2.64 (m, 4H), 2.69-2.76 (m, 3H), 3.06 (t, 2H), 3.18 (t, 4H), 4.08-4.11 (m, 2H), 6.47 (t, 1H), 6.99 (d, J=5.1 Hz, 1H), 7.15-7.30 (m, 5H), 7.54 (dd, J=9.0, 9.0 Hz, 1H), 7.98 (d, J=2.01 Hz, 1H), 8.00 (d, J=9.0 Hz, 1H), 8.69 (d, J=5.1 Hz, 1H); ESI MS m/z 506 (MH)$^+$. Anal. (C$_{29}$H$_{36}$ClN$_5$O) Calcd: C, 68.83; H, 7.17; N, 13.84. Found: 68.45; H, 6.96; N, 13.63.

EXAMPLE 86

N-(4-(4-(3,5-Di-tert-butylphenyl)piperazin-1-yl)butyl)-4-phenylpiperazine-1-carboxamide (86. Prepared from 4-(4-(3,5-di-tert-butylphenyl)piperazin-1-yl)butan-1-amine, CDI and 1-phenylpiperazine as described in Example 1. Yield: 31%. mp 138-140° C. TLC R$_f$ 0.35 (CHCl$_3$-MeOH, 92.5:7.5); $^1$H NMR (DMSO-d$_6$) δ 1.25 (s, 18H), 1.45 (bs, 4H), 2.31 (bs, 2H), 2.42-2.49 (m, 4H), 3.05-3.10 (m, 10H), 3.43 (t, 4H), 6.57 (t, 1H), 6.72 (d, J=1.5 Hz, 1H), 6.77-6.81 (m, 1H), 6.85 (t, 2H), 6.94 (d, J=7.8 Hz, 2H), 7.18-7.24 (m, 2H); ESI MS m/z 534 (MH)$^+$. Anal. (C$_{33}$H$_5$, N$_7$O—H$_2$O) Calcd: C, 73.63; H, 9.64; N, 13.01. Found: C, 73.47; H, 9.42; N, 13.06.

EXAMPLE 87

N-(4-(4-(2-(tert-Butyl)-6-(trifluoromethyl)pyrimidin-4-yl)piperazin-1-yl)butyl)-3-methyl-5,6-dihydro-[1,2,4]triazolo[4,3-a]pyrazine-7(8H)-carboxamide (87). Prepared from 4-(4-(2-(tert-butyl)-6-(trifluoromethyl)pyrimidin-4-yl)piperazin-1-yl)butan-1-amine, CDI and 3-methyl-5,6,7,8-tetrahydro-[1,2,4]triazolo[4,3-a]pyrazine as described in Example 1. Yield: 39%. mp 78-80° C. TLC R$_f$, 0.62 (CHCl$_3$-MeOH, 92.5:7.5); $^1$H NMR (DMSO-d$_6$) δ 1.28 (s, 9H), 1.44 (bs, 4H), 2.29 (s, 3H), 2.32 (bs, 2H), 2.41 (t, 4H), 3.06-3.08 (bq, 2H), 3.70 (t, 4H), 3.75 (t, 2H), 3.86 (t,4H), 6.84 (t, 1H), 7.04 (s, 1H); ESI MS m/z 524 (MH)$^+$. Anal. (C$_{24}$H$_{36}$F$_3$N$_9$O.0.5H$_2$O) Calcd: C, 54.12; H, 7.00; N, 23.67. Found: C, 54.20; H, 6.78; N, 23.88.

EXAMPLE 88

N-(4-(4-(6-(tert-Butyl)-2-methylpyrimidin-4-yl)piperazin-1-yl)butyl)-3-methyl-5,6-dihydro-[1,2,4]triazolo[4,3-a]pyrazine-7(8H)-carboxamide (88). Prepared from 4-(4-(6-(tert-butyl)-2-methylpyrimidin-4-yl)piperazin-1-yl)butan-1-amine, CDI and 3-methyl-5,6,7,8-tetrahydro-[1,2,4]triazolo[4,3-a]pyrazine as described in Example 1. Yield: 34%. mp 84-86° C. TLC R$_f$, 0.11 (CHCl$_3$-MeOH, 92.5:7.5); $^1$H NMR (DMSO-d$_6$) δ 1.22 (s, 9H), 1.44 (bs, 4H), 2.27 (bs, 2H), 2.28 (s, 3H), 2.35 (s, 3H), 2.39 (t, 4H), 3.06-3.08 (bq, 2H), 3.57 (t, 4H), 3.75 (t, 2H), 3.86 (t, 2H), 4.62 (s, 2H), 6.47 (s, 1H), 6.85 (t, 1H); ESI MS m/z 470 (MH)$^+$. Anal. (C$_{24}$H$_{39}$N$_9$O.0.5H$_2$O) Calcd: C, 59.11; H, 8.48; N, 25.85. Found: C, 58.99; H, 8.61; N, 25.55.

EXAMPLE 89

N-(4-(4-(2-(tert-Butyl)-6-(trifluoromethyl)pyrimidin-4-yl)piperazin-1-yl)butyl)-3,4-dihydro-1H-pyrido[4,3-b]indole-2(5H)-carboxamide (89). Prepared from 4-(4-(2-(tert-butyl)-6-(trifluoromethyl)pyrimidin-4-yl)piperazin-1-yl)butan-1-amine, CDI and 2,3,4,5-tetrahydro-1H-pyrido[4,3-b]indole as described in Example 1. Yield: 32%. mp 82-84° C. TLC R$_f$ 0.43 (CHCl$_3$-MeOH, 92.5:7.5); $^1$HNMR (DMSO-d$_6$) δ 1.28 (s, 9H), 1.45 (bs, 4H), 2.30 (t, 2H), 2.40 (t, 4H), 2.74 (t, 2H), 3.07 (bq, 2H), 3.69 (bs, 6H), 4.49 (s, 2H), 6.59 (t, 1H), 6.92-7.04 (m, 3H), 7.21 (d, J=7.8 Hz, 1H), 7.34 (d, J=7.8 Hz, 1H), 10.83 (s, 1H). ESI MS m/z 558 (MH)$^+$. Anal. (C$_{29}$H$_{38}$F$_3$N$_7$O.0.25H$_2$O) Calcd: C, 61.96; H, 6.90; N, 17.44. Found: C, 61.98; H, 6.81; N, 17.25.

EXAMPLE 90

N-(4-(4-(2-(tert-Butyl)-6-(trifluoromethyl)pyrimidin-4-yl)piperazin-1-yl)butyl)-8-methyl-3,4-dihydro-1H-pyrido[4,3-b]indole-2(5H)-carboxamide (90). Prepared from 4-(4-(2-(tert-butyl)-6-(trifluoromethyl)pyrimidin-4-yl)piperazin-1-yl)butan-1-amine, CDI and 8-methyl-2,3,4,5-tetrahydro-1H-pyrido[4,3-b]indole as described in Example 1. Yield: 32%. mp 92-94° C. TLC R$_f$ 0.53 (CHCl$_3$-MeOH, 92.5:7.5); $^1$H NMR (DMSO-d$_6$) δ 1.28 (s, 9H), 1.45 (bs, 4H), 2.30 (t, 2H), 2.38 (s, 3H), 2.40 (t, 4H), 2.72 (t, 2H), 3.08 (bq, 2H), 3.69 (bs, 6H), 4.46 (s, 2H), 6.56 (t, 1H), 6.83 (dd, J=8.2, 8.2 Hz, 1H), 7.01 (m, 1H), 7.13 (s, 1H), 7.15 (d, J=8.2 Hz, 1H), ESI MS m/z 572 (MH)$^+$. Anal. (C$_{30}$H$_{40}$F$_3$N$_7$O.0.5H$_2$O) Calcd: C, 62.05; H, 7.12; N, 16.88. Found: C, 62.17; H, 6.84; N, 16.88.

EXAMPLE 91

N-(4-(4-(2-(tert-Butyl)-6-(trifluoromethyl)pyrimidin-4-yl)piperazin-1-yl)butyl)-8-chloro-3,4-dihydro-1H-pyrido[4,3-b]indole-2(5H)-carboxamide (91). Prepared from 4-(4-(2-(tert-butyl)-6-(trifluoromethyl)pyrimidin-4-yl)piperazin-1-yl)butan-1-amine, CDI and 8-chloro-2,3,4,5-tetrahydro-1H-pyrido[4,3-b]indole as described in Example 1. Yield: 55%. mp 94-96° C. TLC R$_f$, 0.43 (CHCl$_3$-MeOH, 92.5:7.5); $^1$H NMR (DMSO-d$_6$) δ 1.28 (s, 9H), 1.45 (bs, 4H), 2.30 (t, 2H), 2.40 (t, 4H), 2.75 (t, 2H), 3.08 (bq, 2H), 3.69 (bs, 6H), 4.47 (s, 2H), 6.56 (t, 1H), 7.00 (d, J=2.3 Hz, 1H), 7.02 (d, J=2.4 Hz, 1H), 7.28 (d, J=8.2 Hz, 1H), 7.37 (d, J=2.0 Hz, 1H), 11.06 (s, 1H); ESI MS m/z 592 (MH)$^+$. Anal. (C$_{29}$H$_{37}$ClF$_3$N$_7$O.0.25H$_2$O) Calcd: C, 58.38; H, 6.34; N, 16.43. Found: C, 58.41; H, 6.00; N, 16.33.

EXAMPLE 92

N-(4-(4-(2-(tert-Butyl)-6-(trifluoromethyl)pyrimidin-4-yl)piperazin-1-yl)butyl)-8-methoxy-3,4-dihydro-1H-pyrido[4,3-b]indole-2(5H)-carboxamide (92). Prepared from 4-(4-(2-(tert-butyl)-6-(trifluoromethyl)pyrimidin-4-yl)piperazin-1-yl)butan-1-amine, CDI and 8-methoxy-2,3,4,5-tetrahydro-1H-pyrido[4,3-b]indole as described in Example 1. Yield: 44%. mp 84-86° C. TLC R$_f$ 0.38 (CHCl$_3$-MeOH, 92.5:7.5); $^1$H NMR (DMSO-d$_6$) δ 1.28 (s, 9H), 1.45 (bs, 4H), 2.30 (t, 2H), 2.40 (t, 4H), 2 72 (t, 2H), 3.07 (bq 2H), 3.66 (bs, 6H), 3.74 (s, 3H), 4.46 (s, 2H), 6.56 (t, 1H), 6.64 (dd, J=8.6, 8.6 Hz, 1H), 6.84 (d, J=2.8 Hz, 1H), 7.02 (s, 1H), 7.15 (d, J=8.7 Hz, 1H), 10.65 (s, 1H); ESI MS m/z 588 (MH)$^+$. Anal. (C$_{30}$H$_{40}$F$_3$N$_7$O$_2$.0.25H$_2$O) Calcd: C, 60.85; H, 6.89; N, 16.56. Found: C, 60.77; H, 6.84; N, 16.42.

EXAMPLE 93

N-(4-(4-(2-(tert-Butyl)-6-(trifluoromethyl)pyrimidin-4-yl)piperazin-1-yl)butyl)-8-(trifluoromethyl)-3,4-dihydro-1H-pyrido[4,3-b]indole-2(5H)-carboxamide (93). Prepared from 4-(4-(2-(tert-butyl)-6-(trifluoromethyl)pyrimidin-4-yl)piperazin-1-yl)butan-1-amine, CDI and 8-(trifluoromethyl)-2,3,4,5-tetrahydro-1H-pyrido[4,3-b]indole as described in Example 1. Yield: 46%. mp 86-88° C. TLC R$_f$ 0.34 (CHCl$_3$-MeOH, 92.5:7.5); $^1$HNMR (DMSO-d$_6$) δ 1.28 (s, 9H), 1.46 (bs, 4H), 2.31 (t, 2H), 2.41 (t, 4H), 2.78 (t, 2H), 3.08 (bq, 2H), 3.66-3.73 (m, 6H), 4.55 (s, 2H), 6.58 (t, 1H), 7.02 (s, 1H), 7.31 (dd, J=8.6, 8.2 Hz, 1H), 7.46 (d, J=8.2 HZ, 1H), 7.73 (s, 1H), 11.36 (s, 1H); ESI MS m/z 626 (MH)$^+$. Anal. (C$_{30}$H$_{37}$F$_6$N$_7$O.0.5H$_2$O) Calcd: C, 57.78; H, 6.04; N, 15.45. Found: C, 56.88; H, 5.82; N, 15.59.

EXAMPLE 94

N-(4-(4-(6-(tert-Butyl)-2-methylpyrimidin-4-yl)piperazin-1-yl)butyl)-8-methyl-3,4-dihydro-1H-pyrido[4,3-b]indole-2(5H)-carboxamide (94). Prepared from 4-(4-(6-(tert-butyl)-2-methylpyrimidin-4-yl)piperazin-1-yl)butan-1-amine, CDI and 8-methyl-2,3,4,5-tetrahydro-1H-pyrido[4,3-b]indole as described in Example 1. Yield: 39%. mp 96-98° C. TLC R$_f$ 0.41 (CHCl$_3$-MeOH, 92.5:7.5); $^1$H NMR (DMSO-d$_6$) δ 1.22 (s, 9H), 1.45 (bs, 4H), 2.28 (t, 2H), 2.34 (s, 3H), 2.35 (s, 3H), 2.38 (t, 4H), 2.72 (t, 2H), 3.07 (bq, 2H), 3.56 (t, 4H), 3.68 (t, 2H), 4.56 (s, 2H), 6.46 (t, 1H), 6.56 (m, 1H), 6.81 (dd, J=8.2, 8.2 Hz, 1H), 7.12 (s, 1H), 7.15 (d, J=8.2 Hz, 1H), 10.67 (s, 1H); ESI MS m/z 518 (MH)$^+$. Anal. (C$_{30}$H$_{43}$N$_7$O.0.25H$_2$O) Calcd: C, 69.00; H, 8.40; N, 18.78. Found: C, 69.11; H, 8.57; N, 18.78.

EXAMPLE 95

N-(4-(4-(6-(tert-Butyl)-2-methylpyrimidin-4-yl)piperazin-1-yl)butyl)-8-chloro-3,4-dihydro-1H-pyrido[4,3-b]indole-2(5H)-carboxamide (95). Prepared from 4-(4-(6-(tert-butyl)-2-methylpyrimidin-4-yl)piperazin-1-yl)butan-1-amine, CDI and 8-chloro-2,3,4,5-tetrahydro-1H-pyrido[4,3-b]indole as described in Example 1. Yield: 34%. mp 106-108° C. TLC R$_f$ 0.30 (CHCl$_3$-MeOH, 92.5:7.5); $^1$H NMR (DMSO-d$_6$) δ 1.20 (s, 9H), 1.45 (bs, 4H), 2.29 (t, 2H), 2.34 (s, 3H), 2.38 (t, 4H), 2.75 (t, 2H), 3.07 (bq, 2H), 3.56 (t, 4H), 3.69 (t, 2H), 4.48 (s, 2H), 6.47 (t, 1H), 6.55 (m, 1H), 7.00 (dd, J=8.7, 8.2 Hz, 1H), 7.28 (d, J=8.6 Hz, 1H), 7.37 (d, J=2.0 Hz, 1H), 11.06 (s, 1H); ESI MS m/z 538 (MH)$^+$. Anal. (C$_{29}$H$_{40}$ClN$_7$O.0.25H$_2$O) Calcd: C, 64.19; H, 7.52; N, 18.07. Found: C, 64.21; H, 7.40; N, 18.08.

EXAMPLE 96

N-(4-(4-(6-(tert-Butyl)-2-methylpyrimidin-4-yl)piperazin-1-yl)butyl)-8-methoxy-3,4-dihydro-1H-pyrido[4,3-b]indole-2(5H)-carboxamide (96). Prepared from 4-(4-(6-(tert-butyl)-2-methylpyrimidin-4-yl)piperazin-1-yl)butan-1-amine, CDI and 8-methoxy-2,3,4,5-tetrahydro-1H-pyrido[4,3-b]indole as described in Example 1. Yield: 34%. mp 90-92° C. TLC R$_f$ 0.38 (CHCl$_3$-MeOH, 92.5:7.5); $^1$H NMR (DMSO-d$_6$) δ 1.22 (s, 9H), 1.45 (bs, 4H), 2.29 (t, 2H), 2.34 (s, 3H), 2.37 (t, 4H), 2.72 (t, 2H), 3.07 (bq, 2H), 3.56 (t, 4H), 3.68 (t, 2H), 3.75 (s, 3H), 4.56 (s, 2H), 6.47 (s, 1H), 6.57 (t, 1H), 6.64 (dd, J=9.0, 8.3 Hz, 1H), 6.84 (d, J=2.4 Hz, 1H), 7.16 (d, J=9.0 Hz, 1H), 10.65 (s, 1H); ESI MS m/z 534 (MH)$^+$. Anal. (C$_{30}$H$_{43}$N$_7$O$_2$.0.5H$_2$O) Calcd: C, 66.39; H, 8.17; N, 18.07. Found: C, 66.43; H, 8.03; N, 18.26.

EXAMPLE 97

N-(4-(4-(3,5-Di-tert-butylphenyl)piperazin-1-yl)butyl)-1,3,4,9-tetrahydro-2H-pyrido[3,4-b]indole-2-carboxamide (97). Prepared from 4-(4-(3,5-di-tert-butylphenyl)piperazin-1-yl)butan-1-amine, CDI and 2,3,4,9-tetrahydro-1H-pyrido[3,4-b]indole as described in Example 1. Yield: 31%. mp 248-250° C. TLC R$_f$ 0.42 (CHCl$_3$-MeOH, 92.5:7.5); $^1$H NMR (DMSO-d$_6$) δ 1.25 (s, 18H), 1.45 (bs, 4H), 2.30 (t, 2H), 2.45 (t, 4H), 2.67 (t, 2H), 3.04-3.09 (m, 6H), 3.66 (t, 2H), 4.54 (s, 2H), 6.66 (t, 1H), 6.70 (d, J=1.5 Hz, 1H), 6.85 (t, 1H), 6.91-6.96 (m, 1H), 6.99-7.04 (m, 1H), 7.28 (d, J=8.3 Hz, 1H), 7.36 (d, J=7.8 Hz, 1H), 10.80 (s, 1H); ESI MS m/z 544 (MH)$^+$. Anal. (C$_{34}$H$_{49}$N$_5$O—H$_2$O) Calcd: 72.69; H, 9.15; N, 12.47. Found: C, 72.85; H, 8.91; N, 12.55.

EXAMPLE 98

N-(4-(4-(6-(tert-Butyl)-2-methylpyrimidin-4-yl)piperazin-1-yl)butyl)-8-(trifluoromethyl)-3,4-dihydro-1H-pyrido[4,3-b]indole-2(5H)-carboxamide (98). Prepared from 4-(4-(6-(tert-butyl)-2-methylpyrimidin-4-yl)piperazin-1-yl)butan-1-amine, CDI and 8-(trifluoromethyl)-2,3,4,5-tetrahydro-1H-pyrido[4,3-b]indole as described in Example 1. Yield: 34%. mp 85-87° C. TLC R$_f$ 0.17 (CHCl$_3$-MeOH, 92.5:7.5); $^1$H NMR (DMSO-d$_6$) δ 1.22 (s, 9H), 1.45 (bs, 4H), 2.29 (bs, 2H), 2.34 (s, 3H), 2.38 (t, 4H), 2.78 (t, 2H), 3.08 (bq, 2H), 3.56 (t, 4H), 3.71 (t, 2H), 4.5 (s, 2H), 6.47 (s, 1H), 6.58 (t, 1H), 7.31 (dd, J=8.6, 8.6 Hz, 1H), 7.47 (d, J=8.4 Hz, 1H), 7.73 (s, 1H), 11.36 (s, 1H); ESI MS m/z 572 (MH)$^+$. Anal. (C$_{30}$H$_{40}$F3 N$_7$O.0.25H$_2$O) Calcd: C, 62.54; H, 7.09; N, 17.02. Found: C, 62.45; H, 7.13; N, 16.78.

EXAMPLE 99

4-Phenyl-N-(4-(4-(2-(trifluoromethyl)quinolin-4-yl)piperazin-1-yl)butyl)piperazine-1-carboxamide (99). Prepared from 4-(4-(2-(trifluoromethyl)quinolin-4-yl)piperazin-1-yl)butan-1-amine, CDI and 1-phenylpiperazine as described in Example 1. Yield: 22%. mp 201-203° C. TLC R$_f$ 0.50 (CHCl$_3$-MeOH, 90:10); $^1$H NMR (DMSO-d$_6$), δ 1.47 (bs, 4H), 2.39 (t, 2H), 2 65 (t, 4H), 3.07 (t, 6H), 3.30 (bs, 4H), 3.43 (t, 4H), 6.58 (t, 1H), 6.78 (t, 1H), 6.94 (d, J=8.0 Hz, 2H), 7.18-7.24 (m, 3H), 7.66-7.71 (m, 1H), 7.81-7.86 (m, 1H), 8.05-8.09 (m, 2H); ESI MS m/z 541 (MH)$^+$. Anal. (C$_{29}$H$_{35}$F$_3$N$_6$O) Calcd: C, 64.42; H, 6.53; N, 15.55. Found: 64.03; H, 6.45; N, 15.55.

EXAMPLE 100

4-Phenyl-N-(4-(4-(2-(trifluoromethyl)quinolin-4-yl)piperazin-1-yl)butyl)piperidine-1-carboxamide (100). Prepared from 4-(4-(2-(trifluoromethyl)quinolin-4-yl)piperazin-1-yl)butan-1-amine, CDI and 4-phenylpiperidine as described in Example 1. Yield: 26%. mp 201-203° C. TLC R$_f$ 0.58 (CHCl$_3$-MeOH, 90:10); $^1$H NMR (DMSO-d$_6$) δ 1.41-1.51 (m, 6H), 1.70-1.74 (m, 2H), 2.41 (t, 2H), 2.62-2.76 (m, 7H), 3.07 (bq, 2H), 3.14 (bs, 4H), 4.08 (d, J=13.3 Hz, 2H), 6.47 (t, 1H), 7.14-7.30 (m, 6H), 7.69 (t, 1H), 7.81-7.89 (m, 1H), 8.05-8.09 (m, 2H). ESI MS m/z 540 (MH)$^+$. Anal. (C$_{30}$H$_{36}$F$_3$ N$_5$O.H$_2$O) Calcd: C, 64.62; H, 6.41; N, 12.56. Found: 64.72; H, 6.41; N, 12.77.

EXAMPLE 101

N-(4-(4-(2-(tert-Butyl)-6-cyclopropylpyrimidin-4-yl)piperazin-1-yl)butyl)-1,3,4,9-tetrahydro-2H-pyrido[3,4-b]indole-2-carboxamide (101). Prepared from 4-(4-(2-(tert-butyl)-6-cyclopropylpyrimidin-4-yl)piperazin-1-yl)butan-1-amine, CDI and 2,3,4,9-tetrahydro-1H-pyrido[3,4-b]indole as described in Example 1. Yield: 33%. mp 118-120° C. TLC R$_f$ 0.44 (CHCl$_3$-MeOH, 92.5:7.5); $^1$H NMR (DMSO-d$_6$) δ 0.83-0.89 and 0.91-0.95 (2m, 4H), 1.21 (s, 9H), 1.45 (bs, 4H), 1.83-1.90 (m, 1H), 2.28 (t, 2H), 2.36 (t, 4H), 2.66 (t, 2H), 3.04-3.09 (bq, 2H), 3.53 (t, 4H), 3.65 (t, 2H), 4.54 (s, 2H), 6.46 (s, 1H), 6.66 (t, 1H), 6.92-6.96 (m, 1H), 6.99-7.04 (m, 1H), 7.28 (d, J=7.8 Hz, 1H), 7.37 (d, J=8.9 Hz, 1H), 10.80 (s, 1H); ESI MS m/z 530 (MH)$^+$. Anal. ($C_{31}H_{43}N_7O$) Calcd: 70.29; H, 8.18; N, 18.51. Found: C, 69.96; H, 8.02; N, 18.53.

EXAMPLE 102

N-(4-(4-(2-(tert-Butyl)-6-(trifluoromethyl)pyrimidin-4-yl)piperazin-1-yl)butyl)-3-oxo-4-phenylpiperazine-1-carboxamide (102). Prepared from 4-(4-(2-(tert-butyl)-6-(trifluoromethyl)pyrimidin-4-yl)piperazin-1-yl)butan-1-amine, CDI and 1-phenylpiperazin-2-one as described in Example 1. Yield: 27%. mp 56-59° C. TLC R$_f$ 0.58 (CHCl$_3$-MeOH, 90:10); $^1$H NMR (DMSO-d$_6$) δ 1.28 (s, 9H), 1.46 (bs, 4H), 2.32 (t, 2H), 2.43 (t, 4H), 3.07 (bq, 2H), 3.66-3.72 (m, 8H), 4.09 (s, 2H), 6.64 (t, 1H), 7.03 (s, 1H), 7.03-7.33 (m, 1H), 7.34-7.38 (m, 2H), 7.39-7.42 (m, 2H); ESI MS m/z 562 (MH)$^+$. Anal. ($C_{28}H_{38}F_3N_7O.0.25H_2O$) Calcd: C, 59.40; H, 6.85; N, 17.32. Found: C, 59.21; H, 6.74; N, 17.12.

EXAMPLE 103

N-(4-(4-(2-(tert-Butyl)-6-(trifluoromethyl)pyrimidin-4-yl)piperazin-1-yl)butyl)-4-phenylcyclohexanecarboxamide (103). To a solution of 4-phenylcycloxhexanecarboxylic acid (0.204 g, 1.0 mmol) in dichloromethane (10 mL) was added bis(2-oxo-3-oxazolidinyl)phosphinic chloride (BOP-Cl) (0.254 g, 1.0 mmol) and the mixture was stirred at room temperature for 4 hours. Triethylamine (0.46 mL, 3.0 mmol) and 4-(4-(2-(tert-butyl)-6-(trifluoromethyl)pyrimidin-4-yl)piperazin-1-yl)butan-1-amine (0.318 g, 1.0 mmol) were added and the mixture was stirred at room temperature overnight. The reaction mixture was concentrated under reduced pressure and the residue was partitioned between EtOAc and water. The organic layers were dried over anhydrous sodium sulfate, filtered and the filtrate was evaporated under reduced pressure. The residue obtained was purified by column chromatography over silica using EtOAc-MeOH (10:1) as the eluent to yield 0.165 g (30%) of the desired product. mp 137-139° C. TLC R$_f$ 0.69 (CHCl$_3$-MeOH, 92.5:7.5); $^1$H NMR (DMSO-d$_6$) δ 1.28 (s, 9H), 1.37-1.55 (m, 8H), 1.78-1.86 (m, 4H), 2.11-2.19 (m, 1H), 2.31 (t, 2H), 2.42 (t, 4H), 2.49-2.51 (m, 1H), 3.06 (dd, J=11.9, 11.7 Hz, 2H), 3.71 (bs, 4H), 7.04 (s, 1H), 7.13-7.31 (m, 5H), 7.71 (t, 1H); ESI MS m/z 546 (MH)$^+$. Anal. ($C_{30}H_{42}F_3N_5O.0.25H_2O$) Calcd: C, 65.49; H, 7.78; N, 12.73. Found: C, 65.46; H, 7.57; N, 12.20.

EXAMPLE 104

4-Phenyl-N-(4-(4-(quinolin-4-yl)piperazin-1-yl)butyl)cyclohexanecarboxamide (104). Prepared from 4-phenylcycloxhexanecarboxylic acid and 4-(4-(quinolin-4-yl)piperazin-1-yl)butan-1-amine in a similar fashion as described in Example 103. Yield: 30%. mp 132-134° C. TLC R$_f$ 0.60 (CHCl$_3$-MeOH, 92.5:7.5); $^1$H NMR (DMSO-d$_6$) δ 1.36-1.48 (m, 8H), 1.78-1.88 (m, 4H), 2.10-2.12 (m, 1H), 2.40 (t, 2H), 2.48-2.51 (m, 1H), 2.65 (bs, 4H), 3.07 (dd, J=12.0, 11.9 Hz, 2H), 3.16 (bs, 4H), 6.97 (d, J=5.1 Hz, 1H), 7.11-7.32 (m, 5H), 7.15-7.66 (m, 1H), 7.63-7.75 (m, 2H), 7.3 (d, J=8.4 Hz, 1H), 7.99 (d, J=8.4 Hz, 1H), 8.67 (d, J=4.8 Hz, 1H); ESI MS m/z 471 (MH)$^+$. Anal. ($C_{30}H_{38}N_4O.5H_2O$) Calcd: C, 75.12; H, 8.20; N, 11.68. Found: C, 74.92; H, 7.89; N, 11.51.

EXAMPLE 105

N-(4-(4-(7-Chloroquinolin-4-yl)piperazin-1-yl)butyl)-4-phenylcyclohexanecarboxamide (105). Prepared from 4-phenylcycloxhexanecarboxylic acid and 4-(4-(7-chloroquinolin-4-yl)piperazin-1-yl)butan-1-amine in a similar fashion as described in Example 103. Yield: 21%. mp 169-170° C. TLC R$_f$ 0.58 (CHCl$_3$-MeOH, 92.5:7.5); $^1$H NMR (DMSO-d$_6$) δ 1.38-1.58 (m, 8H), 1.81-1.86 (m, 4H), 2.12-2.19 (m, 1H), 2.39 (t, 2H), 2.48-2.54 (m, 2H), 2.65 (bs, 4H), 3.07 (dd, J=12.0, 11.9 Hz, 2H), 3.18 (bs, 4H), 6.99-7.01 (d, J=5.1 Hz, 1H), 7.12-7.32 (m, 5H), 7.54-7.59 (m, 1H), 7.72 (t, 1H), 7.97 (d, J=2.3. Hz, 1H), 8.01 (d, J=9.0 Hz, 1H), 8.69 (d, J=5.1 Hz, 1H); ESI MS m/z 505 (MH)$^+$. Anal. ($C_{30}H_{37}N_4ClO$) Calcd: C, 71.34; H, 7.34; N, 11.09. Found: C, 70.94; H, 7.21; N, 10.90.

EXAMPLE 106

4-Phenyl-N-(4-(4-(quinolin-2-yl)piperazin-1-yl)butyl)cyclohexanecarboxamide (106). Prepared from 4-phenylcycloxhexanecarboxylic acid and 4-(4-(quinolin-2-yl)piperazin-1-yl)butan-1-amine as described in Example 103. Yield: 21%. mp 156-159° C. TLC R$_f$ 0.59 (CHCl$_3$-MeOH, 92.5:7.5); $^1$H NMR (DMSO-d$_6$) δ 1.36-1.49 (m, 8H), 1.80-1.86 (m, 4H), 2.10-2.21 (m, 1H), 2.32 (t, 2H), 2.48-2.54 (m, 6H), 3.06 (dd, J=12.0, 11.9 Hz, 2H), 3.67 (bs, 4H), 7.09-7.32 (m, 6H), 7.48-7.57 (m, 2H), 7.65-7.76 (m, 2H), 8.01 (d, J=9.1 Hz, 1H); ESI MS m/z 471 (MH)$^+$. Anal. ($C_{30}H_{38}N_4O.5H_2O$) Calcd: C, 75.12; H, 8.20; N, 11.68. Found: C, 75.12; H, 7.81; N, 11.70.

EXAMPLE 107

N-(4-(4-(2-(tert-Butyl)-6-methylpyrimidin-4-yl)piperazin-1-yl)butyl)-1-(5-(trifluoromethyl)pyridin-2-yl)piperidine-4-carboxamide (107). To a solution of 1-(5-(trifluoromethyl)pyridin-2-yl)piperidine-4-carboxylic acid (0.150 g, 0.5 mmol) in acetonitrile (10 mL) was added O-(7-azabenzotriazol-1-yl)-N,N,N',N'-tetramethyluronium hexafluorophosphate (HATU) (0.190 g, 0.5 mmol) and the mixture was stirred at room temperature for 15 minutes. Triethylamine (0.26 mL, 1.5 mmol) and 4-(4-(2-(tert-butyl)-6-methylpyrimidin-4-yl)piperazin-1-yl)butan-1-amine (0.345 g, 0.5 mmol) were then added and the mixture was stirred at room temperature overnight. The mixture was then concentrated under reduced pressure, the residue obtained was dissolved in chloroform and washed with saturated aqueous sodium bicarbonate. The organic layer was separated, dried over anhydrous sodium sulfate, filtered and the solvent was removed under reduced pressure. The crude product thus obtained was purified by chromatography over a column of silica using CHCl$_3$-MeOH (96:4) as the eluent to obtain 0.161 g (29%) of the desired product. Yield: 29%. mp 134-135° C. TLC R$_f$ 0.37 (CHCl$_3$-MeOH, 92.5:7.5); $^1$HNMR (DMSO-d$_6$) δ 1.27 (s, 9H), 1.41-1.58 (m, 6H), 1.71 (dd, J=13.3, 12.9 Hz, 2H), 2.38 (s, 3H), 2.28 (t, 2H), 2.40 (t, 4H), 2.40-242 (m, 1H), 2.91-3.08 (m, 4H), 3.56 (t, 4H), 4.38 (d, J=13.3 Hz, 2H), 6.46 (s, 1H), 6.94 (d, J=9.3 Hz, 1H), 7.73 (dd, J=9.3, 9.0 Hz, 1H), 7.79 (t, 1H), 8.39 (s, 1H); ESI MS m/z 562 (MH)$^+$. Anal. ($C_{29}H_{42}F_3N_7O.75H_2O$) Calcd: C, 60.56; H, 7.62; N, 17.05. Found: C, 60.57; H, 7.66; N, 16.96.

EXAMPLE 108

N-(4-(4-(2-(tert-Butyl)-6-(trifluoromethyl)pyrimidin-4-yl)piperazin-1-yl)butyl)-1-phenylpiperidine-4-carboxamide (108). Prepared from 1-phenylpiperidine-4-carboxylic acid and 4-(4-(2-(tert-butyl)-6-(trifluoromethyl)pyrimidin-4-yl)piperazin-1-yl)butan-1-amine as described in Example 103. Yield: 26%. mp 178-180° C. TLC R$_f$ 0.30 (CHCl$_3$-MeOH, 92.5:7.5); ¹H NMR (DMSO-d₆) δ 1.28 (s, 9H), 1.42-1.46 (m, 4H), 1.58-1.77 (m, 4H), 2.22-2.35 (m, 3H), 2.42 (t, 4H), 2.61-2.69 (m, 2H), 3.06 (dd, J=11.7, 11.7 Hz, 2H), 3.66-3.72 (m, 6H), 6.71-6.77 (m, 1H), 6.91-6.94 (m, 2H), 7.04 (s, 1H), 7.16-7.22 (m, 2H), 7.79 (t, 1H); ESI MS m/z 547 (MH)⁺. Anal. (C₂₉H₄₁F₃N₆O.25H₂O) Calcd: C, 63.20; H, 7.59; N, 15.25. Found: C, 62.97; H, 7.42; N, 15.09.

EXAMPLE 109

1-Benzyl-N-(4-(4-(2-(tert-Butyl)-6-(trifluoromethyl)pyrimidin-4-yl)piperazin-1-yl)butyl)piperidine-4-carboxamide (109). Prepared from 1-benzylpiperidine-4-carboxylic acid and 4-(4-(2-(tert-butyl)-6-(trifluoromethyl)pyrimidin-4-yl)piperazin-1-yl)butan-1-amine in a similar fashion as described in Example 103. Yield: 41%. mp 36-37° C. TLC R$_f$ 0.49 (CHCl₃-MeOH, 92.5:7.5); ¹HNMR (DMSO-d₆) δ 1.28 (s, 9H), 1.36-1.47 (m, 4H), 1.54-1.68 (m, 2H), 1.84-1.93 (m,2H), 2.07-2.11 (m, 2H), 2.29 (t, 2H), 2.40 (t, 2H), 2.78 (d, J=11.6 Hz, 4H), 3.02 (dd, J=11.8, 11.6 Hz, 2H), 3.42 (s, 2H), 3.6-3.88 (bs, 4H), 7.03 (s, 1H), 7.22-7.33 (m, 5H), 7.69 (t, 1H); ESI MS m/z 561 (MH)⁺. Anal. (C₃₀H₄₃F₃N₆O.H₂O) Calcd: C, 62.26; H, 7.84; N, 14.50. Found: C, 62.23; H, 7.65; N, 14.86.

EXAMPLE 110

N-(4-(4-(2-(tert-Butyl)-6-(trifluoromethyl)pyrimidin-4-yl)piperazin-1-yl)butyl)-1-(5-(trifluoromethyl)pyridin-2-yl)piperidine-4-carboxamide (110). Prepared from 1-(5-(trifluoromethyl)pyridin-2-yl)piperidine-4-carboxylic acid and 4-(4-(2-(tert-butyl)-6-(trifluoromethyl)pyrimidin-4-yl)piperazin-1-yl)butan-1-amine in a similar fashion as described in Example 107. Yield: 30%. mp 132-134° C. TLC R$_f$ 0.44 (CHCl₃-MeOH, 92.5:7.5); ¹H NMR (DMSO-d₆) δ 1.26 (s, 9H), 1.42-1.48 (m, 4H), 1.49-1.58 (m, 2H), 1.71 (dd, J=12.9, 12.3 Hz, 2H), 2.29 (t, 2H), 2.42 (t, 4H), 2.90-2.99 (m, 2H), 3.01-3.08 (m, 2H), 3.70 (bs, 4H), 4.32-4.45 (m, 2H), 6.94 (d, J=9.0 Hz, 1H), 7.03 (s, 1H), 7.74 (dd, J=2.7, 2.4 Hz, 1H), 7.79 (t,1H), 8.39 (dd, J=0.7 and 0.8 Hz, 1H); ESI MS m/z 616 (MH)⁺. Anal. (C₂₉H₃₉F₃N₇O) Calcd: C, 56.58; H, 6.39; N, 15.93. Found: C, 56.55; H, 6.33; N, 15.71.

EXAMPLE 111

N-(4-(4-(2-(tert-Butyl)-6-methylpyrimidin-4-yl)piperazin-1-yl)butyl)imidazo[1,2-a]pyridine-2-carboxamide (111). To a solution of imidazo[1,2-a]pyridine-2-carboxylic acid, (0.162 g, 1.0 mmol) in acetonitrile (10 mL) was added O-(7-azabenzotriazol-1-yl)-N,N,N',N'-tetramethyluronium hexafluorophosphate (HATU) (0.38 g, 1.0 mmol) and the mixture was stirred at room temperature for 15 minutes. Triethylamine (0.46 mL, 3.0 mmol) and 4-(4-(2-(tert-butyl)-6-methylpyrimidin-4-yl)piperazin-1-yl)butan-1-amine (0.305 g, 1.0 mmol) were then added and the mixture was stirred at room temperature overnight. The mixture was then concentrated under reduced pressure, the residue obtained was dissolved in chloroform and washed with saturated aqueous sodium bicarbonate. The organic layer was separated, dried over anhydrous sodium sulfate, filtered and the solvent was removed under reduced pressure. The crude product thus obtained was purified by chromatography over a column of silica using CHCl₃-MeOH (96:4) as the eluent to obtain 0.089 g (20%) of the desired product as colorless oil. TLC R$_f$ 0.17 (CHCl₃-MeOH, 95:5); ¹H NMR (DMSO-d₆) δ 1.25 (s, 9H), 1.44-1.60 (m, 4H), 2.23 (s, 3H), 2.23-2.46 (m, 6H), 3.24-3.44 (m, 2H), 3.58 (bs, 4H), 6.47 (s, 1H), 6.97 (td, 1H), 7.37 (td, 1H), 7.56 (dd, J=9.4, 9.0 Hz, 1H), 8.34 (s, 1H), 8.37 (t, 1H), 8.56 (dt, 1H). ESI MS m/z 450 (MH)⁺. Anal. (C₂₅H₃₅N₇O—H₂O) Calcd: C, 64.21; H, 7.98; N, 20.97. Found: C, 64.53; H, 7.64; N, 20.94.

EXAMPLE 112

N-(4-(4-(2-(tert-Butyl)-6-cyclopropylpyrimidin-4-yl)piperazin-1-yl)butyl)imidazo[1,2-a]pyridine-2-carboxamide (112). Prepared from imidazo[1,2-a]pyridine-2-carboxylic acid and 4-(4-(2-(tert-butyl)-6-cyclopropylpyrimidin-4-yl)piperazin-1-yl)butan-1-amine in a similar fashion as described in Example 111. Yield: 36%. mp 34-37° C. TLC R$_f$ 0.19 (CHCl₃-MeOH, 95:5); ¹HNMR (DMSO-d₆) δ 0.81-0.96 (2m, 4H), 1.28 (s, 9H), 1.45-1.60 (m, 4H), 1.84-1.90 (m, 1H), 2.32 (t, 2H), 2.40 (t, 4H), 3.27-3.33 (m, 2H), 3.58 (t, 4H), 6.49 (s, 1H), 6.97 (td, 1H), 7.32 (td, 1H), 7.56 (dd, J=9.4 and 9.0 Hz, 1H), 8.37 (t, 2H), 8.56 (dt, 1H). ESI MS m/z 490 (MH)⁺. Anal. (C₂₇H₃₇N₇O—H₂O) Calcd: C, 65.69; H, 7.96; N, 19.86. Found: C, 65.68; H, 7.86; N, 19.49.

EXAMPLE 113

N-(4-(4-(2-(tert-Butyl)-6-(trifluoromethyl)pyrimidin-4-yl)piperazin-1-yl)butyl)imidazo[1,2-a]pyridine-2-carboxamide (113). To a solution of imidazo[1,2-a]pyridine-2-carboxylic acid (5.89 g, 36.60 mmol) in dichloromethane (350 mL) was added bis(2-oxo-3-oxazolidinyl)phosphinic chloride (BOP-Cl) (9.3 g, 36.6 mmol) and the mixture was stirred at room temperature for 4 hours. Triethylamine (15.0 mL) and 4-(4-(2-(tert-butyl)-6-(trifluoromethyl)pyrimidin-4-yl)piperazin-1-yl)butan-1-amine (13.14 g, 36.6 mmol) were added and the mixture was stirred at room temperature overnight. The reaction mixture was concentrated under reduced pressure and the residue was partitioned between EtOAc and water. The organic layers were dried over anhydrous sodium sulfate, filtered and the filtrate was evaporated under reduced pressure. The residue obtained was purified by column chromatography over silica using EtOAc-MeOH (10:1) as the eluent to yield 6.0 g (32%) of the desired product. A solution of the free base in ether was treated with 1.0 molar solution of HCl in diethyl ether to obtain the dihydrochloride salt. mp 253-255° C. TLC R$_f$ 0.29 (CHCl₃-MeOH, 90:10); ¹H NMR (DMSO-d₆) δ 1.31 (s, 9H), 1.62-1.69 (m, 2H), 1.80-1.88 (m, 2H), 2.88-3.19 (broad hump, 1H), 3.10-3.17 (m, 2H), 3.37-3.33 (q, 2H), 3.52-3.60 (m, 4H), 4.32-4.86 (b, 2H), 7.11 (s, 1H), 7.13-7.18 (m, 1H), 7.50-7.57 (t, 1H), 7.65 (dd, J=9.2, 9.0 Hz, 1H), 8.53 (s, 1H), 8.57 (bs, 1H), 8.68 (d, J=6.9 Hz, 1H), 11.0-11.8 (b, 1H). ESI MS m/z 504 (MH)⁺. Anal. (C₂₅H₃₂F₃N₇O.2HCl.0.25H₂O) Calcd: C, 51.68; H, 5.98; N, 16.87; Cl, 12.20. Found: C, 51.64; H, 6.00; N, 16.89; Cl, 11.97.

EXAMPLE 114

N-(4-(4-(2-(tert-Butyl)-6-(trifluoromethyl)pyrimidin-4-yl)piperazin-1-yl)butyl)imidazo[1,2-a]pyrimidine-2-carboxamide (114). Prepared from imidazo[1,2-a]pyrimidine-2-carboxylic acid and 4-(4-(2-(tert-butyl)-6-(trifluoromethyl)pyrimidin-4-yl)piperazin-1-yl)butan-1-amine in a similar fashion as described for 113. The compound was isolated and characterized as the free base. Yield: 49%. mp 136-138° C. TLC R$_f$ 0.47 (CHCl₃-MeOH, 95:5); ¹H NMR (DMSO-d₆) δ 1.8 (s, 9H), 1.37-1.57 (m, 4H), 2.24 (t, J=5.96 Hz, 2H), 2.44-2.48 (m, 4H), 2.98-3.06 (m, 2H), 3.21-3.26 (m, 2H), 3.62 (bs, 2H), 7.03 (s, 1H), 7.15 (dd, J=6.92, 6.91 Hz, 1H), 8.29 (s, 1H), 8.57 (t, 1H), 8.63 (d d, J=4.05 and 4.18 Hz, 1H), 8.98 (dd, J=6.91 and 6.81 Hz, 1H). ESI MS m/z 505 (MH)⁺. Anal. (C$_{24}$H$_{31}$F$_3$N$_8$O—H$_2$O) Calcd: C, 55.16; H, 6.36; N, 21.44. Found: C, 55.19; H, 6.02; N, 21.29.

EXAMPLE 115

N-(4-(4-(2-(tert-Butyl)-6-(trifluoromethyl)pyrimidin-4-yl)piperazin-1-yl)butyl)imidazo[1,2-a]pyrazine-2-carboxamide (115). Prepared from imidazo[1,2-a]pyrazine-2-carboxylic acid and 4-(4-(2-(tert-butyl)-6-(trifluoromethyl)pyrimidin-4-yl)piperazin-1-yl)butan-1-amine in a similar fashion as described in Example 113. Yield: 39%. mp 200-202° C. TLC R$_f$ 0.25 (CHCl$_3$-MeOH, 95:5); ¹H NMR (DMSO-d$_6$) δ 1.28 (s, 9H), 1.47-1.67 (m, 4H), 2.32 (t, J=5.96 Hz, 2H), 2.44-2.48 (m, 4H), 3.21-3.36 (m, 2H), 3.71 (bs, 4H), 7.04 (s, 1H), 7.95 (d, J=4.66 Hz, 1H), 8.50 (s, 1H), 8.61-8.66 (m, 2H), 9.12 (d, J=0.77 Hz, 1H). ESI MS m/z 505 (MH)⁺. Anal. (C$_{24}$H$_{31}$F$_3$N$_8$O.2HCl) Calcd: C, 48.78; H, 5.88; N, 18.96. Found: C, 48.64; H, 5.66; N. 18.58.

EXAMPLE 116

N-(4-(4-(2-(tert-Butyl)-6-(trifluoromethyl)pyrimidin-4-yl)piperazin-1-yl)butyl)-6-chloroimidazo[1,2-b]pyridazine-2-carboxamide (116). Prepared from 6-chloroimidazo[1,2-b]pyridazine-2-carboxylic acid and 4-(4-(2-(tert-butyl)-6-(trifluoromethyl)pyrimidin-4-yl)piperazin-1-yl)butan-1-amine in a similar fashion as described in Example 113. Yield: 15%. mp 119-121° C. TLC R$_f$ 0.59 (CHCl$_3$-MeOH, 95:5); ¹H NMR (DMSO-d$_6$) δ 1.27 (s, 9H), 1.43-1.62 (m, 4H), 2.29 (t, J=4.63 Hz, 2H), 2.45 (t, J=1.81 Hz, 4H), 3.34 (bs, 2H), 3.62 (bs, 4H), 7.03 (s, 1H), 7.46 (d, J=9.56 Hz, 1H), 8.23 (dd, J=9.61, 9.56 Hz, 1H), 8.54 (t, J=5.96 Hz, 1H), 8.67 (d, J=0.65 Hz, 1H). ESI MS m/z 539 (MH)⁺. Anal. (C$_{24}$H$_{30}$F$_3$ClN$_8$O$_2$.0.5H$_2$O) Calcd: C, 52.60H, 5.70; N, 20.45. Found: C, 52.37; H, 5.47; N, 20.69.

EXAMPLE 117

N-(4-(4-(Quinolin-4-yl)piperazin-1-yl)butyl)imidazo[1,2-a]pyridine-2-carboxamide (117). Prepared from imidazo[1,2-a]pyridine-2-carboxylic acid and 4-(4-(quinolin-4-yl)piperazin-1-yl)butan-1-amine in a similar fashion as described in Example 113. Yield: 11%. mp 126-128° C. TLC R$_f$ 0.09 (CHCl$_3$-MeOH, 95:5); ¹HNMR (DMSO-d$_6$) δ 1.46-1.65 (m, 4H), 2.38-2.47 (m, 2H), 2.65 (bs, 4H), 3.18 (bs, 4H), 3.26-3.39 (m, 2H), 6.95 (d, J=5.27 Hz, 1H), 6.99 (d, J=1.99 Hz, 1H), 7.28-7.39 (m, 1H), 7.50-7.60 (m, 2H), 7.62-7.72 (m, 1H), 7.92 (dd, J=8.35, 8.34 Hz, 1H), 7.99 (d, J=7.42 Hz, 1H), 8.35 (s, 1H), 8.35 (t, J=5.93 Hz, 1H), 8.57 (d, J=6.92 Hz, 1H), 8.66 (d, J=4.94 Hz, 1H); ESI MS m/z 429 (MH)⁺. Anal. (C$_{25}$H$_{28}$N$_6$O.0.25H$_2$O) Calcd: C, 69.34; H, 6.64; N, 19.41. Found: C, 69.61; H, 6.36; N, 19.17.

EXAMPLE 118

N-(4-(4-(7-Chloroquinolin-4-yl)piperazin-1-yl)butyl)imidazo[1,2-a]pyridine-2-carboxamide (118). Prepared from imidazo[1,2-a]pyridine-2-carboxylic acid and 4-(4-(7-chloroquinolin-4-yl)piperazin-1-yl)butan-1-amine in a similar fashion as described in Example 113. Yield: 28%. mp 155-157° C. TLC R$_f$ 0.67 (CHCl$_3$-MeOH, 85:15); ¹H NMR (DMSO-d$_6$) δ 1.47-1.65 (m, 4H), 2.42 (t, 2H), 2.62-1-2.72 (bs, 4H), 3.14-3.23 (bs, 2H), 3.27-3.46 (m, 4H), 6.96 (d, J=3.1 Hz, 1H), 6.98-7.18 (m, 1H), 7.28-7.34 (m, 1H), 7.50-7.56 (m, 2H), 7.96 (d, J=2.2 Hz, 1H), 8.00 (d, J=9.0 Hz, 1H), 8.34 (s, 1H), 8.38 (t, 1H), 8.58-8.62 (m, 1H), 8.69 (d, J=4.9 Hz, 1H); ESI MS m/z 463 (MH)⁺. Anal. (C$_{25}$H$_{27}$ClN$_6$O.0.25H$_2$O) Calcd: C, 64.23; H, 5.93; N, 17.98. Found: C, 64.12; H, 5.68; N, 17.87.

EXAMPLE 119

N-(4-(4-(2-(tert-Butyl)-6-(trifluoromethyl)pyrimidin-4-yl)piperazin-1-yl)butyl)-5-(hydroxymethyl)imidazo[1,2-a]pyridine-2-carboxamide (119). Step 1. A solution of 2-amino-6-hydroxymethylpyridine (5.0 g, 40.32 mmol) and ethyl 3-bromopyruvate (1.58 g, 80.64 mmol) in ethanol (150 mL) was stirred with heating under reflux for 3 hours. The reaction mixture was cooled down to room temperature and concentrated under reduced pressure. The residue obtained was purified by chromatography over a column of silica using hexane-EtOAc (75:25) to yield 6.2 g (70%) of ethyl 5-(hydroxymethyl)imidazo[1,2-a]pyridine-2-carboxylate. ESI MS m/z 221 (MH)⁺.

Step 2. To a stirred solution of the above compound (3.89 g, 17.69 mmol) and imidazole (3.5 g, 35.4 mmol) in DMF (12 mL) was added chlorotriisopropylsilane (6.82 g, 35.4 mmol) dropwise and the reaction mixture was heated at 70° C. for 2 hours. After cooling to room temperature, the reaction mixture was diluted with EtOAc (200 mL) and washed with saturated aqueous sodium carbonate (150 mL). The organic phase was washed with brine, dried over sodium sulfate and concentrated under reduced pressure. The residue thus obtained was purified by silica gel column using CH$_2$Cl$_2$-EtOAc (1:1) as the eluant to obtain 4.8 g (72%) of ethyl 5-(((triisopropylsilyl)oxy)methyl)imidazo[1,2-a]pyridine-2-carboxylate. ESI MS m/z 377 (MH)⁺.

Step 3. To a solution of the above silyl ether 4.8 g (127 mmol) in 50 mL of methanol/THF/water (2:2:1) was added NaOH (2.1 g). The mixture was stirred at room temperature for 2 hours. The mixture was neutralized by the addition of acetic acid and the solvents were removed under reduced pressure. The residue obtained was purified over a column of silica using CH$_2$Cl$_2$-MeOH (7:1) to give 3.6 g (71%) of 5-(((triisopropylsilyl)oxy)methyl)imidazo[1,2-a]pyridine-2-carboxylic acid. ESI MS m/z 349 (MH)⁺.

Step 4. To a solution of the above acid (1.02 g, 2.92 mmol) in acetonitrile (15 mL) was added HATU (1.11 g, 2.92 mmol) and Et$_3$N (0.6 mL, 4.38 mmol). The mixture was stirred for 10 minutes and 4-(4-(2-(tert-butyl)-6-methylpyrimidin-4-yl)piperazin-1-yl)butan-1-amine (1.05 g, 2.92 mmol) was added and the stirring was continued overnight at room temperature. The reaction mixture was then concentrated under reduced pressure and the residue was washed with aqueous sodium bicarbonate and dried over anhydrous sodium sulfate. Filtration and removal of the solvent gave the crude product which was purified by chromatography over a column of silica using CHCl$_3$-MeOH (97:3) as the eluent to obtain 0.45 g (23%) of N-(4-(4-(2-(tert-butyl)-6-(trifluoromethyl)pyrimidin-4-yl)piperazin-1-yl)butyl)-5-(((triisopropylsilyl)oxy)methyl)imidazo[1,2-a]pyridine-2-carboxamide.

Step 5. To a solution of the above compound 0.45 g (0.65 mmol) in THF (20 mL) tetraethyl ammonium fluoride (0.146 g, 0.98 mmol) was added and the mixture was stirred at room temperature overnight. The mixture was then concentrated and partitioned between CHCl$_3$ and water. The organic layer was separated, dried over anhydrous sodium sulfate, filtered and the solvent was removed under reduced pressure. The residue thus obtained was purified by chromatography over a column of silica using CHCl$_3$-MeOH (92:8) as the eluent to obtain the desired product to yield 0.216 g (62%) of the desired product as colorless oil. TLC $R_f$ 0.46 (CHCl$_3$-MeOH, 92.5:7.5); $^1$H NMR (DMSO-d$_6$) δ 1.28 (s, 9H), 1.41-1.60 (m, 4H), 2.34 (t, 2H), 2.44 (t, 4H), 3.01-3.28 (m, 2H), 3.70 (bs, 4H), 4.78 (d, J=7.8 Hz, 2H), 5.71-5.78 (m, 1H), 6.94 (dd, J=6.6, 6.6 Hz, 1H), 7.03 (s, 1H), 7.30-7.40 (m, 1H), 7.53 (d, J=9.0 Hz, 1H), 8.28 (s, 1H), 8.40 (t, 1H); ESI MS m/z 534 (MH)$^+$. Anal. (C$_{26}$H$_{34}$F$_3$N$_7$O$_2$.75H$_2$O) Calcd: C, 57.08; H, 6.54; N, 17.92. Found: C, 57.15; H, 6.33; N, 17.53.

EXAMPLE 120

N-(4-(4-(2-(tert-Butyl)-6-(trifluoromethyl)pyrimidin-4-yl)piperazin-1-yl)butyl)-3-((dimethylamino)methyl)imidazo[1,2-a]pyridine-2-carboxamide (120). Prepared from 3-((dimethylamino)methyl)imidazo[1,2-a]pyridine-2-carboxylic acid and 4-(4-(2-(tert-butyl)-6-(trifluoromethyl)pyrimidin-4-yl)piperazin-1-yl)butan-1-amine in a similar fashion as described in Example 111. Yield: 38%. Colorless oil. TLC $R_f$ 0.38 (CHCl$_3$-MeOH, 95:5); $^1$HNMR (DMSO-d$_6$) δ 1.28 (s, 9H), 1.41-1.64 (m, 4H), 2.16 (s, 6H), 2.34 (t, 2H), 2.43 (t, 4H), 3.22-3.36 (m, 2H), 3.72 (bs, 4H), 4.17 (s, 2H), 6.92-7.05 (m, 2H),7.38 (t, 1H), 7.57 (d, J=9.0 Hz, 1H), 8.38 (t, 1H), 8.44 (d, J=6.7 Hz, 1H); ESI MS m/z 561 (MH)$^+$. Anal. (C$_{28}$H$_{39}$F$_3$N$_8$O.0.5H$_2$O) Calcd: C, 59.04; H, 7.06; N, 19.67. Found: C, 59.36; H, 6.88; N, 19.33.

EXAMPLE 121

N-(4-(4-(2-(tert-Butyl)-6-(trifluoromethyl)pyrimidin-4-yl)piperazin-1-yl)butyl)-5-((dimethylamino)methyl)imidazo[1,2-a]pyridine-2-carboxamide (121). A solution of N-(4-(4-(2-(tert-Butyl)-6-(trifluoromethyl)pyrimidin-4-yl)piperazin-1-yl)butyl)-5-(hydroxymethyl)imidazo[1,2-a]pyridine-2-carboxamide (0.125 g, 0.235 mmol) and triethylamine (0.98 mL, 0.702 mmol) in dichloromethane (5 mL) was cooled in ice bath and treated dropwise with methanesulfonyl chloride (0.15 g, 1.3 mmol). The mixture was allowed to warm to room temperature and stirred at room temperature for 1 hour. To the mixture was then added dimethylamine (0.25 mL of 1M solution in THF) and the mixture was stirred at room temperature for 6 hours. Volatiles were removed under reduced pressure and the residue was partitioned between CHCl$_3$ and saturated aqueous sodium bicarbonate. The organic layers were separated and dried over anhydrous sodium sulfate. Filtration, removal of the solvent under reduced pressure followed by purification by silica gel column chromatography using CHCl$_3$-MeOH (97:3) afforded 0.03 g (23%) of the desired product. mp 62-64° C. TLC $R_f$ 0.64 (CHCl$_3$-MeOH, 92.5:7.5); $^1$HNMR (DMSO-d$_6$) δ 1.28 (s, 9H), 1.44-1.61 (m, 4H), 2.21 (s, 6H), 2.34 (t, 2H), 2.43(t, 4H), 3.09-3.35 (m, 2H), 3.72 (bs, 4H), 3.76 (s, 2H), 6.93 (d, J=6.7 Hz, 1H), 7.03 (s, 1H), 7.26-7.34 (m, 1H), 7.55 (d, J=9.0 Hz, 1H), 8.31 (s, 1H), 8.39 (t, 1H); ESI MS m/z 560 (MH)$^+$. Anal. (C$_{28}$H$_{39}$F$_3$N$_8$O.H$_2$O) Calcd: C, 58.12; H, 7.14; N, 19.36, Found: C, 58.40; H, 7.00, N, 18.96.

EXAMPLE 122

N-(4-(4-(2,6-Di-tert-butylpyrimidin-4-yl)piperazin-1-yl)butyl)imidazo[1,2-a]pyridine-2-carboxamide (122). Prepared from imidazo[1,2-a]pyridine-2-carboxylic acid and 4-(4-(2,6-di-tert-butylpyrimidin-4-yl)piperazin-1-yl)butan-1-amine in a similar fashion as described in Example 111. Yield: 30%. mp 90-94° C. TLC $R_f$ 0.54 (CHCl$_3$-MeOH, 95:5); $^1$H NMR (DMSO-d$_6$) δ 1.24 (s, 9H), 1.27 (s, 9H), 1.45-1.60 (m, 4H), 2.33 (t, 2H), 2.41 (t, 4H), 3.28-3.34 (m, 2H), 3.60 (t, 4H), 6.45 (s, 1H), 6.96 (td, 1H), 7.33 (td, 1H), 7.58 (dd, J=9.4, 9.0 Hz, 1H), 8.34 (d, J=0.8 Hz, 1H), 8.38 (t, 1H) 8.57 (dt, 1H); ESI MS m/z 491 (MH)$^+$. Anal. (C$_{28}$H$_{41}$N$_7$O.0.75H$_2$O) Calcd: C, 66.57; H, 8.48; N, 19.40. Found: C, 66.68; H, 8.24; N, 19.11.

EXAMPLE 123

N-(4-(4-(2-(tert-Butyl)quinazolin-4-yl)piperazin-1-yl)butyl)imidazo[1,2-a]pyridine-2-carboxamide (123). Prepared from imidazo[1,2-a]pyridine-2-carboxylic acid and 4-(4-(2-(tert-butyl)quinazolin-4-yl)piperazin-1-yl)butan-1-amine in a similar fashion as described in Example 113. Yield: 18%. mp 59-61° C. TLC $R_f$ 0.44 (CHCl$_3$-MeOH, 92.5:7.5); $^1$H NMR (DMSO-d$_6$) δ 1.50 (s, 9H), 1.52-1.68 (m, 2H), 1.77-1.88 (m, 2H), 3.17 (bs, 2H), 3.24-3.41 (m, 4H), 3.64 (d, J=11.1 Hz, 2H), 4.11 (bs, 2H), 4.85 (bs, 2H), 7.32 (t, 1H), 7.64-7.82 (m, 3H), 8.04 (t, 1H), 8.20 (d, J=8.4 Hz, 1H), 8.45 (d, J=8.2 Hz, 1H), 8.75 (s, 1H), 8.86 (d, J=6.8 Hz, 1H), 9.10 (s, 1H); ESI MS m/z 486 (MH)$^+$. Anal. (C$_{28}$H$_{35}$N$_7$O.0.25H$_2$O) Calcd: C, 68.72; H, 7.30; N, 20.00. Found: C, 68.72; H, 7.24; N, 19.80.

EXAMPLE 124

N-(4-(4-(7-(Trifluoromethyl)quinolin-4-yl)piperazin-1-yl)butyl)imidazo[1,2-a]pyridine-2-carboxamide (124). Prepared from imidazo[1,2-a]pyrimidine-2-carboxylic acid and 4-(4-(7-(trifluoromethyl)quinolin-2-yl)piperazin-1-yl)butan-1-amine in a similar fashion as described in Example 113. Yield: 34%. mp 55-58° C. TLC $R_f$ 0.35 (CHCl$_3$-MeOH, 92.5:7.5); $^1$H NMR (DMSO-d$_6$) δ 1.61-1.73 (bs, 2H), 1.87-1.94 (bs, 2H), 3.18-3.30 (bs, 2H), 3.33-3.48 (m, 2H), 3.55-4.38 (m, 8H), 7.29 (s, 1H), 7.44 (d, J=6.4 Hz, 1H), 7.74 (bs, 2H), 7.95 (d, J=8.6 Hz, 1H), 8.41 (d, J=8.8 Hz, 1H), 8.58 (s, 1H), 8.74 (bs, 1H), 8.88 (bs, 1H), 8.96 (d, J=6.1 Hz, 1H), 9.16 (bs, 1H); ESI MS m/z 497 (MH)$^+$. Anal. (C$_{26}$H$_{27}$F$_3$N$_6$O.H$_2$O) Calcd: C, 60.69; H, 5.68; N, 16.33. Found: C, 60.84; H, 5.33; N, 16.29.

EXAMPLE 125

N-(4-(4-(6-(tert-Butyl)-2-methylpyrimidin-4-yl)piperazin-1-yl)butyl)imidazo[1,2-a]pyridine-2-carboxamide (125). Prepared from imidazo[1,2-a]pyrimidine-2-carboxylic acid and 4-(4-(6-(tert-butyl)-2-methylpyrimidin-4-yl)piperazin-1-yl)butan-1-amine in a similar fashion as described in Example 111. Yield: 35%. Colorless oil. TLC $R_f$ 0.32 (CHCl$_3$-MeOH, 95:5); $^1$HNMR (DMSO-d$_6$) δ 1.21 (s, 9H), 1.45-1.64 (m, 4H), 2.22-2.35 (m, 2H ), 2.34 (s, 3H), 2.46 (t, 4H), 3.28-3.34 (m, 2H), 3.58 (t, 4H), 6.47 (s, 1H), 6.96 (td, 1H), 7.33 (td, 1H), 7.58 (dd, J=8.6, 8.2 Hz, 1H), 8.37 (t, 2H), 8.56 (dt, 1H); ESI MS m/z 450 (MH)$^+$. Anal. (C$_{25}$H$_{35}$N$_7$0.75H$_2$O) Calcd: C, 64.84; H, 7.94; N, 21.17. Found: C, 65.02; H, 7.67; N, 20.92.

EXAMPLE 126

N-(4-(4-(Quinolin-2-yl)piperazin-1-yl)butyl)imidazo[1,2-a]pyrimidine-2-carboxamide (126). Prepared from imidazo[1,2-a]pyrimidine-2-carboxylic acid and 4-(4-(quinolin-2-yl)piperazin-1-yl)butan-1-amine in a similar fashion as described in Example 113. Yield: 31%. mp 199-201° C. TLC $R_f$ 0.56 (CHCl$_3$-MeOH, 92.5:7.5); $^1$HNMR (DMSO-d$_6$) δ 1.47-1.63 (m, 4H), 2.35 (t, 2H), 2.44-2.58 (bs, 4H), 3.32-3.58 (m, 2H), 3.67 (t, 4H), 7.17 (q, 1H), 7.15-7.28 (m, 2H), 7.42-7.62 (m, 2H), 7.67 (d, J=8.0 Hz, 1H), 8.06 (d, J=9.2 Hz, 1H), 8.29 (s, 1H), 8.56 (t, 1H), 8.64 (q, 1H), 8.98 (dd, J=6.9, 6.8 Hz, 1H); ESI MS m/z 430 (MH)$^+$. Anal. ($C_{24}H_{27}N_7O.0.25H_2O$) Calcd: C, 66.42; H, 6.39; N, 22.59. Found: C66.34; H, 6.07; N, 22.23.

EXAMPLE 127

N-(4-(4-(Quinazolin-4-yl)piperazin-1-yl)butyl)imidazo[1,2-a]pyridine-2-carboxamide (127). Prepared from imidazo[1,2-a]pyridine-2-carboxylic acid and 4-(4-(quinazolin-4-yl)piperazin-1-yl)butan-1-amine in a similar fashion as described in Example 113. Yield: 7%. mp 130-134° C. TLC $R_f$ 0.10 (CHCl$_3$-MeOH, 95:5); $^1$H NMR (DMSO-d$_6$) δ 1.66-1.78 (m, 4H), 2.45-2.54 (m, 2H), 2.64-2.74 (m, 4H), 3.42-3.55 ( m, 2H), 3.82-3.94 (m, 4H), 6.91-7.00 (m, 1H), 7.32-7.40 (m, 1H), 7.50-7.61 (m, 2H), 7.76-7.86 (m, 2H), 7.97-8.05 (m, 2H), 8.27 (d, J=0.76 Hz, 1H), 8.43-8.50 (m, 1H), 8.56 (s, 1H); ESI MS m/z 429 (MH)$^+$. Anal. ($C_{24}H_{27}N_7O$) Calcd: C, 67.10; H, 6.34; N, 22.83. Found: C, 66.72; H, 6.37; N, 22.53.

EXAMPLE 128

3-Bromo-N-(4-(4-(quinolin-4-yl)piperazin-1-yl)butyl)imidazo[1,2-a]pyridine-2-carboxamide (128). Prepared from 117 and N-bromosuccinimide Yield: 53%. mp 64-66° C. TLC $R_f$ 0.48 (CHCl$_3$-MeOH, 90:10); $^1$H NMR (DMSO-d$_6$) δ 1.49-1.67 (m, 4H), 2.44 (t, 2H), 2.66 (bs, 4H), 3.18 (bs, 4H), 3.25-3.38 (m, 2H), 6.95 (d, J=4.9 Hz, 1H), 7.16-7.22 (m, 1H), 7.44-7.48 (m, 2H), 7.50-7.62 (m, 2H), 7.64-7.73 (m, 2H), 8.42-8.24 (m, 1H), 8.5 (t, 1H), 8.67 (d, J=4.9 Hz, 1H); ESI MS m/z 463 (MH)$^+$. Anal. ($C_{25}H_{27}BrN_6O.0.6H_2O$) Calcd: C, 57.94; H, 5.48; N, 16.21. Found: C, 57.56; H, 5.06; N, 16.05.

EXAMPLE 129

3-Chloro-N-(4-(4-(quinolin-4-yl)piperazin-1-yl)butyl)imidazo[1,2-a]pyridine-2-carboxamide (129). A solution of 117 (0.100 g, 0.23 mmol) and N-chlorosuccinimide (0.032 g, 0.23 mmol) in acetonitrile (4 ml) was stirred at room temperature overnight. The solvent was removed under reduced pressure and the resulting residue was purified over chromatograph over a column of silica using EtOAc:MeOH (80:20) to obtain 0.066 g (56%) of the desired product. mp 55-56° C. TLC $R_f$ 0.48 (CHCl$_3$-MeOH, 90:10); $^1$H NMR (DMSO-d$_6$) δ 1.48-1.68 (m, 4H), 2.49 (t, 2H), 2.66 (bs, 4H), 3.18 (bs, 4H), 3.26-3.40 (m, 2H), 6.95 (d, J=5.1 Hz, 1H), 7.19-7.22 (m, 1H), 7.46-7.58 (m, 2H), 7.65-7.72 (m, 2H), 7.93 (dd, J=8.4, 8.4 Hz, 1H), 7.96-8.04 (m, 1H), 8.42-8.24 (m, 1H), 8.5 (t, 1H), 8.67 (d, J=4.9 Hz, 1H); ESI MS m/z 463 (MH)$^+$. Anal. ($C_{25}H_{27}ClN_6O.0.5H_2O$) Calcd: C, 63.62; H, 5.98; N, 17.81. Found: C, 63.45; H, 5.91; N, 17.60.

EXAMPLE 130

N-(4-(4-(2-(Trifluoromethyl)quinolin-4-yl)piperazin-1-yl)butyl)imidazo[1,2-a]pyridine-2-carboxamide (130). Prepared from imidazo[1,2-a]pyridine-2-carboxylic acid and 4-(4-(2-(trifluoromethyl)quinolin-4-yl)piperazin-1-yl)butan-1-amine in a similar fashion as described for 113. Yield: 16%. mp 122-124° C. TLC $R_f$ 0.56 (CHCl$_3$-MeOH, 90:10); $^1$HNMR (DMSO-d$_6$) δ 1.51-1.68 (m, 4H), 2.44 (t, 2H), 2.67 (bs, 4H), 3.26-3.44 (m, 6H), 6.97 (ddd, J=1.2, 1.2, 1.0 Hz, 1H), 7.24 (s, 1H), 7.31-7.65 (m, 1H), 7.56 (dd, J=9.2, 9.2 Hz, 1H), 7.68-7.74 (m, 1H), 7.78-7.88 (m, 1H), 8.03-8.12 (m, 2H), 8.35 (s, 1H), 8.40 (t, 1H), 8.56-8.60 (m, 1H); ESI MS m/z 497 (MH)$^+$. Anal. ($C_{26}H_{27}F_3N_6O.H_2O$) Calcd: C, 60.69; H, 5.68; N, 16.33. Found: C, 60.84; H, 5.51; N, 16.38.

Synthesis of Piperazinylbutylamine Intermediates 4-(4-(6-(tert-Butyl)-2-methylpyrimidin-4-yl)piperazin-1-yl)butan-1-amine. Step 1. A solution of 4-(tert-butyl)-6-chloro-2-methylpyrimidine (7.98 g, 42.9 mmol) in absolute ethanol (100 mL) was added dropwise to a boiling solution of piperazine (18.46 g, 215 mmol) in ethanol (175 mL) over a period of 2 hours. The reaction mixture was refluxed for 12 hours, cooled to room temperature and the solvent was removed under reduced pressure. The residue was treated with ice-cold water (1 L) and stirred for 15 minutes. After allowing the mixture to stand for an hour, the solid crystalline product obtained was collected by filtration and dried under reduced pressure over $P_2O_5$ to obtain 9.09 g (90%) of 4-(tert-butyl)-2-methyl-6-(piperazin-1-yl)pyrimidine (K877-37). ESI MS m/z 289 (MH)$^+$.

Step 2. A mixture of the above piperazine (7.5 g, 32.05 mmol), N-(4-bromobutyl)-phthalimide (9.10 g, 32.05 mmol) and potassium carbonate (5.30 g, 38.46 mmol) in acetonitrile (200 mL) was stirred at room temperature overnight. The reaction mixture was filtered and the filtrate was concentrated under reduced pressure. The residue thus obtained was purified by flash chromatography over a column of silica using CHCl$_3$-MeOH 98:2 as the eluent to obtain 11.5 g (82%) of 2-(4-(4-(6-(tert-butyl)-2-methylpyrimidin-4-yl)piperazin-1-yl)butyl)isoindoline-1,3-dione (K877-38). ESI MS m/z 436 (MH)$^+$.

Step 3. A mixture of the above (11.5 g, 32.05 mmol), hydrazine hydrate (5.51 g, 64.10 mmol) in methanol (150 mL) was heated under reflux for 2 hours. The reaction mixture was cooled to room temperature and the volatiles were removed under reduced pressure. The residue was dissolved in ether (150 mL), filtered and the filtrate was concentrated under reduced pressure. The residue obtained was purified by chromatography over a column of silica using CHCl$_3$-MeOH—NH$_4$OH (85:13:2) as the eluent to yield 7.6 g (94%) of the desired product. $^1$H NMR (DMSO-d$_6$) δ 1.22 (s, 9H), 1.37-1.38 (m, 2H), 1.41-1.50 (m, 2H), 2.28 (t, J=7.0 Hz, 2H), 2.39 (t, J=5.1 Hz, 2H), 2.54 (t, J=6.8 Hz, 2H), 3.57 (s, 4H), 6.47 (s, 1H); ESI MS m/z 306 (MH)$^+$.

4-(4-(2-(tert-Butyl)-6-methylpyrimidin-4-yl)piperazin-1-yl)butan-1-amine. This compound was prepared from 2-(tert-butyl)-4-chloro-6-methylpyrimidine using procedures analogous to those described above. Overall yield: 48%. $^1$HNMR (DMSO-d$_6$) δ 1.25 (s, 9H), 1.26-1.38 (m, 2H), 1.40-1.50 (m, 2H), 2.23 (s, 3H), 2.28 (t, J=3.7 Hz, 2H), 2.39 (t, J=5.1 Hz, 2H), 2.51 (t, J=6.9 Hz, 2H), 3.57 (t, J=4.9 Hz, 4H), 6.46 (s, 1H); ESI MS m/z 306 (MH)$^+$.

4-(4-(2-(tert-Butyl)-6-cyclopropylpyrimidin-4-yl)piperazin-1-yl)butan-1-amine. This compound was prepared from 2-(tert-butyl)-4-chloro-6-cyclopropylpyrimidine. Overall yield: 28%. $^1$HNMR (DMSO-d$_6$) δ 0.83-0.88 (m, 2H), 0.92-0.97 (m, 2H), 1.22 (s, 9H), 1.34-1.38 (m, 2H), 1.44-1.49 (m, 2H), 2.28 (t, J=7.2 Hz, 2H), 2.39 (t, J=4.9 Hz, 2H), 2.56 (t, J=6.8 Hz, 2H), 3.57 (t, J=4.9 Hz, 4H), 6.49 (s, 1H); ESI MS m/z 332 (MH)$^+$.

4-(4-(2-(tert-Butyl)-6-(trifluoromethyl)pyrimidin-4-yl)piperazin-1-yl)butan-1-amine. This compound was prepared from 2-(tert-butyl)-4-chloro-6-(trifluoromethyl)pyrimidine. Overall yield: 33%. $^1$HNMR (DMSO-d$_6$) δ 1.36 (s, 9H), 1.48-1.61 (m, 4H), 2.38 (t, J=7.25 Hz, 2H), 2.51 (t, J=5.15 Hz, 2H), 2.72 (t, J=6.71 Hz, 2H), 3.72 (s, 4H), 6.59 (s, 1H); ESI MS m/z 360 (MH)$^+$.

4-(4-(2,6-Di-tert-butylpyrimidin-4-yl)piperazin-1-yl)butan-1-amine. This compound was prepared from 2,4-di-tert-butyl-6-chloropyrimidine. Overall yield: 46%. $^1$H NMR (DMSO-d$_6$) δ 1.24 (s, 9H), 1.27 (s, 9H), 1.34-1.49 (m, 4H), 2.29 (t, J=7.5 Hz, 2H), 2.40 (t, J=5.0 Hz, 2H), 2.53 (t, J=6.71 Hz, 2H), 3.59 (t, J=4.8 Hz, 4H), 6.47 (s, 1H); ESI MS m/z 348 (MH)$^+$.

4-(4-(2-(tert-Butyl)quinazolin-4-yl)piperazin-1-yl)butan-1-amine. This compound was prepared from 2-(tert-butyl)-4-chloroquinazoline. Overall yield: 66%. ESI MS m/z 342 (MH)$^+$.

4-(4-(7-Chloroquinolin-4-yl)piperazin-1-yl)butan-1-amine. This compound was prepared from 2-(tert-butyl)-4-chloroquinazoline. Overall yield: 66%. ESI MS m/z 319 (MH)$^+$.

Biological Activity

Binding Affinity. The affinities of the target compounds were determined using radioligand binding experiments.

All radioligand binding experiments were performed according to previously described methods (Luedtke R. R. et al. *Synapse* 2000, 38, 438-449; Chu, W. et al. *Bioorg. Med. Chem.* 2005, 13, 77-87; Taylor, M. et al. *Synapse* 2010, 64, 251-266). Stably transfected HEK cells expressing the human D2-long and the D3 dopamine receptor were developed using the pIRESneo2 bicistronic expression vector (Clontech, Palo Alto, Calif.). Levels of expression of human D2 and D3 dopamine receptors in HEK cells were 57,941±14,686 fmol/mg protein and 4202±1516 fmol/mg protein, respectively. Competition curves were performed using $^{125}$I-IABN. Membrane homogenates (50 μL) were suspended in 50 mM Tris-HCl/150 mM NaCl/10 mM EDTA buffer, pH 7.5 and incubated with 50 μL of $^{125}$I-IABN at 37° C. for 60 min. Nonspecific binding was defined using 4 μM (+)-butaclamol. The radioligand concentration used was approximately equal to the K$_d$ value, and the concentration of the competitive inhibitor ranged over five orders of magnitude. Binding was terminated by the addition of cold wash buffer (10 mM Tris-HCl/150 mM NaCl, pH 7.4) and filtration over a glass-fiber filter (Schleicher and Schuell No. 32). Filters were washed with 10 mL of cold buffer, and the radioactivity was quantitated. A Packard Cobra gamma counter was used for $^{125}$I-labeled radioligands (efficiency=75%). The protein concentration was determined using a BCA reagent (Pierce) with bovine serum albumin as the protein standard. Data from competitive inhibition experiments was modeled using nonlinear regression analysis to determine the concentration of inhibitor that inhibits 50% of the specific binding of the radioligand (IC$_{50}$ value). Competition curves were modeled for a single site. Data from competition dose-response curves were analyzed using Tablecurve program (Jandel). IC$_{50}$ values were converted to equilibrium dissociation constants (K$_i$ values) using the Cheng and Prusoff correction. The binding affinity data for Example compounds are listed in Tables 1-3 along with the calculated D3 selectivity ratio (D2 Ki/D3 Ki). The data show that most of the compounds of the present invention bind to D3 receptors with moderate to high affinity and are selective for dopamine D3 receptor over dopamine D2 receptor.

TABLE 1

Binding Affinity Data for Ureas

| Compd | D3 Ki (nM) | D2 Ki (nM) | D2/D3 |
| --- | --- | --- | --- |
| 1 | 2.0 ± 0.2 | 124 ± 26.2 | 62 |
| 2 | 14.2 ± 2.9 | 303 ± 10.4 | 21 |
| 3 | 0.39 ± 0.10 | 21.0 ± 2.4 | 54 |
| 4 | 4.1 ± 1.0 | 294 ± 59.6 | 72 |
| 5 | 2.7 ± 0.1 | 366 ± 18.0 | 136 |
| 6 | 29.2 ± 5.3 | 12888 ± 2510 | 442 |
| 7 | 41.5 ± 9.1 | 3878 ± 1225 | 93 |
| 8 | 2.7 ± 0.7 | 470 ± 34 | 174 |
| 9 | 15.1 ± 2.8 | 515 ± 59.6 | 34 |
| 10 | 15.1 ± 4.2 | 337 ± 67.8 | 22 |
| 11 | 9.8 ± 1.2 | 1171 ± 128 | 119 |
| 12 | 26.9 ± 4.9 | 933 ± 91 | 35 |
| 13 | 43.1 ± 4.8 | 4044 ± 965 | 94 |
| 14 | 21.4 ± 3.4 | 738 ± 88.8 | 34 |
| 15 | 19.3 ± 1.6 | 582 ± 127 | 30 |
| 16 | 21.2 ± 1.4 | 894 ± 200 | 42 |
| 17 | 16 ± 0.8 | 843 ± 95 | 52 |
| 18 | 24.6 ± 4.9 | 759 ± 97.0 | 31 |
| 19 | 25.2 ± 5.5 | 861 ± 137 | 34 |
| 20 | 13.0 ± 0.7 | 762 ± 159 | 58 |
| 21 | 11.6 ± 0.9 | 557 ± 79.5 | 48 |
| 22 | 24.7 ± 5.4 | 928 ± 231 | 38 |
| 23 | 22.8 ± 4.2 | 802 ± 179 | 35 |
| 24 | 29.9 ± 5.6 | 1178 ± 265 | 39 |
| 25 | 16.6 ± 2.2 | 385 ± 58.5 | 23 |
| 26 | 8.7 ± 2.2 | 707 ± 96.2 | 81 |
| 27 | 29.6 ± 3.2 | 1049 ± 95.7 | 35 |
| 28 | 19.4 ± 4.8 | 428 ± 102 | 22 |
| 29 | 8.0 ± 1.6 | 740 ± 98.3 | 92 |
| 30 | 5.9 ± 1.1 | 455 ± 86.0 | 77 |
| 31 | 2.6 ± 0.3 | 97.4 ± 21.7 | 38 |
| 32 | 13.7 ± 3.1 | 1188 ± 67.4 | 87 |
| 33 | 8.6 ± 1.8 | 463 ± 55.1 | 54 |
| 34 | 12.7 ± 2.5 | 524 ± 42.2 | 41 |
| 35 | 12.8 ± 2.3 | 331 ± 51.9 | 26 |
| 36 | 16.7 ± 4.4 | 530 ± 45 | 32 |
| 37 | 29.0 ± 2.4 | 998 ± 252 | 34 |
| 38 | 3.5 ± 0.7 | 605 ± 62 | 173 |
| 39 | 12.2 ± 2.0 | 778 ± 29.5 | 64 |
| 40 | 2.3 ± 0.5 | 994 ± 106 | 432 |
| 41 | 22.9 ± 5.0 | 490 ± 70.0 | 21 |
| 42 | 2.3 ± 0.3 | 646 ± 1.5 | 281 |
| 43 | 15.0 ± 3.1 | 1022 ± 75.6 | 68 |
| 44 | 49.3 ± 11.2 | 1108 ± 104 | 22 |
| 45 | 25.1 ± 5.5 | 621 ± 143 | 25 |
| 46 | 31.9 ± 7.2 | 906 ± 169 | 28 |
| 47 | 1.9 ± 0.4 | 101.6 ± 11.0 | 53 |
| 48 | 11.0 ± 2.4 | 1621 ± 402 | 147 |
| 49 | 27.0 ± 3.9 | 1274 ± 291 | 47 |
| 50 | 18.4 ± 2.6 | 603 ± 104 | 33 |
| 51 | 44.1 ± 8.1 | 1290 ± 248 | 29 |
| 52 | 7.3 ± 1.6 | 680 ± 135 | 93 |
| 53 | 35.2 ± 8.2 | 713 ± 78.3 | 20 |
| 54 | 40.3 ± 7.2 | 1046 ± 149 | 26 |
| 55 | 3.0 ± 0.2 | 536 ± 118 | 182 |
| 56 | 9.5 ± 1.7 | 308 ± 29.9 | 33 |

TABLE 2

Binding Affinity Data for Additional Ureas

| Compd | D3 Ki (nM) | D2 Ki (nM) | D2/D3 |
| --- | --- | --- | --- |
| 57 | 35.5 ± 7.2 | 644 ± 6.6 | 18 |
| 58 | 70.6 ± 14.8 | 789 ± 192 | 11 |
| 59 | 19.4 ± 4.1 | 342 ± 22.0 | 18 |
| 60 | 46.6 ± 9.1 | 570 ± 119 | 12 |
| 61 | 48.0 ± 10.8 | 896 ± 193 | 19 |
| 62 | 106 ± 5.5 | 1519 ± 344 | 14 |
| 63 | 19.2 ± 3.6 | 359 ± 45.8 | 19 |
| 64 | 9.8 ± 2.0 | 167 ± 25.5 | 17 |
| 65 | 8.6 ± 1.1 | 128 ± 25.8 | 15 |
| 66 | 9.6 ± 2.2 | 125 ± 25.3 | 13 |
| 67 | 73.8 ± 17.5 | 626 ± 143 | 8 |
| 68 | 13.8 ± 2.4 | 184 ± 46.6 | 13 |

TABLE 2-continued

Binding Affinity Data for Additional Ureas

| Compd | D3 Ki (nM) | D2 Ki (nM) | D2/D3 |
|---|---|---|---|
| 69 | 29.8 ± 3.8 | 215 ± 54.1 | 7 |
| 70 | 33.5 ± 8.0 | 215 ± 36.3 | 6 |
| 71 | 27.4 ± 3.8 | 281 ± 46.5 | 10 |
| 72 | 84.2 ± 20.3 | 820 ± 178 | 10 |
| 73 | 130 ± 13 | 990 ± 192 | 8 |
| 74 | 66.8 ± 16.3 | 585 ± 72.7 | 9 |
| 75 | 9.9 ± 1.7 | 59.3 ± 7.5 | 6 |
| 76 | 18.0 ± 3.0 | 125 ± 26.6 | 7 |
| 77 | 138 ± 28.8 | 981 ± 73.9 | 7 |
| 78 | 29.0 ± 4.8 | 448 ± 75.9 | 15 |
| 79 | 51.8 ± 11.4 | 834 ± 133 | 16 |
| 80 | 118 ± 20.1 | 863 ± 135 | 7 |
| 81 | 44.2 ± 8.2 | 507 ± 16.6 | 11 |
| 82 | 129 ± 21.9 | 668 ± 135 | 5 |
| 83 | 112 ± 19.1 | 1550 ± 349 | 14 |
| 84 | 95.7 ± 14.6 | 2608 ± 79.1 | 27 |
| 85 | 87.9 ± 22.8 | 2788 ± 942 | 32 |
| 86 | 110 ± 11.6 | 1849 ± 197 | 17 |
| 87 | 28.3 ± 5.3 | 382 ± 91 | 14 |
| 88 | 668 ± 122 | 10541 ± 2235 | 16 |
| 89 | 110 ± 21.6 | 1181 ± 180 | 11 |
| 90 | 128 ± 30.3 | 1341 ± 166 | 10 |
| 91 | 200 ± 47.6 | 1208 ± 211 | 6 |
| 92 | 166 ± 4.1 | 1352 ± 241 | 8 |
| 93 | 84.8 ± 21.3 | 560 ± 53 | 7 |
| 94 | 219 ± 23.8 | 5485 ± 1153 | 25 |
| 95 | 215 ± 45.5 | 5558 ± 1345 | 26 |
| 96 | 74.9 ± 15 | >5000 | >66 |
| 97 | 245 ± 46.4 | 2440 ± 175 | 10 |
| 98 | 1018 ± 201 | 6405 ± 1098 | 6 |
| 99 | 299 ± 37.8 | 7249 ± 754 | 24 |
| 100 | 5318 ± 2215 | >100,000 | >18 |
| 101 | 57.1 ± 3.5 | 789 ± 45.7 | 14 |
| 102 | 19.2 | 962 | 50 |

TABLE 3

Binding Affinity Data for Amides

| Compd | D3 Ki (nM) | D2 Ki (nM) | D2/D3 |
|---|---|---|---|
| 103 | 9.4 ± 2.3 | 1510 ± 384 | 160 |
| 104 | 35.3 ± 4.8 | 5162 ± 822 | 146 |
| 105 | 34.5 ± 7.6 | 1015 ± 68.2 | 29 |
| 106 | 62.0 ± 12.7 | 3092 ± 768 | 50 |
| 107 | 30.6 ± 7.4 | 970 ± 137 | 32 |
| 108 | 31.7 ± 7.4 | 809 ± 194 | 26 |
| 109 | 35.6 ± 1.4 | 337 ± 24.3 | 9 |
| 110 | 167 ± 8.5 | 1797 ± 257 | 11 |
| 111 | 9.3 ± 2.1 | 366 ± 33.7 | 39 |
| 112 | 8.4 ± 0.7 | 191 ± 32.9 | 23 |
| 113 | 4.2 ± 0.6 | 511.3 ± 65.6 | 122 |
| 114 | 11.8 ± 1.1 | 435.5 ± 43.4 | 37 |
| 115 | 8 ± 1.6 | 450 ± 52.1 | 56 |
| 116 | 10.2 ± 1.8 | 654.8 ± 80.6 | 64 |
| 117 | 20.5 ± 3.5 | 572 ± 71.8 | 28 |
| 118 | 28.7 ± 4.9 | 1883 ± 488 | 66 |
| 119 | 45.4 ± 11.3 | 934 ± 222 | 21 |
| 120 | 28.8 ± 6.1 | 301 ± 63.1 | 10 |
| 121 | 27.3 ± 3.4 | 298 ± 74.1 | 11 |
| 122 | 18.8 ± 3.5 | 361 ± 71.1 | 19 |
| 123 | 78.2 ± 19.2 | 1452 ± 275 | 19 |
| 124 | 98.7 ± 24.3 | 4983 ± 843 | 50 |
| 125 | 134 ± 29.3 | 4604 ± 785 | 34 |
| 126 | 161 ± 26.2 | 1260 ± 142 | 8 |
| 127 | 253 ± 23.3 | 1133 ± 63.8 | 4 |
| 128 | 285 ± 77 | 2331 ± 785 | 8 |
| 129 | 323 ± 75 | 3561 ± 1947 | 11 |
| 130 | 524 ± 142 | 13567 ± 6256 | 26 |

Functional Activity. Mitogenesis Assays. Agonist stimulation of D2 or D3 dopamine receptors leads to an increase in mitogenic activity (Pilon, C. et al. *Eur. J. Pharmacol.* 1994, 268, 129-139). These assays are based on $^3$H-thymidine uptake by cells that are proliferating.

D2 mitogenesis functional assay: CHO cells expressing human D2 receptors (CHOp-D2 cells) were maintained in alpha-MEM with 10% FCS, 0.05% pen-strep, and 200 µg/mL of G418. To measure D2 stimulation of mitogenesis (agonist assay) or inhibition of quinpirole stimulation of mitogenesis (antagonist assay), CHOp-D2 cells were seeded in a 96-well plate at a concentration of 5,000 cells/well. The cells were incubated at 37° C. in alpha-MEM with 10% FCS. After 48-72 hours, the cells were rinsed twice with serum-free alpha-MEM and incubated for 24 hours at 37° C. Serial dilutions of test compounds were made by the Biomek robotics system in serum-free alpha-MEM. In the functional assay for agonism, the medium was removed and replaced with 100 µL of test compound in serum-free alpha-MEM. In the antagonist assay, the serial dilution of the putative antagonist test compound was added in 90 µL (1.1× of final concentration) and 300 nM quinpirole (30 nM final) was added in 10 µL. After another 24-hour incubation at 37° C., 0.25 µCi of [$^3$H]thymidine in alpha-MEM supplemented with 10% FCS was added to each well and the plates were further incubated for 2 hours at 37° C. The cells were trypsinized by addition of 10× trypsin solution (1% trypsin in calcium-magnesium-free phosphate-buffered saline) and the plates were filtered and counted as usual. Quinpirole was run as an internal control and dopamine was included for comparative purposes. Butaclamol was run as standard antagonist.

D3 mitogenesis functional assay: CHO cells expressing human D3 receptors (CHOp-D3 cells) were maintained in alpha-MEM with 10% fetal bovine serum (FBS, Atlas Biologicals), 0.05% pen-strep, and 200 µg/ml of G418. To measure D3 stimulation of mitogenesis (agonist assay) or inhibition of quinpirole stimulation of mitogenesis (antagonist assay), CHOp-D3 cells were seeded in a 96-well plate at a concentration of 5,000 cells/well. The cells are incubated at 37° C. in alpha-MEM with 10% FBS. After 48-72 hours, the cells are rinsed twice with serum-free alpha-MEM and incubated for 24 hours at 37° C. Serial dilutions of test compounds were made by the Biomek robotics system in serum-free alpha-MEM. In the functional assay for agonism, the medium is removed and replaced with 100 µL of test compound in serum-free alpha-MEM. In the antagonist assay, the serial dilution of the putative antagonist test compound was added in 90 µL (1.1× of final concentration) and 300 nM quinpirole (30 nM final) was added in 10 uL. After another 16-hour incubation at 37° C., 0.25 µCi of [$^3$H]thymidine in alpha-MEM supplemented with 10% FBS was added to each well and the plates were further incubated for 2 hours at 37° C. The cells were trypsinized by addition of 10× trypsin solution (1% trypsin in calcium-magnesium-free phosphate-buffered saline) and the plates were filtered and counted as usual. Quinpirole was run as an internal control and dopamine was included for comparative purposes. Butaclamol was run as the standard antagonist. Data were analyzed using GraphPAD Prism and agonist potency was expressed as $EC_{50}$ values or % stimulation and antagonist potency was expressed as $IC_{50}$ values. In these assays, based on the % maximum stimulation as compared to the standard agonist quinpirole (100%) the compounds were classified into following categories: ≥90% full agonist; 70-90% partial to full agonist; <70% partial agonist; 0-20% potential antagonist. The intrinsic activities of some of the Example compounds are listed in Table 4 and Table 5.

TABLE 4

Functional Activity of Ureas in the Mitogenesis Assay

| Compd | D2 Agonist $EC_{50}$ (nM) | D2 Agonist Emax | D2 Antagonist $IC_{50}$ (nM) | D2 Antagonist $I_{max}$ | D3 Agonist $EC_{50}$ (nM) | D3 Agonist Emax | D3 Antagonist $IC_{50}$ (nM) | D3 Antagonist $I_{max}$ |
|---|---|---|---|---|---|---|---|---|
| 3 | ND | <20% at 10 µM | 14.6 ± 5.5 | 91.0% at 10 µM | ND | <20% at 10 µM | 3.43 ± 0.29 | 93.1% |
| 8 | >10 µM | <1% at 10 µM | 440 ± 160 | 100% at 10 µM | >10 µM | 3% at 10 µM | 125 ± 37 | 88.2% |
| 29 | >10 µM | <1% at 10 µM | 232 ± 61 | 99.9% at 10 µM | >10 µM | <5% at 10 µM | 54.7 ± 9.4 | 83.8% |
| 32 | >10 µM | <1% at 10 µM | 257 ± 90 | 100% at 10 µM | >10 µM | <8% at 10 µM | 195 ± 39 | 84.4% |
| 47 | ND | <20% at 10 µM | 286 ± 27 | 98.5% at 10 µM | ND | <20% at 10 µM | 40 ± 15 | 96.8% |
| 48 | ND | ND | ND | ND | >10 µM | <5% at 10 µM | 2000 ± 480 | 81.2% |

TABLE 5

Functional Activity of Amides in the Mitogenesis Assay

| Compd | D2 Agonist $EC_{50}$ (nM) | D2 Agonist Emax | D2 Antagonist $IC_{50}$ (nM) | D2 Antagonist $I_{max}$ | D3 Agonist $EC_{50}$ (nM) | D3 Agonist Emax | D3 Antagonist $IC_{50}$ (nM) | D3 Antagonist $I_{max}$ |
|---|---|---|---|---|---|---|---|---|
| 113 | ND | 0% at 10 µM | 2300 ± 1100 | ND | ND | 0% at 10 µM | 157 ± 34 | ND |
| 114 | ND | <1% at 10 µM | 205 ± 48 | ND | ND | 14% at 10 µM | 51 ± 21 | ND |
| 115 | ND | <20% at 10 µM | 420 ± 120 | 96.6% at 10 µM | ND | <20% at 10 µM | 245 ± 33 | 94.7% |
| 116 | ND | <1% at 10 µM | 1160 ± 110 | ND | ND | <1% at 10 µM | 637 ± 99 | ND |
| 117 | ND | ND | ND | ND | ND | <20% at 10 µM | 120 ± 22 | 97.2% |

Functional Activity. Whole cell adenylyl cyclase assay. The intrinsic activity of the compounds was evaluated by determining their ability to inhibit forskolin-dependent (100 µM) stimulation of adenylyl cyclase activity using a whole cell assay. A whole cell-cyclic AMP accumulation assay was performed with stably transfected HEK cells expressing human D2 or D3 dopamine receptors. This assay is an adaptation of an earlier published method (Su et al., Cyclic Nucleotide Res. 1976, 2, 257-285). Details regarding this method have been published (Chu, W. et al. *Bioorg. Med. Chem.* 2005, 13, 77-87; Taylor, M. et al. *Synapse* 2010, 64, 251-266). Confluent (60-80%) HEK cells transfected with recombinant D2-like dopamine receptors were grown in DMEM/10% fetal calf serum containing geneticin in 75-cm³ flasks. The endogenous ATP pool is radioactively labeled by preincubating the cells in serum-free DMEM/25 mM Hepes medium containing 2 µCi/mL of [2,8-$^3$H]-adenine (20-Ci/mmol) in a 5% $CO_2$ incubator at 37° C. for 75 min. The radioactive medium was removed by aspiration. Serum-free DMEM (5.6 mL) containing 25 mM HEPES, pH 7.4, and 0.1 mM of the phosphodiesterase inhibitor isobutylmethylxanthine was added to the flask. A 400-µL aliquot of cells was removed and added to 50 µL of forskolin (100 µM) and 50 µL of test drug or quinpirole in DMEM-HEPES. The cells were incubated for 20 min at 37° C. (vortexing every 5 min). The reaction was terminated by the addition of 0.5 mL of 10% trichloroacetic acid (w/v) containing 1.0 mM unlabeled cyclic AMP as a recovery standard. Both the [$^3$H]-cyclic AMP and the [$^3$H]-ATP fractions were collected following separation using columns of Dowex AG-50W-X4 and alumina. The final yield of [$^3$H]-cyclic AMP is corrected for column recovery of unlabeled cyclic AMP determined spectrophotometrically ($OD_{259}$). The results are reported as percent conversion of [$^3$H]-ATP into [$^3$H]-cyclic AMP. The values for the percent inhibition are reported as the actual percent of inhibition of the $^3$H-cAMP accumulation relative to the assay performed in the absence of a test compound, minus basal activity. Values are reported as the mean values ±S.E.M. The classic D2-like dopamine receptor antagonist and agonist (haloperidol and quinpirole, respectively) were included in each assay as reference compounds. The percent maximum response is the value for the inhibition normalized to the value for the full agonist quinpirole. The concentrations for all the compounds was >10× the $K_i$ value of the compound at human D2 or D3 dopamine receptors, obtained from competitive radioligand binding experiments. The data for the Example compounds are presented in Table 6 and Table 7.

TABLE 6

Functional Activity of Ureas in the Cyclase Assay

| Compd | Conc (nM) | D2 Cyclase % Inhibition Normalized | Conc (nM) | D3 Cyclase % Inhibition Normalized |
|---|---|---|---|---|
| 1 | 4000 | 91.4 ± 2.4 | 20 | 48.3 ± 9.4 |
| 3 | 500 | 61.0 ± 4.5 | 5 | 66.4 ± 16.4 |
| 5 | 4000 | 54.5 ± 4.5 | 30 | 73.4 ± 11.0 |
| 8 | 5000 | −4.8 ± 4.1 | 50 | 60.7 ± 10.7 |
| 11 | 12000 | 24.4 ± 3.8 | 100 | 43.1 ± 9.4 |
| 13 | NA | Insoluble | 400 | 61.9 ± 6.4 |
| 26 | 8000 | 34.0 ± 9.1 | 90 | 20.0 ± 6.2 |
| 29 | 8000 | 21.8 ± 6.6 | 80 | 60.9 ± 4.0 |
| 30 | 5000 | 6.1 ± 7.5 | NA | ND |
| 47 | NA | ND | 20 | 78.9 ± 17.1 |
| 48 | NA | Insoluble | 200 | 64.3 ± 10.4 |

TABLE 7

Functional Activity of Amides in the Cyclase Assay

| Compd | Conc (nM) | D2 Cyclase % Inhibition Normalized | Conc (nM) | D3 Cyclase % Inhibition Normalized |
|---|---|---|---|---|
| 113 | 5000 | −1.9 ± 13.3 | 50 | 27.7 ± 7.0 |
| 115 | NA | Insoluble | 100 | 37.8 ± 5.4 |
| 116 | NA | Insoluble | 200 | 31.5 ± 7.0 |
| 104 | NA | ND | 400 | 53.4 ± 13.0 |

In Vivo Studies. Effect on Cocaine-Self administration. These studies were performed using Long Evans rats using standard protocols (Quinlan M. G. et al. *Psychopharmacol.* 2004, 175, 53-59; Ranaldi, R. et al. *Behav. Pharmacol.* 2011, 22, 347-353). Cocaine self-administration sessions were conducted in sixteen operant chambers; eight measuring 30×22×27 cm (l×w×h) and the other eight measuring 26×26×30 cm (l×w×h). Each chamber was situated inside a sound-attenuating box and was equipped with two retractable levers, a white light above each lever, and a tether. Polyethylene tubing, covered by the tether, connected the animal, through a fluid swivel, to a syringe in a syringe pump (Razel, 3.33 rpm). Cocaine was dissolved in 0.9% saline to achieve doses of 0.375, 0.75 and 1.5 mg/kg/ injection. Test compound 113 was dissolved in distilled water to achieve doses of 0, 3.75, 7.5 and 15 mg/kg and administered in volumes of 1 mL/kg. Animals were trained to self-administer cocaine (0.75 mg/kg/injection) initially under a fixed ratio 1 (FR1) schedule of reinforcement during daily 3-hour sessions. Each session began with a priming injection and subsequent drug injections were earned by lever presses. Responding on an active lever activated the syringe pump for 4.5 s causing the intravenous delivery of cocaine and the onset of a white light above the active lever for 20 s. Responses on an inactive lever were counted but had no consequences. The active and inactive levers (left/ right) were counterbalanced across animals and remained constant for the duration of the experiment. After the animals demonstrated a steady rate of self-administration for 3 consecutive sessions they were placed on a progressive ratio (PR) schedule of reinforcement starting with one of three randomly chosen doses of cocaine (0.375, 0.75 or 1.5 mg/kg/injection). All PR sessions—training and tests—were 7 h long. The PR schedule required an animal to emit progressively more responses in order to obtain successive cocaine infusions (1, 2, 4, 6, 9, 12, 15, 20 . . . ) during a session (for details of the procedure see, Richardson N. R. et al. *J. Neurosci. Methods.* 1996, 66, 1-11). Under this schedule, the requirement for lever pressing becomes so high that eventually the animals stop responding and reach a BP. The BP was operationally defined as the total number of infusions earned prior to a one-hour period during which no infusions were obtained. Animals were tested with a dose of the D3 antagonist when they demonstrated stable BPs. Stable BPs were operationally defined as three consecutive BPs that did not differ by more than 2 ratio steps and did not show descending or ascending trends. On the test day the animals were injected with 113 intraperitoneally 10 minutes prior to the self-administration session. Each animal was tested with one dose of the D3 antagonist, randomly determined, at as many of the three cocaine doses as possible. After a particular test the animal's cocaine dose was changed to another one (randomly determined) and its baseline BP on the new dose was established. BP during the test session was expressed as the percentage of the average BP obtained during the last three baseline sessions. Percentage of baseline BP and final ratio (i.e. the number of lever presses required for the BP infusion) were analyzed using separate two-way analyses of variance (ANOVAs) with dose of 113 and dose of cocaine as between-groups factors. Because not all animals were tested at each level of the cocaine dose factor, this factor was treated as a between-groups rather than as a repeated measures factor, resulting in a more conservative test. Significant effects were followed by pairwise comparisons with Tukey adjustments. Responding for cocaine under the PR schedule of reinforcement was related to the doses of cocaine regardless of the antagonist treatment; generally, the higher the cocaine dose, the higher the final ratios completed by the rats (see FIG. 1). To best understand how the antagonist affected cocaine reward we investigated its effects on BP during the test as a percentage of BP during baseline for each rat (FIG. 2). Compound 113 caused a dose-related reduction in the percentage of baseline BPs such that the two higher doses (7.5 and 15 mg/kg) reduced BPs to a greater degree than the 3.75 mg/kg dose (see FIG. 2). The patterns of BP reductions with the 7.5 and 15 mg/kg doses did not appear different from each other. These observations were supported by our statistical analyses. Specifically, a two-way ANOVA on BPs with 113 dose and cocaine dose as factors revealed significant main effects of the D3 receptor antagonist ($F(3, 97)=12.1$, $p<0.05$) and cocaine ($F(2, 97)=5.52$, $p<0.05$) but no interaction between these factors. Tukey post hoc comparisons among 113 doses revealed that the animals receiving 3.75, 7.5 or 15 mg of 113 showed significant reductions in the percentage of baseline BPs ($ps<0.05$) compared to vehicle. The 3.75 mg dose of 113 differed significantly from the vehicle and 15 mg doses ($p<0.05$) but not from the 7.5 mg dose. Thus, 113 caused a dose-related reduction in BPs for cocaine under a PR schedule of reinforcement.

In Vivo Studies. Effect on Food-Self administration. These studies were performed using Long Evans rats using standard protocols. Training and testing took place in ventilated and sound-attenuated operant chambers measuring 30×21×18 cm. Each chamber contained two levers, one light above each of the levers, and a food trough. Each lever was positioned 2.5 cm from the rod floor and the food trough (measuring 5×5 cm) was centered between the two levers. A different set of animals (n=8) was trained to press a lever reinforced by food under a FR1 schedule of reinforcement. Each lever press resulted in the delivery of 2 food pellets and presentation of the light stimulus for 3 s. When animals demonstrated learning of the lever press response, operationally defined as responding for five consecutive 10-min sessions where the total number of rewards per session was greater than 100, the animals were placed on a PR schedule. Animals were allowed to continue daily sessions of food self-administration under the PR schedule until they showed stable BPs (the requirements for stable BPs were the same as in the cocaine self-administration procedure described above). After BPs stabilized, the animals were tested either with the 0 or 3.75 mg dose of compound 113 under the PR schedule. Afterward, animals remained on the PR schedule for at least 3 sessions and until stable BPs were demonstrated before being tested with the other dose of 113. Percentage of baseline BPs for food self-administration was analyzed using a dependent measures t-test comparing the 0 and 3.75 mg doses of 113. The 3.75 mg dose of 113, the lowest dose of this compound that caused a significant reduction in cocaine BPs (FIG. 2), did not affect food self-administration under a PR schedule of reinforcement (see FIG. 3). A repeated-measures t-test failed to show a significant difference in the percentage of baseline BP between doses [$t(7)=0.43$, $p=0.66$]. The results show that the lowest dose of 113 that caused a significant reduction in BPs for cocaine reward did not affect BPs for food reward.

In Vivo Studies. Effect on Locomotor Activity. These studies were performed using Long Evans rats using standard protocols. Locomotor activity chambers measuring 43×43×30 cm (l×w×h) were used for the locomotor activity experiments. Each chamber was equipped with eight photoemitters positioned along the length of the chamber 6 cm above the floor, each paired directly opposite a photocell. Locomotor activity counts were registered when adjacent beams were broken consecutively. Before receiving any drug, the animals (n=96) were placed in locomotor activity chambers for habituation, for 2 hours per day for 3 consecutive days. Based on the locomotor activity score obtained during the third habituation session, animals were assigned into one of 9 treatment groups. Four groups were used to determine whether compound 113 alone altered locomotor activity and the remaining 5 groups to determine whether 113 altered cocaine-induced locomotor activity. For the 113 alone experiments, each of the four groups received one of 4 doses of 113 (0, 3.75, 7.5 or 15 mg/kg) 10 minutes prior to placement in the activity chambers. For the 113 cocaine interaction experiments, each of 4 groups were injected with one of the 4 doses of the compound (0, 3.75, 7.5 or 15 mg/kg) 10 minutes before receiving 10 mg/kg of cocaine as the second injection. The fifth group received the 113 vehicle (deionized water) as the first injection and saline as the second. All animals were placed in the locomotor activity chambers immediately after the second injection. The locomotor counts in the 113 alone and 113/cocaine experiments were analyzed using two separate mixed-design ANOVAs with 113 dose (between-groups) and 5-min bins (repeated measures) as factors. Significant interactions were followed by tests of simple effects of 113 dose at each time interval. FIG. 4 shows the effects of 113 administered alone on spontaneous locomotor activity. The 3.75 mg dose, which significantly reduced cocaine BPs and had no effect on food BPs, had no effect on spontaneous locomotor activity. The 7.5 and 15 mg doses appeared to reduce locomotor activity in the first 5 minutes of testing but did not affect activity after that. A two-way mixed-design ANOVA with 113 dose (between groups) and time interval (repeated measures) as factors showed a significant time effect $[F(23, 621)=64.12, p<0.05]$ but no 113 dose effect nor an interaction between these factors.

FIG. 5 shows the effects of 113 on cocaine-induced locomotor activity. Groups treated with any of the 113 doses and cocaine showed less locomotor activity than the vehicle/cocaine group, but not less than the vehicle/vehicle group, during the first 20 minutes of the session. This reduction of cocaine-induced locomotor activity appeared to be dose-related; the higher 113 doses produced greater reductions in cocaine-induced locomotion than the lower doses. A two-way, mixed-design ANOVA with 113 dose (between groups) and time interval (repeated measures) as factors showed a significant 113×time interaction $[F(92, 805)=2.9, p<0.05]$, a significant 113 dose effect $[F(4, 35)=5.91, p<0.05]$ and a significant time effect $[F(23, 805)=73.4, p<0.05]$. Tests of simple effects of 113 dose at each time interval showed significant dose effects at the 5, 10, 15, 20, 30 and 35 min intervals. Tukey post hoc tests revealed that the vehicle/cocaine group differed significantly from the vehicle/vehicle group at the 10, 15, 20, 30 and 35 min intervals, from the 113 15 mg dose at the 5, 10, 15 and 20 min intervals, from the 113 7.5 mg dose at the 5 and 15 min intervals and from the 113 3.75 mg dose at the 15 min interval. The results showed that 113 reduced locomotor activity in the first 5 minutes of the session but not afterward and overall none of the doses tested produced significant effects on spontaneous locomotor activity at any time during the test sessions. However, 113 did significantly reduce cocaine-induced locomotor activity in a dose-related fashion.

In Vivo Studies. Effect on Reinstatement. Rats were trained to self-administer cocaine (1.0 mg/kg/injection) under a FR1 schedule of reinforcement in daily 3-h sessions and, after stable responding was established (as described above) the schedule was changed to FR3. After stable responding under the FR3 schedule was established, extinction training began. Stable responding was defined as follows: 12 consecutive sessions in which total rewards per session was greater than 20 and in which total rewards per session for the last three sessions was within ±10% of the mean of the three sessions. During extinction sessions (each 3 h long) responding on the active and inactive levers were counted but produced no programmed consequences. For any rat extinction sessions continued until it emitted fewer than 7 presses per hour on the active and fewer than 7 presses per hour on the inactive levers for three consecutive sessions. After extinction criteria were met each rat was tested in one 1-h reinstatement session; each rat received an ip injection of vehicle or one of 3 doses of the test compound and 20 minutes later was placed in the operant chamber. At the start of the reinstatement session the cocaine-associated cues (light on for 20 s and pump on for 4.5 s) were presented twice, once at 25 sec and again at 2 min into the session. Presses on the active lever illuminated the light and activated the pump. Presses on the inactive lever produced no consequences. For each group the data consisted of the total number of responses on the active lever and total number of responses on the inactive lever during the reinstatement test. Animals demonstrated a resumption of pressing on the active lever during the cue-induced reinstatement test (see Vehicle group in FIG. 6). This reinstatement effect was strongly reduced in a dose-related fashion with increasing doses of 113 (see FIG. 6).

In keeping with the present disclosure, the compounds of the present disclosure can be used alone or in appropriate association, and also may be used in combination with pharmaceutically acceptable carriers and other pharmaceutically active compounds. The active agent may be present in the pharmaceutical composition in any suitable quantity.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The choice of carrier will be determined in part by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granule; (c) powders; (d) suspensions in an appropriate liquid; and (e) suitable emulsions. Liquid formulations may include diluents, such as water, cyclodextrin, dimethyl sulfoxide and alcohols, for example, ethanol, benzyl alcohol, propylene glycol, glycerin, and the polyethylene alcohols including polyethylene glycol, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, and gels containing, in addition to the active ingredient, such carriers as are known in the art.

The compounds alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcelluslose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-does or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, Eds., 238-250 (1982) and *ASHP Handbook on Injectable Drugs*, Toissel, $4^{th}$ ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of exogenously administering a compound of the present disclosure to an animal are available, and, although more than one route can be used to administer a particular compound, a particular route can provide a more immediate and more effective reaction than another route.

As regards these applications, the present method includes the administration to an animal, particularly a mammal, and more particularly a human, of a therapeutically effective amount of the compound effective in the treatment of a condition that is capable of treatment with an agonist and/or antagonist of the dopamine receptors. The dose administered to an animal, particularly a human, in the context of the present invention should be sufficient to affect a therapeutic response in the animal over a reasonable time frame. One skilled in the art will recognize that dosage will depend upon a variety of factors including the condition of the animal, the body weight of the animal, as well as the severity.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one skilled in the art that various conditions or disease states, in particular chronic conditions or disease states, may require prolonged treatment involving multiple administrations.

Exemplary embodiments of the present disclosure include:

Embodiment A. A compound represented by following formula I

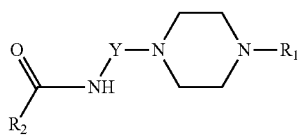

Formula I in which:
Y is an unbranched, saturated or unsaturated hydrocarbon chain with 2-5 hydrocarbon atoms,
$R_1$=aryl,
$R_2$=$NR_3R_4$ wherein $R_3$ and $R_4$ together form a heterocycle,
pharmaceutically acceptable salts thereof, deuterated forms thereof, isomers thereof, solvates thereof, and mixtures thereof.

Embodiment B. A compound represented by following formula (I)

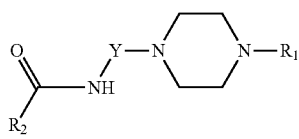

Formula I

In which:
Y is an unbranched, saturated or unsaturated hydrocarbon chain with 2-5 hydrocarbon atoms
$R_1$=heterocycle other than benzothiophene
$R_2$=4-substituted cyclohexyl, 1-substituted piperidine-4-yl or imidazo(1,2-a)azine-2-yl,
pharmaceutically acceptable salts thereof, deuterated forms thereof, isomers thereof, solvates thereof, and mixtures thereof.

Embodiment C. A compound selected from the group consisting of:

4-Phenyl-N-(4-(4-phenylpiperazin-1-yl)butyl)piperazine-1-carboxamide,
4-Phenyl-N-(4-(4-(3-(trifluoromethyl)phenyl)piperazin-1-yl)butyl)piperazine-1-carboxamide,
N-(4-(4-(2,3-Dichlorophenyl)piperazin-1-yl)butyl)-4-phenylpiperazine-1-carboxamide,
N-(4-(4-(3-Cyano-5-(trifluoromethyl)phenyl)piperazin-1-yl)butyl)-4-phenylpiperazine-1-carboxamide,
N-(4-(4-(2-(tert-Butyl)-6-methylpyrimidin-4-yl)piperazin-1-yl)butyl)-4-phenylpiperazine-1-carboxamide,
N-(4-(4-(6-(tert-Butyl)-2-methylpyrimidin-4-yl)piperazin-1-yl)butyl)-4-phenylpiperazine-1-carboxamide,
N-(4-(4-(6-Methyl-2-(trifluoromethyl)pyrimidin-4-yl)piperazin-1-yl)butyl)-4-phenylpiperazine-1-carboxamide,
N-(4-(4-(2-(tert-Butyl)-6-(trifluoromethyl)pyrimidin-4-yl)piperazin-1-yl)butyl)-4-phenylpiperazine-1-carboxamide,
N-(4-(4-(2-(tert-Butyl)-6-cyclopropylpyrimidin-4-yl)piperazin-1-yl)butyl)-4-phenylpiperazine-1-carboxamide,
N-(4-(4-(2,6-Di-tert-butylpyrimidin-4-yl)piperazin-1-yl)butyl)-4-phenylpiperazine-1-carboxamide,
4-Phenyl-N-(4-(4-(quinolin-4-yl)piperazin-1-yl)butyl)piperazine-1-carboxamide,
N-(4-(4-(7-Chloroquinolin-4-yl)piperazin-1-yl)butyl)-4-phenylpiperazine-1-carboxamide,
N-(4-(4-(2-(tert-Butyl)quinazolin-4-yl)piperazin-1-yl)butyl)-4-phenylpiperazine-1-carboxamide,
N-(4-(4-(2-(tert-Butyl)-6-(trifluoromethyl)pyrimidin-4-yl)piperazin-1-yl)butyl)-4-(2-chlorophenyl)piperazine-1-carboxamide,
N-(4-(4-(2-(tert-Butyl)-6-(trifluoromethyl)pyrimidin-4-yl)piperazin-1-yl)butyl)-4-(3-chlorophenyl)piperazine-1-carboxamide,
N-(4-(4-(2-(tert-Butyl)-6-(trifluoromethyl)pyrimidin-4-yl)piperazin-1-yl)butyl)-4-(4-chlorophenyl)piperidine-1-carboxamide,
N-(4-(4-(2-(tert-Butyl)-6-(trifluoromethyl)pyrimidin-4-yl)piperazin-1-yl)butyl)-4-cyano-4-phenylpiperidine-1-carboxamide,
N-(4-(4-(2-(tert-Butyl)-6-(trifluoromethyl)pyrimidin-4-yl)piperazin-1-yl)butyl)-4-(2,3-dichlorophenyl)piperazine-1-carboxamide,
N-(4-(4-(2-(tert-Butyl)-6-(trifluoromethyl)pyrimidin-4-yl)piperazin-1-yl)butyl)-4-(2-methoxyphenyl)piperazine-1-carboxamide),
N-(4-(4-(2-(tert-Butyl)-6-(trifluoromethyl)pyrimidin-4-yl)piperazin-1-yl)butyl)-4-(3-methoxyphenyl)piperazine-1-carboxamide,
N-(4-(4-(2-(tert-Butyl)-6-(trifluoromethyl)pyrimidin-4-yl)piperazin-1-yl)butyl)-4-(4-methoxyphenyl)piperazine-1-carboxamide,
N-(4-(4-(2-(tert-Butyl)-6-(trifluoromethyl)pyrimidin-4-yl)piperazin-1-yl)butyl)-4-(m-tolyl)piperazine-1-carboxamide,
N-(4-(4-(2-(tert-Butyl)-6-(trifluoromethyl)pyrimidin-4-yl)piperazin-1-yl)butyl)-4-(p-tolyl)piperazine-1-carboxamide,
N-(4-(4-(2-(tert-Butyl)-6-(trifluoromethyl)pyrimidin-4-yl)piperazin-1-yl)butyl)-4-(2,3-dimethylphenyl)piperazine-1-carboxamide,
N-(4-(4-(2-(tert-Butyl)-6-(trifluoromethyl)pyrimidin-4-yl)piperazin-1-yl)butyl)-4-(2-cyanophenyl)piperazine-1-carboxamide,
N-(4-(4-(2-(tert-Butyl)-6-(trifluoromethyl)pyrimidin-4-yl)piperazin-1-yl)butyl)-4-(3-cyanophenyl)piperazine-1-carboxamide, N-(4-(4-(2-(tert-Butyl)-6-(trifluoromethyl)pyrimidin-4-yl)piperazin-1-yl)butyl)-4-(3-(trifluoromethyl)phenyl)piperazine-1-carboxamide, N-(4-(4-(2-(tert-Butyl)-6-(trifluoromethyl)pyrimidin-4-yl)piperazin-1-yl)butyl)-4-(4-(trifluoromethyl)phenyl)piperazine-1-carboxamide, N-(4-(4-(2-(tert-Butyl)-6-(trifluoromethyl)pyrimidin-4-yl)piperazin-1-yl)butyl)-4-(pyridin-2-yl)piperazine-1-carboxamide, N-(4-(4-(2-(tert-Butyl)-6-(trifluoromethyl)pyrimidin-4-yl)piperazin-1-yl)butyl)-4-(pyridin-3-yl)piperazine-1-carboxamide, N-(4-(4-(2-(tert-Butyl)-6-(trifluoromethyl)pyrimidin-4-yl)piperazin-1-yl)butyl)-4-(pyridin-4-yl)piperazine-1-carboxamide, N-(4-(4-(2-(tert-Butyl)-6-(trifluoromethyl)pyrimidin-4-yl)piperazin-1-yl)butyl)-4-(pyrimidin-2-yl)piperazine-1-carboxamide, N-(4-(4-(2-(tert-Butyl)-6-(trifluoromethyl)pyrimidin-4-yl)piperazin-1-yl)butyl)-4-(pyrazin-2-yl)piperazine-1-carboxamide, N-(4-(4-(2-(tert-Butyl)-6-(trifluoromethyl)pyrimidin-4-yl)piperazin-1-yl)butyl)-4-(quinolin-4-yl)piperazine-1-carboxamide, N-(4-(4-(2-(tert-Butyl)-6-(trifluoromethyl)pyrimidin-4-yl)piperazin-1-yl)butyl)-4-cyclopropylpiperazine-1-carboxamide, 4-Benzyl-N-(4-(4-(2-(tert-butyl)-6-(trifluoromethyl)pyrimidin-4-yl)piperazin-1-yl)butyl)piperazine-1-carboxamide, 4-Benzoyl-N-(4-(4-(2-(tert-butyl)-6-(trifluoromethyl)pyrimidin-4-yl)piperazin-1-yl)butyl)piperazine-1-carboxamide, N-(4-(4-(2-(tert-Butyl)-6-(trifluoromethyl)pyrimidin-4-yl)piperazin-1-yl)butyl)-3-(pyridin-4-yl)azetidine-1-carboxamide, N-(4-(4-(2-(tert-Butyl)-6-(trifluoromethyl)pyrimidin-4-yl)piperazin-1-yl)butyl)isoindoline-2-carboxamide, N-(4-(4-(2-(tert-Butyl)-6-(trifluoromethyl)pyrimidin-4-yl)piperazin-1-yl)butyl)-5-methoxyisoindoline-2-carboxamide, N-(4-(4-(2-(tert-Butyl)-6-(trifluoromethyl)pyrimidin-4-yl)piperazin-1-yl)butyl)-3,4-dihydroisoquinoline-2(1H)-carboxamide, N-(4-(4-(2-(tert-Butyl)-6-(trifluoromethyl)pyrimidin-4-yl)piperazin-1-yl)butyl)-4,5-dihydro-1H-benzo[d]azepine-3(2H)-carboxamide, 4-([1,1'-Biphenyl]-2-yl)-N-(4-(4-(2-(tert-butyl)-6-(trifluoromethyl)pyrimidin-4-yl)piperazin-1-yl)butyl)piperazine-1-carboxamide, 4-([1,1'-Biphenyl]-3-yl)-N-(4-(4-(2-(tert-butyl)-6-(trifluoromethyl)pyrimidin-4-yl)piperazin-1-yl)butyl)piperazine-1-carboxamide, 4-([1,1'-Biphenyl]-4-yl)-N-(4-(4-(2-(tert-butyl)-6-(trifluoromethyl)pyrimidin-4-yl)piperazin-1-yl)butyl)piperazine-1-carboxamide, N-(4-(4-(2-(tert-Butyl)-6-methylpyrimidin-4-yl)piperazin-1-yl)butyl)-4-(phenylsulfonyl)piperazine-1-carboxamide, N-(4-(4-(2,3-Dichlorophenyl)piperazin-1-yl)butyl)-4-phenylpiperidine-1-carboxamide, N-(4-(4-(2-(tert-Butyl)-6-(trifluoromethyl)pyrimidin-4-yl)piperazin-1-yl)butyl)-4-phenylpiperidine-1-carboxamide, N-(4-(4-(2-(tert-Butyl)-6-(trifluoromethyl)pyrimidin-4-yl)piperazin-1-yl)butyl)-4-hydroxy-4-phenylpiperidine-1-carboxamide, 4-Benzyl-N-(4-(4-(2-(tert-butyl)-6-(trifluoromethyl)pyrimidin-4-yl)piperazin-1-yl)butyl)piperidine-1-carboxamide, N-(4-(4-(2-(tert-Butyl)-6-(trifluoromethyl)pyrimidin-4-yl)piperazin-1-yl)butyl)-4-phenoxypiperidine-1-carboxamide, N-(4-(4-(2-(tert-Butyl)-6-methylpyrimidin-4-yl)piperazin-1-yl)butyl)-4-(2-oxo-2,3-dihydro-1H-benzo[d]imidazol-1-yl)piperidine-1-carboxamide, N-(4-(4-(2-(tert-Butyl)-6-(trifluoromethyl)pyrimidin-4-yl)piperazin-1-yl)butyl)-4-(2-oxo-2,3-dihydro-1H-benzo[d]imidazol-1-yl)piperidine-1-carboxamide, N-(4-(4-(2-(tert-Butyl)-6-(trifluoromethyl)pyrimidin-4-yl)piperazin-1-yl)butyl)-8-cyano-3,4-dihydro-1H-pyrido[4,3-b]indole-2(5H)-carboxamide, N-(4-(4-(2-(tert-Butyl)-6-(trifluoromethyl)pyrimidin-4-yl)piperazin-1-yl)butyl)-1,3,4,9-tetrahydro-2H-pyrido[3,4-b]indole-2-carboxamide, N-(4-(4-(2,6-Di-tert-butylpyrimidin-4-yl)piperazin-1-yl)butyl)-1,3,4,9-tetrahydro-2H-pyrido[3,4-b]indole-2-carboxamide, N-(4-(4-(2-(tert-Butyl)-6-(trifluoromethyl)pyrimidin-4-yl)piperazin-1-yl)butyl)-4-(4-chlorophenyl)piperazine-1-carboxamide, N-(4-(4-(2-(tert-Butyl)-6-(trifluoromethyl)pyrimidin-4-yl)piperazin-1-yl)butyl)-4-(o-tolyl)piperazine-1-carboxamide, N-(4-(4-(2-(tert-Butyl)-6-(trifluoromethyl)pyrimidin-4-yl)piperazin-1-yl)butyl)-4-(4-cyanophenyl)piperazine-1-carboxamide, N-(4-(4-(2-(tert-Butyl)-6-(trifluoromethyl)pyrimidin-4-yl)piperazin-1-yl)butyl)-4-(3,4-dichlorophenyl)piperazine-1-carboxamide, N-(4-(4-(2-(tert-Butyl)-6-(trifluoromethyl)pyrimidin-4-yl)piperazin-1-yl)butyl)-4-(3-cyano-5-(trifluoromethyl)phenyl)piperazine-1-carboxamide, 4-(2-(tert-Butyl)-6-(trifluoromethyl)pyrimidin-4-yl)-N-(4-(4-(2-(tert-butyl)-6-(trifluoromethyl)pyrimidin-4-yl)piperazin-1-yl)butyl)piperazine-1-carboxamide, N-(4-(4-(2-(tert-Butyl)-6-(trifluoromethyl)pyrimidin-4-yl)piperazin-1-yl)butyl)-4-(7-chloroquinolin-4-yl)piperazine-1-carboxamide, N-(4-(4-(2-(tert-Butyl)-6-(trifluoromethyl)pyrimidin-4-yl)piperazin-1-yl)butyl)-4-methylpiperazine-1-carboxamide, N-(4-(4-(2-(tert-Butyl)-6-(trifluoromethyl)pyrimidin-4-yl)piperazin-1-yl)butyl)-4-ethylpiperazine-1-carboxamide, N-(4-(4-(2-(tert-Butyl)-6-(trifluoromethyl)pyrimidin-4-yl)piperazin-1-yl)butyl)-4-isopropylpiperazine-1-carboxamide, 2-Benzyl-N-(4-(4-(2-(tert-butyl)-6-(trifluoromethyl)pyrimidin-4-yl)piperazin-1-yl)butyl)-4-cyclopropylpiperazine-1-carboxamide, N-(4-(4-(2-(tert-Butyl)-6-(trifluoromethyl)pyrimidin-4-yl)piperazin-1-yl)butyl)-4-(cyclopropylmethyl)piperazine-1-carboxamide, N-(4-(4-(2-(tert-Butyl)-6-(trifluoromethyl)pyrimidin-4-yl)piperazin-1-yl)butyl)-4-cyclohexylpiperazine-1-carboxamide, N-(4-(4-(2-(tert-Butyl)-6-(trifluoromethyl)pyrimidin-4-yl)piperazin-1-yl)butyl)-3,4-dihydroquinoline-1(2H)-carboxamide, N-(4-(4-(2-(tert-Butyl)-6-(trifluoromethyl)pyrimidin-4-yl)piperazin-1-yl)butyl)indoline-1-carboxamide, N-(4-(4-(2-(tert-Butyl)-6-(trifluoromethyl)pyrimidin-4-yl)piperazin-1-yl)butyl)-4-(3-cyanobenzyl)piperazine-1-carboxamide, N-(4-(4-(2-(tert-Butyl)-6-(trifluoromethyl)pyrimidin-4-yl)piperazin-1-yl)butyl)-4-((4-chlorophenyl)(phenyl)methyl)piperazine-1-carboxamide, N-(4-(4-(2-(tert-Butyl)-6-(trifluoromethyl)pyrimidin-4-yl)
   piperazin-1-yl)butyl)-4-cinnamylpiperazine-1-carboxam-
   ide,
N-(4-(4-(2-(tert-Butyl)-6-(trifluoromethyl)pyrimidin-4-yl)
   piperazin-1-yl)butyl)-[1,4'-bipiperidine]-1'-carboxamide,
N-(4-(4-(2-(tert-Butyl)-6-(trifluoromethyl)pyrimidin-4-yl)
   piperazin-1-yl)butyl)-4-(1-methylpiperidin-4-yl)pipera-
   zine-1-carboxamide,
N-(4-(4-(2-(tert-Butyl)-6-(trifluoromethyl)pyrimidin-4-yl)
   piperazin-1-yl)butyl)-4-(phenylsulfonyl)piperazine-1-
   carboxamide,
N-(4-(4-(2,6-Di-tert-Butylpyrimidin-4-yl)piperazin-1-yl)
   butyl)-4-(phenylsulfonyl)piperazine-1-carboxamide,
N-(4-(4-(2-(tert-Butyl)-6-(trifluoromethyl)pyrimidin-4-yl)
   piperazin-1-yl)butyl)-4-(4-chlorophenyl)-4-hydroxypip-
   eridine-1-carboxamide,
N-(4-(4-(2-(tert-Butyl)-6-(trifluoromethyl)pyrimidin-4-yl)
   piperazin-1-yl)butyl)-4-cyclopropyl-2-phenylpiperazine-
   1-carboxamide,
N-(4-(4-(2-(tert-Butyl)-6-(trifluoromethyl)pyrimidin-4-yl)
   piperazin-1-yl)butyl)-4-phenyl-1,4-diazepane-1-carbox-
   amide,
N-(4-(4-(2-(tert-Butyl)-6-(trifluoromethyl)pyrimidin-4-yl)
   piperazin-1-yl)butyl)-4-phenylazepane-1-carboxamide,
4-Phenyl-N-(4-(4-(7-(trifluoromethyl)quinolin-4-yl)piper-
   azin-1-yl)butyl)piperazine-1-carboxamide,
4-Phenyl-N-(4-(4-(quinolin-2-yl)piperazin-1-yl)butyl)pip-
   erazine-1-carboxamide,
N-(4-(4-(7-Chloroquinolin-4-yl)piperazin-1-yl)butyl)-4-
   phenylpiperidine-1-carboxamide,
N-(4-(4-(3,5-Di-tert-butylphenyl)piperazin-1-yl)butyl)-4-
   phenylpiperazine-1-carboxamide,
N-(4-(4-(2-(tert-Butyl)-6-(trifluoromethyl)pyrimidin-4-yl)
   piperazin-1-yl)butyl)-3-methyl-5,6-dihydro-[1,2,4]tri-
   azolo[4,3-a]pyrazine-7(8H)-carboxamide,
N-(4-(4-(6-(tert-Butyl)-2-methylpyrimidin-4-yl)piperazin-
   1-yl)butyl)-3-methyl-5,6-dihydro-[1,2,4]triazolo[4,3-a]
   pyrazine-7(8H)-carboxamide,
N-(4-(4-(2-(tert-Butyl)-6-(trifluoromethyl)pyrimidin-4-yl)
   piperazin-1-yl)butyl)-3,4-dihydro-1H-pyrido[4,3-b]in-
   dole-2(5H)-carboxamide,
N-(4-(4-(2-(tert-Butyl)-6-(trifluoromethyl)pyrimidin-4-yl)
   piperazin-1-yl)butyl)-8-methyl-3,4-dihydro-1H-pyrido[4,
   3-b]indole-2(5H)-carboxamide,
N-(4-(4-(2-(tert-Butyl)-6-(trifluoromethyl)pyrimidin-4-yl)
   piperazin-1-yl)butyl)-8-chloro-3,4-dihydro-1H-pyrido[4,
   3-b]indole-2(5H)-carboxamide,
N-(4-(4-(2-(tert-Butyl)-6-(trifluoromethyl)pyrimidin-4-yl)
   piperazin-1-yl)butyl)-8-methoxy-3,4-dihydro-1H-pyrido
   [4,3-b]indole-2(5H)-carboxamide,
N-(4-(4-(2-(tert-Butyl)-6-(trifluoromethyl)pyrimidin-4-yl)
   piperazin-1-yl)butyl)-8-(trifluoromethyl)-3,4-dihydro-
   1H-pyrido[4,3-b]indole-2(5H)-carboxamide,
N-(4-(4-(6-(tert-Butyl)-2-methylpyrimidin-4-yl)piperazin-
   1-yl)butyl)-8-methyl-3,4-dihydro-1H-pyrido[4,3-b]in-
   dole-2(5H)-carboxamide,
N-(4-(4-(6-(tert-Butyl)-2-methylpyrimidin-4-yl)piperazin-
   1-yl)butyl)-8-chloro-3,4-dihydro-1H-pyrido[4,3-b]in-
   dole-2(5H)-carboxamide,
N-(4-(4-(6-(tert-Butyl)-2-methylpyrimidin-4-yl)piperazin-
   1-yl)butyl)-8-methoxy-3,4-dihydro-1H-pyrido[4,3-b]in-
   dole-2(5H)-carboxamide,
N-(4-(4-(3,5-Di-tert-butylphenyl)piperazin-1-yl)butyl)-1,3,
   4,9-tetrahydro-2H-pyrido[3,4-b]indole-2-carboxamide,
N-(4-(4-(6-(tert-Butyl)-2-methylpyrimidin-4-yl)piperazin-
   1-yl)butyl)-8-(trifluoromethyl)-3,4-dihydro-1H-pyrido[4,
   3-b]indole-2(5H)-carboxamide,
4-Phenyl-N-(4-(4-(2-(trifluoromethyl)quinolin-4-yl)piper-
   azin-1-yl)butyl)piperazine-1-carboxamide,
4-Phenyl-N-(4-(4-(2-(trifluoromethyl)quinolin-4-yl)piper-
   azin-1-yl)butyl)piperidine-1-carboxamide,
N-(4-(4-(2-(tert-Butyl)-6-cyclopropylpyrimidin-4-yl)piper-
   azin-1-yl)butyl)-1,3,4,9-tetrahydro-2H-pyrido[3,4-b]in-
   dole-2-carboxamide,
N-(4-(4-(2-(tert-Butyl)-6-(trifluoromethyl)pyrimidin-4-yl)
   piperazin-1-yl)butyl)-3-oxo-4-phenylpiperazine-1-car-
   boxamide,
N-(4-(4-(2-(tert-Butyl)-6-(trifluoromethyl)pyrimidin-4-yl)
   piperazin-1-yl)butyl)-4-phenylcyclohexanecarboxamide,
4-Phenyl-N-(4-(4-(quinolin-4-yl)piperazin-1-yl)butyl)cy-
   clohexanecarboxamide,
N-(4-(4-(7-Chloroquinolin-4-yl)piperazin-1-yl)butyl)-4-
   phenylcyclohexanecarboxamide,
4-Phenyl-N-(4-(4-(quinolin-2-yl)piperazin-1-yl)butyl)cy-
   clohexanecarboxamide,
N-(4-(4-(2-(tert-Butyl)-6-methylpyrimidin-4-yl)piperazin-
   1-yl)butyl)-1-(5-(trifluoromethyl)pyridin-2-yl)piperidine-
   4-carboxamide,
N-(4-(4-(2-(tert-Butyl)-6-(trifluoromethyl)pyrimidin-4-yl)
   piperazin-1-yl)butyl)-1-phenylpiperidine-4-carboxamide,
1-Benzyl-N-(4-(4-(2-(tert-butyl)-6-(trifluoromethyl)pyrimi-
   din-4-yl)piperazin-1-yl)butyl)piperidine-4-carboxamide,
N-(4-(4-(2-(tert-Butyl)-6-(trifluoromethyl)pyrimidin-4-yl)
   piperazin-1-yl)butyl)-1-(5-(trifluoromethyl)pyridin-2-yl)
   piperidine-4-carboxamide,
N-(4-(4-(2-(tert-Butyl)-6-methylpyrimidin-4-yl)piperazin-
   1-yl)butyl)imidazo[1,2-a]pyridine-2-carboxamide,
N-(4-(4-(2-(tert-Butyl)-6-cyclopropylpyrimidin-4-yl)piper-
   azin-1-yl)butyl)imidazo[1,2-a]pyridine-2-carboxamide,
N-(4-(4-(2-(tert-Butyl)-6-(trifluoromethyl)pyrimidin-4-yl)
   piperazin-1-yl)butyl)imidazo[1,2-a]pyridine-2-carbox-
   amide,
N-(4-(4-(2-(tert-Butyl)-6-(trifluoromethyl)pyrimidin-4-yl)
   piperazin-1-yl)butyl)imidazo[1,2-a]pyrimidine-2-carbox-
   amide,
N-(4-(4-(2-(tert-Butyl)-6-(trifluoromethyl)pyrimidin-4-yl)
   piperazin-1-yl)butyl)imidazo[1,2-a]pyrazine-2-carbox-
   amide,
N-(4-(4-(2-(tert-Butyl)-6-(trifluoromethyl)pyrimidin-4-yl)
   piperazin-1-yl)butyl)-6-chloroimidazo[1,2-b]pyridazine-
   2-carboxamide,
N-(4-(4-(Quinolin-4-yl)piperazin-1-yl)butyl)imidazo[1,2-a]
   pyridine-2-carboxamide,
N-(4-(4-(7-Chloroquinolin-4-yl)piperazin-1-yl)butyl)imi-
   dazo[1,2-a]pyridine-2-carboxamide,
N-(4-(4-(2-(tert-Butyl)-6-(trifluoromethyl)pyrimidin-4-yl)
   piperazin-1-yl)butyl)-5-(hydroxymethyl)imidazo[1,2-a]
   pyridine-2-carboxamide,
N-(4-(4-(2-(tert-Butyl)-6-(trifluoromethyl)pyrimidin-4-yl)
   piperazin-1-yl)butyl)-3-((dimethylamino)methyl)imidazo
   [1,2-a]pyridine-2-carboxamide,
N-(4-(4-(2-(tert-Butyl)-6-(trifluoromethyl)pyrimidin-4-yl)
   piperazin-1-yl)butyl)-5-((dimethylamino)methyl)imidazo
   [1,2-a]pyridine-2-carboxamide,
N-(4-(4-(2,6-Di-tert-butylpyrimidin-4-yl)piperazin-1-yl)bu-
   tyl)imidazo[1,2-a]pyridine-2-carboxamide,
N-(4-(4-(2-(tert-Butyl)quinazolin-4-yl)piperazin-1-yl)butyl)
   imidazo[1,2-a]pyridine-2-carboxamide,
N-(4-(4-(7-(Trifluoromethyl)quinolin-4-yl)piperazin-1-yl)
   butyl)imidazo[1,2-a]pyridine-2-carboxamide,
N-(4-(4-(6-(tert-Butyl)-2-methylpyrimidin-4-yl)piperazin-
   1-yl)butyl)imidazo[1,2-a]pyridine-2-carboxamide,
N-(4-(4-(Quinolin-2-yl)piperazin-1-yl)butyl)imidazo[1,2-a]
   pyrimidine-2-carboxamide, N-(4-(4-(Quinazolin-4-yl)piperazin-1-yl)butyl)imidazo[1,2-a]pyridine-2-carboxamide,
3-Bromo-N-(4-(4-(quinolin-4-yl)piperazin-1-yl)butyl)imidazo[1,2-a]pyridine-2-carboxamide,
3-Chloro-N-(4-(4-(quinolin-4-yl)piperazin-1-yl)butyl)imidazo[1,2-a]pyridine-2-carboxamide,
N-(4-(4-(2-(Trifluoromethyl)quinolin-4-yl)piperazin-1-yl)butyl)imidazo[1,2-a]pyridine-2-carboxamide;
pharmaceutically acceptable salt thereof, deuterated form thereof, isomer thereof, and/or solvate thereof.

Embodiment D. A pharmaceutical composition comprising a compound according to any one of Embodiments A-C, pharmaceutically acceptable salts thereof, deuterated forms thereof, isomers thereof, solvates thereof and mixtures thereof and a pharmaceutically acceptable carrier.

Embodiment E. A method for treating a patient suffering from a condition that is capable of treatment with an antagonist or partial agonist of the dopamine D2 and D3 receptors which comprising administering to said patient an effective amount of at least one compound or composition according any one of Embodiments A-C, pharmaceutically acceptable salts thereof, deuterium forms thereof, isomers thereof, solvate thereof and mixture thereof and/or a pharmaceutical composition according to Embodiment D.

Embodiment F. A method for treating a patient suffering from schizophrenia, depressions, neurodegenerative diseases such as Parkinson's, dyskinesias, substance abuse and relapse to substance abuse and addiction to substances such as cocaine, methamphetamine, nicotine and alcohol, glaucoma, cognitive disorders, restless leg syndrome, attention deficit hyperactivity disorders, hyperprolactinemia, autism, motor disturbances such as akathisia, rigor, dystonias as well as various disorders of the urinary tract, which comprises administering to the patient an effective amount of at least one compound or composition according of any one of the Embodiments A-C, pharmaceutically acceptable salts thereof, deuterium forms thereof, isomers thereof, solvate thereof and mixture thereof and/or a pharmaceutical composition according to Embodiment D.

Embodiment G. A process for the preparation of a compound according to any one of Embodiments A-C, wherein said compound is a urea which comprises reacting a 4-aminobutylpiperazine with carbonyldiimidazole and a secondary amine.

Embodiment H. A process for the preparation of a compound according to any one of Embodiments A-C, wherein said compound is an amide which comprises coupling a 4-aminobutylpiperazine with an acid.

The term "comprising" (and its grammatical variations) as used herein is used in the inclusive sense of "having" or "including" and not in the exclusive sense of "consisting only of." The terms "a", "an" and "the" as used herein are understood to encompass the plural as well as the singular, unless indicated otherwise.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A compound selected from the group consisting of:
4-Phenyl-N-(4-(4-phenylpiperazin-1-yl)butyl)piperazine-1-carboxamide,
4-Phenyl-N-(4-(4-(3-(trifluoromethyl)phenyl)piperazin-1-yl)butyl)piperazine-1-carboxamide,
N-(4-(4-(2,3-Dichlorophenyl)piperazin-1-yl)butyl)-4-phenylpiperazine-1-carboxamide,
N-(4-(4-(3-Cyano-5-(trifluoromethyl)phenyl)piperazin-1-yl)butyl)-4-phenylpiperazine-1-carboxamide,
N-(4-(4-(2-(tert-Butyl)-6-methylpyrimidin-4-yl)piperazin-1-yl)butyl)-4-phenylpiperazine-1-carboxamide,
N-(4-(4-(6-(tert-Butyl)-2-methylpyrimidin-4-yl)piperazin-1-yl)butyl)-4-phenylpiperazine-1-carboxamide,
N-(4-(4-(6-Methyl-2-(trifluoromethyl)pyrimidin-4-yl)piperazin-1-yl)butyl)-4-phenylpiperazine-1-carboxamide,
N-(4-(4-(2-(tert-Butyl)-6-(trifluoromethyl)pyrimidin-4-yl)piperazin-1-yl)butyl)-4-phenylpiperazine-1-carboxamide,
N-(4-(4-(2-(tert-Butyl)-6-cyclopropylpyrimidin-4-yl)piperazin-1-yl)butyl)-4-phenylpiperazine-1-carboxamide,
N-(4-(4-(2,6-Di-tert-butylpyrimidin-4-yl)piperazin-1-yl)butyl)-4-phenylpiperazine-1-carboxamide,
4-Phenyl-N-(4-(4-(quinolin-4-yl)piperazin-1-yl)butyl)piperazine-1-carboxamide,
N-(4-(4-(7-Chloroquinolin-4-yl)piperazin-1-yl)butyl)-4-phenylpiperazine-1-carboxamide,
N-(4-(4-(2-(tert-Butyl)quinazolin-4-yl)piperazin-1-yl)butyl)-4-phenylpiperazine-1-carboxamide,
N-(4-(4-(2-(tert-Butyl)-6-(trifluoromethyl)pyrimidin-4-yl)piperazin-1-yl)butyl)-4-(2-chlorophenyl)piperazine-1-carboxamide,
N-(4-(4-(2-(tert-Butyl)-6-(trifluoromethyl)pyrimidin-4-yl)piperazin-1-yl)butyl)-4-(3-chlorophenyl)piperazine-1-carboxamide,
N-(4-(4-(2-(tert-Butyl)-6-(trifluoromethyl)pyrimidin-4-yl)piperazin-1-yl)butyl)-4-(4-chlorophenyl)piperidine-1-carboxamide,
N-(4-(4-(2-(tert-Butyl)-6-(trifluoromethyl)pyrimidin-4-yl)piperazin-1-yl)butyl)-4-cyano-4-phenylpiperidine-1-carboxamide,
N-(4-(4-(2-(tert-Butyl)-6-(trifluoromethyl)pyrimidin-4-yl)piperazin-1-yl)butyl)-4-(2,3-dichlorophenyl)piperazine-1-carboxamide,
N-(4-(4-(2-(tert-Butyl)-6-(trifluoromethyl)pyrimidin-4-yl)piperazin-1-yl)butyl)-4-(2-methoxyphenyl)piperazine-1-carboxamide),
N-(4-(4-(2-(tert-Butyl)-6-(trifluoromethyl)pyrimidin-4-yl)piperazin-1-yl)butyl)-4-(3-methoxyphenyl)piperazine-1-carboxamide,
N-(4-(4-(2-(tert-Butyl)-6-(trifluoromethyl)pyrimidin-4-yl)piperazin-1-yl)butyl)-4-(4-methoxyphenyl)piperazine-1-carboxamide, N-(4-(4-(2-(tert-Butyl)-6-(trifluoromethyl)pyrimidin-4-yl)piperazin-1-yl)butyl)-4-(m-tolyl)piperazine-1-carboxamide, N-(4-(4-(2-(tert-Butyl)-6-(trifluoromethyl)pyrimidin-4-yl)piperazin-1-yl)butyl)-4-(p-tolyl)piperazine-1-carboxamide, N-(4-(4-(2-(tert-Butyl)-6-(trifluoromethyl)pyrimidin-4-yl)piperazin-1-yl)butyl)-4-(2,3-dimethylphenyl)piperazine-1-carboxamide, N-(4-(4-(2-(tert-Butyl)-6-(trifluoromethyl)pyrimidin-4-yl)piperazin-1-yl)butyl)-4-(2-cyanophenyl)piperazine-1-carboxamide, N-(4-(4-(2-(tert-Butyl)-6-(trifluoromethyl)pyrimidin-4-yl)piperazin-1-yl)butyl)-4-(3-cyanophenyl)piperazine-1-carboxamide, N-(4-(4-(2-(tert-Butyl)-6-(trifluoromethyl)pyrimidin-4-yl)piperazin-1-yl)butyl)-4-(3-(trifluoromethyl)phenyl)piperazine-1-carboxamide, N-(4-(4-(2-(tert-Butyl)-6-(trifluoromethyl)pyrimidin-4-yl)piperazin-1-yl)butyl)-4-(4-(trifluoromethyl)phenyl)piperazine-1-carboxamide, N-(4-(4-(2-(tert-Butyl)-6-(trifluoromethyl)pyrimidin-4-yl)piperazin-1-yl)butyl)-4-(pyridin-2-yl)piperazine-1-carboxamide, N-(4-(4-(2-(tert-Butyl)-6-(trifluoromethyl)pyrimidin-4-yl)piperazin-1-yl)butyl)-4-(pyridin-3-yl)piperazine-1-carboxamide, N-(4-(4-(2-(tert-Butyl)-6-(trifluoromethyl)pyrimidin-4-yl)piperazin-1-yl)butyl)-4-(pyridin-4-yl)piperazine-1-carboxamide, N-(4-(4-(2-(tert Butyl-)-6-(trifluoromethyl)pyrimidin-4-yl)piperazin-1-yl)butyl)-4-(pyrimidin-2-yl)piperazine-1-carboxamide, N-(4-(4-(2-(tert-Butyl)-6-(trifluoromethyl)pyrimidin-4-yl)piperazin-1-yl)butyl)-4-(pyrazin-2-yl)piperazine-1-carboxamide, N-(4-(4-(2-(tert-Butyl)-6-(trifluoromethyl)pyrimidin-4-yl)piperazin-1-yl)butyl)-4-(quinolin-4-yl)piperazine-1-carboxamide, N-(4-(4-(2-(tert-Butyl)-6-(trifluoromethyl)pyrimidin-4-yl)piperazin-1-yl)butyl)-4-cyclopropylpiperazine-1-carboxamide, 4-Benzyl-N-(4-(4-(2-(tert-butyl)-6-(trifluoromethyl)pyrimidin-4-yl)piperazin-1-yl)butyl)piperazine-1-carboxamide, 4-Benzoyl-N-(4-(4-(2-(tert-butyl)-6-(trifluoromethyl)pyrimidin-4-yl)piperazin-1-yl)butyl)piperazine-1-carboxamide, N-(4-(4-(2-(tert-Butyl)-6-(trifluoromethyl)pyrimidin-4-yl)piperazin-1-yl)butyl)-3-(pyridin-4-yl)azetidine-1-carboxamide, N-(4-(4-(2-(tert-Butyl)-6-(trifluoromethyl)pyrimidin-4-yl)piperazin-1-yl)butyl)isoindoline-2-carboxamide, N-(4-(4-(2-(tert-Butyl)-6-(trifluoromethyl)pyrimidin-4-yl)piperazin-1-yl)butyl)-5-methoxyisoindoline-2-carboxamide, N-(4-(4-(2-(tert-Butyl)-6-(trifluoromethyl)pyrimidin-4-yl)piperazin-1-yl)butyl)-3,4-dihydroisoquinoline-2(1H)-carboxamide, N-(4-(4-(2-(tert-Butyl)-6-(trifluoromethyl)pyrimidin-4-yl)piperazin-1-yl)butyl)-4,5-dihydro-1H-benzo[d]azepine-3(2H)-carboxamide, 4-([1,1'-Biphenyl]-2-yl)-N-(4-(4-(2-(tert-butyl)-6-(trifluoromethyl)pyrimidin-4-yl)piperazin-1-yl)butyl)piperazine-1-carboxamide, 4-([1,1'-Biphenyl]-3-yl)-N-(4-(4-(2-(tert-butyl)-6-(trifluoromethyl)pyrimidin-4-yl)piperazin-1-yl)butyl)piperazine-1-carboxamide, 4-([1,1'-Biphenyl]-4-yl)-N-(4-(4-(2-(tert-butyl)-6-(trifluoromethyl)pyrimidin-4-yl)piperazin-1-yl)butyl)piperazine-1-carboxamide, N-(4-(4-(2-(tert-Butyl)-6-methylpyrimidin-4-yl)piperazin-1-yl)butyl)-4-(phenylsulfonyl)piperazine-1-carboxamide, N-(4-(4-(2,3-Dichlorophenyl)piperazin-1-yl)butyl)-4-phenylpiperidine-1-carboxamide, N-(4-(4-(2-(tert-Butyl)-6-(trifluoromethyl)pyrimidin-4-yl)piperazin-1-yl)butyl)-4-phenylpiperidine-1-carboxamide, N-(4-(4-(2-(tert-Butyl)-6-(trifluoromethyl)pyrimidin-4-yl)piperazin-1-yl)butyl)-4-hydroxy-4-phenylpiperidine-1-carboxamide, 4-Benzyl-N-(4-(4-(2-(tert-butyl)-6-(trifluoromethyl)pyrimidin-4-yl)piperazin-1-yl)butyl)piperidine-1-carboxamide, N-(4-(4-(2-(tert-Butyl)-6-(trifluoromethyl)pyrimidin-4-yl)piperazin- 1-yl)butyl)-4-phenoxypiperidine-1-carboxamide, N-(4-(4-(2-(tert-Butyl)-6-methylpyrimidin-4-yl)piperazin-1- yl)butyl)-4-(2-oxo-2,3-dihydro-1H-benzo[d]imidazol-1-yl)piperidine-1-carboxamide, N-(4-(4-(2-(tert-Butyl)-6-(trifluoromethyl)pyrimidin-4-yl)piperazin- 1-yl)butyl)-4-(2-oxo-2,3-dihydro-1H-benzo[d]imidazol-1-yl)piperidine-1-carboxamide, N-(4-(4-(2-(tert-Butyl)-6-(trifluoromethyl)pyrimidin-4-yl)piperazin- 1-yl)butyl)- 8-cyano-3,4-dihydro-1H-pyrido[4,3-b]indole-2(5H)-carboxamide, N-(4-(4-(2-(tert-Butyl)-6-(trifluoromethyl)pyrimidin-4-yl)piperazin- 1-yl)butyl)-1,3,4,9-tetrahydro-2H-pyrido[3,4-b]indole-2-carboxamide, N-(4-(4-(2,6-Di-tert-butylpyrimidin-4-yl)piperazin-1-yl)butyl)-1,3,4,9-tetrahydro-2H-pyrido[3,4-b]indole-2-carboxamide, N-(4-(4-(2-(tert-Butyl)-6-(trifluoromethyl)pyrimidin-4-yl)piperazin-1-yl)butyl)-4-(4-chlorophenyl)piperazine-1-carboxamide, N-(4-(4-(2-(tert-Butyl)-6-(trifluoromethyl)pyrimidin-4-yl)piperazin- 1-yl)butyl)-4-(o-tolyl)piperazine-1-carboxamide, N-(4-(4-(2-(tert-Butyl)-6-(trifluoromethyl)pyrimidin-4-yl)piperazin- 1-yl)butyl)-4-(4-cyanophenyl)piperazine-1-carboxamide, N-(4-(4-(2-(tert-Butyl)-6-(trifluoromethyl)pyrimidin-4-yl)piperazin- 1-yl)butyl)-4-(3,4-dichlorophenyl)piperazine-1-carboxamide, N-(4-(4-(2-(tert-Butyl)-6-(trifluoromethyl)pyrimidin-4-yl)piperazin- 1-yl)butyl)-4-(3-cyano-5-(trifluoromethyl)phenyl)piperazine-1-carboxamide, 4-(2-(tert-Butyl)-6-(trifluoromethyl)pyrimidin-4-yl)-N-(4-(4-(2-(tert-butyl)-6-(trifluoromethyl)pyrimidin-4-yl)piperazin-1-yl)butyl)piperazine-1-carboxamide, N-(4-(4-(2-(tert-Butyl)-6-(trifluoromethyl)pyrimidin-4-yl)piperazin-1-yl)butyl)-4-(7-chloroquinolin-4-yl)piperazine-1-carboxamide, N-(4-(4-(2-(tert-Butyl)-6-(trifluoromethyl)pyrimidin-4-yl)piperazin-1-yl)butyl)-4-methylpiperazine-1-carboxamide, N-(4-(4-(2-(tert-Butyl)-6-(trifluoromethyl)pyrimidin-4-yl)piperazin-1-yl)butyl)-4-ethylpiperazine-1-carboxamide, N-(4-(4-(2-(tert-Butyl)-6-(trifluoromethyl)pyrimidin-4-yl)piperazin-1-yl)butyl)-4-isopropylpiperazine-1-carboxamide,
2-Benzyl-N-(4-(4-(2-(tert-butyl)-6-(trifluoromethyl)pyrimidin-4-yl)piperazin-1-yl)butyl)-4-cyclopropylpiperazine-1-carboxamide,
N-(4-(4-(2-(tert-Butyl)-6-(trifluoromethyl)pyrimidin-4-yl)piperazin-1-yl)butyl)-4-(cyclopropylmethyl)piperazine-1-carboxamide,
N-(4-(4-(2-(tert-Butyl)-6-(trifluoromethyl)pyrimidin-4-yl)piperazin-1-yl)butyl)-4-cyclohexylpiperazine-1-carboxamide,
N-(4-(4-(2-(tert-Butyl)-6-(trifluoromethyl)pyrimidin-4-yl)piperazin-1-yl)butyl)-3,4-dihydroquinoline-1(2H)-carboxamide,
N-(4-(4-(2-(tert-Butyl)-6-(trifluoromethyl)pyrimidin-4-yl)piperazin-1-yl)butyl)indoline-1-carboxamide,
N-(4-(4-(2-(tert-Butyl)-6-(trifluoromethyl)pyrimidin-4-yl)piperazin-1-yl)butyl)-4-(3-cyanobenzyl)piperazine-1-carboxamide,
N-(4-(4-(2-(tert-Butyl)-6-(trifluoromethyl)pyrimidin-4-yl)piperazin-1-yl)butyl)-4-((4-chlorophenyl)(phenyl)methyl)piperazine-1-carboxamide,
N-(4-(4-(2-(tert-Butyl)-6-(trifluoromethyl)pyrimidin-4-yl)piperazin-1-yl)butyl)-4-cinnamylpiperazine-1-carboxamide,
N-(4-(4-(2-(tert-Butyl)-6-(trifluoromethyl)pyrimidin-4-yl)piperazin-1-yl)butyl)-[1,4'-bipiperidine]-1'-carboxamide,
N-(4-(4-(2-(tert-Butyl)-6-(trifluoromethyl)pyrimidin-4-yl)piperazin-1-yl)butyl)-4-(1-methylpiperidin-4-yl)piperazine-1-carboxamide,
N-(4-(4-(2-(tert-Butyl)-6-(trifluoromethyl)pyrimidin-4-yl)piperazin-1-yl)butyl)-4-(phenylsulfonyl)piperazine-1-carboxamide,
N-(4-(4-(2,6-Di-tert-butylpyrimidin-4-yl)piperazin-1-yl)butyl)-4-(phenylsulfonyl)piperazine-1-carboxamide,
N-(4-(4-(2-(tert-Butyl)-6-(trifluoromethyl)pyrimidin-4-yl)piperazin-1-yl)butyl)-4-(4-chlorophenyl)-4-hydroxypiperidine-1-carboxamide,
N-(4-(4-(2-(tert-Butyl)-6-(trifluoromethyl)pyrimidin-4-yl)piperazin-1-yl)butyl)-4-cyclopropyl-2-phenylpiperazine-1-carboxamide,
N-(4-(4-(2-(tert-Butyl)-6-(trifluoromethyl)pyrimidin-4-yl)piperazin-1-yl)butyl)-4-phenyl-1,4-diazepane-1-carboxamide,
N-(4-(4-(2-(tert-Butyl)-6-(trifluoromethyl)pyrimidin-4-yl)piperazin-1-yl)butyl)-4-phenylazepane-1-carboxamide,
4-Phenyl-N-(4-(4-(7-(trifluoromethyl)quinolin-4-yl)piperazin-1-yl)butyl)piperazine-1-carboxamide,
4-Phenyl-N-(4-(4-(quinolin-2-yl)piperazin-1-yl)butyl)piperazine-1-carboxamide,
N-(4-(4-(7-Chloroquinolin-4-yl)piperazin-1-yl)butyl)-4-phenylpiperidine-1-carboxamide,
N-(4-(4-(3,5-Di-tert-butylphenyl)piperazin-1-yl)butyl)-4-phenylpiperazine-1-carboxamide,
N-(4-(4-(2-(tert-Butyl)-6-(trifluoromethyl)pyrimidin-4-yl)piperazin-1-yl)butyl)-3-methyl-5,6-dihydro-[1,2,4]triazolo[4,3-a]pyrazine-7(8H)-carboxamide,
N-(4-(4-(6-(tert-Butyl)-2-methylpyrimidin-4-yl)piperazin-1-yl)butyl)-3-methyl-5,6-dihydro-[1,2,4]triazolo[4,3-a]pyrazine-7(8H)-carboxamide,
N-(4-(4-(2-(tert-Butyl)-6-(trifluoromethyl)pyrimidin-4-yl)piperazin-1-yl)butyl)-3,4-dihydro-1H-pyrido[4,3-b]indole-2(5H)-carboxamide,
N-(4-(4-(2-(tert-Butyl)-6-(trifluoromethyl)pyrimidin-4-yl)piperazin-1-yl)butyl)-8-methyl-3,4-dihydro-1H-pyrido[4,3-b]indole-2(5H)-carboxamide,
N-(4-(4-(2-(tert-Butyl)-6-(trifluoromethyl)pyrimidin-4-yl)piperazin-1-yl)butyl)-8-chloro-3,4-dihydro-1H-pyrido[4,3-b]indole-2(5H)-carboxamide,
N-(4-(4-(2-(tert-Butyl)-6-(trifluoromethyl)pyrimidin-4-yl)piperazin-1-yl)butyl)-8-methoxy-3,4-dihydro-1H-pyrido[4,3-b]indole-2(5H)-carboxamide,
N-(4-(4-(2-(tert-Butyl)-6-(trifluoromethyl)pyrimidin-4-yl)piperazin-1-yl)butyl)-8-(trifluoromethyl)-3,4-dihydro-1H-pyrido[4,3-b]indole-2(5H)-carboxamide,
N-(4-(4-(6-(tert-Butyl)-2-methylpyrimidin-4-yl)piperazin-1-yl)butyl)-8-methyl-3,4-dihydro-1H-pyrido[4,3-b]indole-2(5H)-carboxamide,
N-(4-(4-(6-(tert-Butyl)-2-methylpyrimidin-4-yl)piperazin-1-yl)butyl)-8-chloro-3,4-dihydro-1H-pyrido[4,3-b]indole-2(5H)-carboxamide,
N-(4-(4-(6-(tert-Butyl)-2-methylpyrimidin-4-yl)piperazin-1-yl)butyl)-8-methoxy-3,4-dihydro-1H-pyrido[4,3-b]indole-2(5H)-carboxamide,
N-(4-(4-(3,5-Di-tert-butylphenyl)piperazin-1-yl)butyl)-1,3,4,9-tetrahydro-2H-pyrido[3,4-b]indole-2-carboxamide,
N-(4-(4-(6-(tert-Butyl)-2-methylpyrimidin-4-yl)piperazin-1-yl)butyl)-8-(trifluoromethyl)-3,4-dihydro-1H-pyrido[4,3-b]indole-2(5H)-carboxamide,
4-Phenyl-N-(4-(4-(2-(trifluoromethyl)quinolin-4-yl)piperazin-1-yl)butyl)piperazine-1-carboxamide,
4-Phenyl-N-(4-(4-(2-(trifluoromethyl)quinolin-4-yl)piperazin-1-yl)butyl)piperidine-1-carboxamide,
N-(4-(4-(2-(tert-Butyl)-6-cyclopropylpyrimidin-4-yl)piperazin-1-yl)butyl)-1,3,4,9-tetrahydro-2H-pyrido[3,4-b]indole-2-carboxamide,
N-(4-(4-(2-(tert-Butyl)-6-(trifluoromethyl)pyrimidin-4-yl)piperazin-1-yl)butyl)-3-oxo-4-phenylpiperazine-1-carboxamide, pharmaceutically acceptable salt thereof and/or solvate thereof.

2. A pharmaceutical composition comprising a pharmaceutically acceptable carrier and at least one compound according to claim 1, pharmaceutically acceptable salt thereof and/or solvate thereof.

3. The compound according to claim 1, being selected from the group consisting of
4-Phenyl-N-(4-(4-phenylpiperazin-1-yl)butyl)piperazine-1-carboxamide,
N-(4-(4-(2,3-Dichlorophenyl)piperazin-1-yl)butyl)-4-phenylpiperazine-1-carboxamide,
N-(4-(4-(3-Cyano-5-(trifluoromethyl)phenyl)piperazin-1-yl)butyl)-4-phenylpiperazine-1-carboxamide,
N-(4-(4-(2-(tert-Butyl)-6-methylpyrimidin-4-yl)piperazin-1-yl)butyl)-4-phenylpiperazine-1-carboxamide,
N-(4-(4-(6-(tert-Butyl)-2-methylpyrimidin-4-yl)piperazin-1-yl)butyl)-4-phenylpiperazine-1-carboxamide,
N-(4-(4-(6-Methyl-2-(trifluoromethyl)pyrimidin-4-yl)piperazin-1-yl)butyl)-4-phenylpiperazine-1-carboxamide,
N-(4-(4-(2-(tert-Butyl)-6-(trifluoromethyl)pyrimidin-4-yl)piperazin-1-yl)butyl)-4-phenylpiperazine-1-carboxamide,
4-Phenyl-N-(4-(4-(quinolin-4-yl)piperazin-1-yl)butyl)piperazine-1-carboxamide,
N-(4-(4-(2-(tert-Butyl)quinazolin-4-yl)piperazin-1-yl)butyl)-4-phenylpiperazine-1-carboxamide, N-(4-(4-(2-(tert-Butyl)-6-(trifluoromethyl)pyrimidin-4-yl)piperazin-1-yl)butyl)-4-cyano-4-phenylpiperidine-1-carboxamide, N-(4-(4-(2-(tert-Butyl)-6-(trifluoromethyl)pyrimidin-4-yl)piperazin-1-yl)butyl)-4-(3-methoxyphenyl)piperazine-1-carboxamide, N-(4-(4-(2-(tert-Butyl)-6-(trifluoromethyl)pyrimidin-4-yl)piperazin-1-yl)butyl)-4-(3-cyanophenyl)piperazine-1-carboxamide, N-(4-(4-(2-(tert-Butyl)-6-(trifluoromethyl)pyrimidin-4-yl)piperazin-1-yl)butyl)-4-(pyridin-2-yl)piperazine-1-carboxamide, N-(4-(4-(2-(tert-Butyl)-6-(trifluoromethyl)pyrimidin-4-yl)piperazin-1-yl)butyl)-4-(pyridin-3-yl)piperazine-1-carboxamide, N-(4-(4-(2-(tert-Butyl)-6-(trifluoromethyl)pyrimidin-4-yl)piperazin-1-yl)butyl)-4-(pyrimidin-2-yl)piperazine-1-carboxamide, N-(4-(4-(2-(tert-Butyl)-6-(trifluoromethyl)pyrimidin-4-yl)piperazin-1-yl)butyl)-4-(pyrazin-2-yl)piperazine-1-carboxamide, N-(4-(4-(2-(tert-Butyl)-6-(trifluoromethyl)pyrimidin-4-yl)piperazin-1-yl)butyl)-3-(pyridin-4-yl)azetidine-1-carboxamide, N-(4-(4-(2-(tert-Butyl)-6-(trifluoromethyl)pyrimidin-4-yl)piperazin-1-yl)butyl)isoindoline-2-carboxamide, N-(4-(4-(2-(tert-Butyl)-6-(trifluoromethyl)pyrimidin-4-yl)piperazin-1-yl)butyl)-5-methoxyisoindoline-2-carboxamide, N-(4-(4-(2-(tert-Butyl)-6-(trifluoromethyl)pyrimidin-4-yl)piperazin-1-yl)butyl)-4,5-dihydro-1H-benzo[d]azepine-3(2H)-carboxamide, 4-([1,1'-Biphenyl]-2-yl)-N-(4-(4-(2-(tert-butyl)-6-(trifluoromethyl)pyrimidin-4-yl)piperazin-1-yl)butyl)piperazine-1-carboxamide, N-(4-(4-(2,3-Dichlorophenyl)piperazin-1-yl)butyl)-4-phenylpiperidine-1-carboxamide, N-(4-(4-(2-(tert-Butyl)-6-(trifluoromethyl)pyrimidin-4-yl)piperazin-1-yl)butyl)-4-phenylpiperidine-1-carboxamide, N-(4-(4-(2-(tert-Butyl)-6-methylpyrimidin-4-yl)piperazin-1-yl)butyl)-4-(2-oxo-2,3-dihydro-1H-benzo[d]imidazol-1-yl)piperidine-1-carboxamide, N-(4-(4-(2-(tert-butyl)-6-(trifluoromethyl)pyrimidin-4-yl)piperazin-1-yl)butyl)-1,3,4,9-tetrahydro-2H-pyrido[3,4-b]indole-2-carboxamide, N-(4-(4-(6-(tert-Butyl)-2-methylpyrimidin-4-yl)piperazin-1-yl)butyl)-8-methoxy-3,4-dihydro-1H-pyrido[4,3-b]indole-2(5H)-carboxamide, pharmaceutically acceptable salt thereof and/or solvate thereof.

4. A pharmaceutical composition comprising a pharmaceutically acceptable carrier and at least one compound according to claim 3, pharmaceutically acceptable salt thereof and/or solvate thereof.

5. The compound according to claim 1, being N-(4-(4-(2-(tert-Butyl)-6-(trifluoromethyl)pyrimidin-4-yl)piperazin-1-yl)butyl)-5-methoxyisoindoline-2-carboxamide, pharmaceutically acceptable salt thereof and/or solvate thereof.

6. A pharmaceutical composition comprising a pharmaceutically acceptable carrier and the compound according to claim 5, pharmaceutically acceptable salt thereof and/or solvate thereof.

* * * * *

UNITED STATES PATENT AND TRADEMARK OFFICE
CERTIFICATE OF CORRECTION

PATENT NO. : 9,969,743 B2
APPLICATION NO. : 15/463051
DATED : May 15, 2018
INVENTOR(S) : Subramaniam Ananthan It is certified that error appears in the above-identified patent and that said Letters Patent is hereby corrected as shown below:

In the Specification

Column 1, please replace Lines 16-22 after the heading "FEDERALLY SPONSORED RESEARCH AND DEVELOPMENT" with the following:
--"This invention was made with government support under DA018827, and DA024675 awarded by the National Institutes of Health. The government has certain rights in the invention."--

Signed and Sealed this
Seventeenth Day of September, 2024

Katherine Kelly Vidal
*Director of the United States Patent and Trademark Office*